(12) United States Patent
Chao et al.

(10) Patent No.: US 12,399,479 B2
(45) Date of Patent: Aug. 26, 2025

(54) SYSTEMS AND METHODS FOR SUPPORTING MULTIPLE AUTOMATED WORKFLOWS

(71) Applicant: LifeFoundry Inc., Champaign, IL (US)

(72) Inventors: Ran Chao, Champaign, IL (US); Jing Jiang, Champaign, IL (US); Shaoyu Meng, Champaign, IL (US)

(73) Assignee: LifeFoundry Inc., Champaign, IL (US)

( * ) Notice: Subject to any disclaimer, the term of this patent is extended or adjusted under 35 U.S.C. 154(b) by 0 days.

(21) Appl. No.: 18/662,336

(22) Filed: May 13, 2024

(65) Prior Publication Data
US 2025/0044769 A1    Feb. 6, 2025

Related U.S. Application Data

(63) Continuation of application No. 17/259,122, filed as application No. PCT/US2019/043512 on Jul. 25, (Continued)

(51) Int. Cl.
   *G05B 19/31*   (2006.01)
   *B25J 9/16*   (2006.01)
   (Continued)

(52) U.S. Cl.
   CPC ............ *G05B 19/31* (2013.01); *B25J 9/1666* (2013.01); *C04B 30/02* (2013.01); *G05B 11/06* (2013.01);
   (Continued)

(58) Field of Classification Search
   None
   See application file for complete search history.

(56) References Cited

U.S. PATENT DOCUMENTS

| | | | |
|---|---|---|---|
| 4,941,593 A | | 7/1990 | Hicks et al. |
| 5,366,896 A | * | 11/1994 | Margrey ............... G16H 10/40 436/55 |

(Continued)

FOREIGN PATENT DOCUMENTS

| | | |
|---|---|---|
| CN | 106257289 A | 12/2016 |
| EP | 1 598 415 A1 | 11/2005 |
| WO | WO 2016/196942 A1 | 12/2016 |

OTHER PUBLICATIONS

Jamil, "Designing Integrated Computational Biology Pipelines Visually", Jun. 2013, pp. 1-14 (Year: 2013).*

(Continued)

*Primary Examiner* — David Earl Ogg
(74) *Attorney, Agent, or Firm* — MORGAN, LEWIS & BOCKIUS LLP

(57) ABSTRACT

Systems and methods for automated workflow comprise assigning a set of first targets to an uncompiled first workflow. The uncompiled first workflow specifies a first set of process modules. Each such module is associated with a subset of unit operations. Each unit operation includes a time interval and specifies an instrument. For each target in the set of first targets, the uncompiled workflow is translated into an instance of a compiled first workflow comprising a linear temporal order of unit operations, each including execution instructions for an addressed instrument. A set of second targets is obtained and assigned a second uncompiled workflow. Compilation of the second uncompiled workflow for each second target produces a different instance of a compiled second workflow. Each second compiled workflow comprises a linear temporal order of unit operations, with each unit operation including execution instructions for an addressed instrument and specifying a time interval.

34 Claims, 57 Drawing Sheets

Specification includes a Sequence Listing.

Related U.S. Application Data 2019, now Pat. No. 12,117,800, which is a continuation of application No. 16/045,647, filed on Jul. 25, 2018, now Pat. No. 10,732,603.

(51) Int. Cl.

| | | |
|---|---|---|
| *C04B 30/02* | (2006.01) | |
| *G05B 11/06* | (2006.01) | |
| *G05B 19/4155* | (2006.01) | |
| *G06F 9/30* | (2018.01) | |
| *G06F 9/38* | (2018.01) | |
| *G06F 9/455* | (2018.01) | |
| *G06F 15/76* | (2006.01) | |
| *G16B 5/00* | (2019.01) | |
| *G16B 40/00* | (2019.01) | |
| *G16B 50/00* | (2019.01) | |
| *G16B 50/30* | (2019.01) | |
| *G16C 20/90* | (2019.01) | |

(52) U.S. Cl.
CPC .......... *G05B 19/4155* (2013.01); *G06F 9/30* (2013.01); *G06F 9/38* (2013.01); *G06F 9/3851* (2013.01); *G06F 9/455* (2013.01); *G06F 15/76* (2013.01); *G16B 5/00* (2019.02); *G16B 40/00* (2019.02); *G16B 50/00* (2019.02); *G16B 50/30* (2019.02); *G16C 20/90* (2019.02); *G05B 2219/32287* (2013.01); *G05B 2219/40523* (2013.01); *G05B 2219/50391* (2013.01)

(56) References Cited

U.S. PATENT DOCUMENTS

| | | | |
|---|---|---|---|
| 6,862,488 B2 | 3/2005 | Mansour-Awad | |
| 6,963,827 B1 | 11/2005 | Elyea | |
| 7,653,566 B2 | 1/2010 | Kim | |
| 8,141,085 B2 | 3/2012 | Grabarnik | |
| 9,318,108 B2 | 4/2016 | Gruber | |
| 9,410,977 B2 * | 8/2016 | Stone | C12Q 1/6874 |
| 2004/0057619 A1 | 3/2004 | Lim | |
| 2005/0260743 A1 | 11/2005 | Drake et al. | |
| 2006/0155848 A1 | 7/2006 | Brown | |
| 2007/0101007 A1 | 5/2007 | Brown | |
| 2007/0116013 A1 | 5/2007 | Brown | |
| 2007/0276689 A1 | 11/2007 | Slone | |
| 2008/0034055 A1 | 2/2008 | Das | |
| 2008/0114791 A1 | 5/2008 | Takatsu | |
| 2009/0006172 A1 | 1/2009 | Singh | |
| 2009/0292559 A1 | 11/2009 | Ranjan | |
| 2009/0293059 A1 * | 11/2009 | Nathan | G06F 8/34 718/100 |
| 2010/0049740 A1 | 2/2010 | Iwase | |
| 2010/0234994 A1 | 9/2010 | Shi | |
| 2011/0246900 A1 | 10/2011 | Hedges | |
| 2012/0227044 A1 * | 9/2012 | Arumugham | G06Q 10/06 718/100 |
| 2013/0104041 A1 | 4/2013 | Seshagiri | |
| 2013/0124471 A1 | 5/2013 | Chen | |
| 2013/0124574 A1 | 5/2013 | Brettin | |
| 2013/0246460 A1 | 9/2013 | Maltbie | |
| 2014/0012856 A1 | 1/2014 | Abdelrah Man | |
| 2014/0040861 A1 | 2/2014 | Kim | |
| 2014/0180743 A1 | 6/2014 | Lin | |
| 2014/0282177 A1 | 9/2014 | Wang | |
| 2014/0310623 A1 | 10/2014 | O'Connell, Jr. | |
| 2015/0286495 A1 | 10/2015 | Lee | |
| 2016/0253321 A1 | 9/2016 | Lee | |
| 2017/0159045 A1 * | 6/2017 | Serber | G01N 35/00871 |

OTHER PUBLICATIONS

Chao, "Fully Automated One-Step Synthesis of Single-Transcript TALEN Pairs Using a Biological Foundry", Jan. 2017, pp. 1-8 (Year : 2017).*

Cermak et al. "Efficient design and assembly of custom TALEN and other TAL effector-based constructs for DNA targeting" Nucleic Acids Research, vol. 39, No. 12, pp. 1-11 (2011).

Chao, Ran et al. "Fully Automated One-Step Synthesis of Single-Transcript TALEN Pairs Using a Biological Foundry," ACS Synthetic Biology, 2017, American Chemical Society, pp. 678-685.

Engler et al. "A One Pot, One Step, Precision Cloning Method with High Throughput Capability" PLoS One, vol. 3, issue 11, pp. 1-7 (2008).

Esvelt et al. "A System for the Continuous Directed Evolution of Biomolecules" Nature, vol. 472, issue 7344, pp. 499-503 (2011).

Haxthausen, A.E. et al., "Applied Bounded Model Checking for Interlocking System Designs in Software Engineering and Formal Methods", revised selected papers, 2014, vol. 8368, pp. 205-220.

Hollis, R.L. et al. "Real and Virtual Coarse-Fine Robot Bracing Strategies for Precision Assembly," Proceedings of the International Conference on Robotics and Automation, May 12-14, 1992, pp. 767-774.

Hou, Kang et al. "An Autonomous Positioning and Navigation System for Spherical Mobile Robot," Procedia Engineering, SciVerse ScienceDirect, vol. 29, 2012, pp. 2556-2561.

Jamil, "Designing Integrated Computational Biology Pipelines Visually", Jun. 2013, pp. 1-14.

Liang et al. "FairyTALE: a high-throughput TAL effector synthesis platform" ACS Synthetic Biology, vol. 3, pp. 67-73 (2014).

Mariano et al. "Highly efficient genome editing via 2A-coupled co-expression of two TALEN monomers" BMC Research Notes, vol. 7, issue 628, pp. 1-5 (2014).

Sanchez A. et al. Design of procedural controllers for chemical processes. Computers Chemical Engineering, 1995, vol. 19, pp. S381-S586, abstract.

Si, Tong et al. "Automated multiplex genome-scale engineering in yeast," Nature Communications, vol. 8, No. 1, May 4, 2017.

Wang et al. "Programming cells by multiplex genome engineering and accelerated evolution" Nature, vol. 460, issue 7257, pp. 894-898 (2009).

* cited by examiner 1014 continued

1016
The first uncompiled workflow is selected from the group consisting of: cloning, evolutionary organic engineering, genome organic engineering, genotyping, library screening, pathway construction, and protein organic engineering 1018
The plurality of process modules comprises two or more process modules selected from the set: cell culture, DNA assembly, DNA purification, DNA quantification, normalization, polymerase chain reaction (PCR), protein extraction, sample analysis, sample preparation, sampling, and transformation.

1020
The plurality of process modules comprises three or more process modules selected from the above set of process modules.

1022
The plurality of unit operation definitions comprises two or more unit operation definitions from the set: centrifugation, chilled incubation, chromatography, colony selection, colony separation, dispensing, electrophoresis, electroporation, heated incubation, labelling, magnetic separation, mass spectrometry, peeling, pipetting, plate reading, sealing, shaking incubation, spectrophotometry, and thermo-cycling.

1024
The plurality of unit operation definitions comprises three or more unit operation definitions selected from the above set of unit operation definitions.

1026
The plurality of instruments comprise two or more instruments from the set: a liquid handling robot, a temperature controlled block, a microplate reader, a chilled incubator, a heated incubator, a shaking incubator, a reagent dispenser, a plate centrifuge, a storage carousel, a de-lidding station, a blow-dryer, a plate sealer, a label printer, a pipetting device, a shaker, a light box, and a camera.

1028
The plurality of instruments comprises three or more instruments selected from the above set of instruments.

FIG. 3B 1124 continued

1128
The scheduler maximizes, at least in part, by invoking a first number of instances of the first instrument class as a function of the first multiplex value of the first instrument class and invoking a second number of instances of the second instrument class as a function of the second multiplex value of the second instrument class to be run concurrently support concurrently running instances of the compiled first workflow and the compiled second workflow.

1130
The scheduler maximizes, at least in part, by concurrently running a first number of instances of the first compiled workflow and a second number of instances of the second compiled workflow.

1132
The scheduler maximizes, at least in part, by adjusting, by an amount, a time interval of a respective unit operation in the first plurality of unit operations of an instance of the first compiled workflow from the time interval of the corresponding unit operation definition or by adjusting, by an amount, a time interval of a respective unit operation in the second plurality of unit operations of an instance of the second compiled workflow from the time interval of the corresponding unit operation definition.

| Region | | | | | | | | | | | | | | | | |
|---|---|---|---|---|---|---|---|---|---|---|---|---|---|---|---|---|
| 1-4, Optional 5*, 9-15 | AA | AT | AD | AC | | TA | TT | TD | TC | | | | | | | |
| | DA | DT | DD | DC | | CA | CT | CD | CC | | | | | | | |
| 5-7 | AA | AT | AD | AC | | TA | TT | TD | TC | | AA | AT | AD | AC | | TA | TT | TD | TC |
| | DA | DT | DD | DC | | CA | CT | CD | CC | | DA | DT | DD | DC | | CA | CT | CD | CC |
| | GA | GT | GG | GC | AG | TG | GG | CG | | | | | | | | | |
| 8 | A | T | G | C | | | | | | | | | | | | |
| | GA | GT | GG | GC | AG | TG | GG | CG | | | | | | | | | |
| Sender | A-P2A-CMV | | T-P2A-CMV | | G-P2A-CMV | | C-P2A-CMV | | | | | | | | | | |
| Receiver | CMV-A | | CMV-T | | CMV-G | | CMV-C | | | | | | | | | | |

| Target Gene | No. Exp | No. Syn | Cleavage Activity | Sequence Alignment* |
|---|---|---|---|---|
| ASCL1 | 1 | 1 | - | Yes |
| ATOH7 | 2 | 7 | + | |
| ELF1 | 3 | 13 | + | |
| ELK3 | 4 | 17 | + | |
| FOXB1 | 5 | 33 | + | |
| FOXD4L1 | 6 | 41 | + | |
| FOXF2 | 7 | 45 | + | |
| FOXP4 | 8 | 66 | + | |
| GATA1 | 9 | 70 | - | Yes |
| GATA4 | 10 | 73 | - | Yes |
| HES5 | 11 | 82 | - | Yes |
| HOXA10 | 12 | 92 | - | |
| HOXD1 | 13 | 121 | - | Yes |
| HOXD10 | 14 | 122 | + | |
| KLF9 | 15 | 153 | + | |
| LMX1A | 16 | 162 | + | |
| MYF6 | 17 | 178 | - | Yes |
| NEUROG1 | 18 | 185 | - | Yes |
| DHS_37_1 FTN | 19 | 189 | + | |
| DHS_37_2 FTN | 20 | 190 | + | |
| HPRT2 FTN | 21 | 191 | + | |
| HPRT1 FTN | 22 | 192 | + | |

FIG. 12

SEQUENCE LISTING

```
Sequence total quantity: 1
SEQ ID NO: 1           moltype = DNA   length = 72
FEATURE                Location/Qualifiers
misc_feature           1..72
                       note = cleaver
source                 1..72
                       mol_type = other DNA
                       organism = synthetic construct
SEQUENCE: 1
ggcagcggag ctactaactt cagcctgctg aagcaggctg gagatgtgga ggagaaccct   60
ggacctggca tg                                                       72
```

SYSTEMS AND METHODS FOR SUPPORTING MULTIPLE AUTOMATED WORKFLOWS

CROSS REFERENCE TO RELATED APPLICATIONS

The present application is continuation of U.S. patent application Ser. No. 17/259,122, entitled, "Systems and Methods for Supporting Multiple Automated Workflows," filed Jan. 8, 2021, which is a 371 United States National Phase Application of International Patent Cooperation Treaty Application No. PCT/US2019/043512, entitled "Systems and Methods for Supporting Multiple Automated Workflows," filed Jul. 25, 2019, which is a continuation of U.S. patent application Ser. No. 16/045,647, filed Jul. 25, 2018, now U.S. Pat. No. 10,732,603, each of which is hereby incorporated by reference in its entirety for all purposes.

SEQUENCE LISTING

The present Application contains a Sequence Listing in XML format submitted electronically herewith via the United States Patent and Trademark Office Patent Center. The contents of the XML copy, created May 13, 2024, is named "120568-5002-US02—Sequence Listing" and is 4,096 bytes in size. The Sequence Listing is incorporated herein by reference in its entirety for all purposes.

BACKGROUND

Field

The present disclosure relates to systems and methods for supporting biological foundries. More particularly, the present disclosure relates to a systems and methods for fully automated workflows using biological foundries.

Description of Related Art

Electronic devices and components (hereinafter "instruments") have found numerous applications in chemistry and biology (more generally, "life sciences"), especially for detection and measurement of various chemical and biological reactions and identification, detection and measurement of various compounds, and the synthesis of such compounds, to name a few applications. Biological foundries, which comprise lab instruments that are in electronic communication with each other, are being increasing used to automate and handle these applications. Biological foundries can be complex and expensive. Moreover, efficient use of such foundries presents a difficult scheduling problem. For instance, two different processes operating at the foundry may need to use the same instrument. Without some consideration for scheduling, conflicts may arise where two different processes request the same instrument. Moreover, without some consideration for scheduling, the foundry may be under-utilized, with the foundry proceeding to process tasks at some form of lowest common denominator associated with the foundry.

During operation of the foundry, instruments must be precisely controlled in order to ensure proper use, while research materials require meticulous care in order to prevent contamination or spillage. Conventionally, a research scientist is responsible for manually handling samples and actively operating instruments. The research scientist must plan, weigh, and dispense sample batches; sterilize and wash instruments; and then place the sample batches into a variety of instruments. Due to human nature, these sample batches are often inefficiently planned, incorrectly weighed, contaminated, or dropped; any one of which may impair workflow.

To consider the depth and complexity that foundries are capable of handling, consider the uses of the transcription activator-like effector nuclease (TALENs), which is a highly efficient and programmable genome editing tool that has been applied in a wide range of organisms (Sun et al., 2012, "Recent advances in targeted genome organic engineering in mammalian systems," Biotechnol J 7 (9), p 1074). A TALEN comprises a FokI DNA cleavage domain and a DNA binding domain (DBD) that has tandem repeats of a 33-35 amino acids (aa) motif. The twelfth and thirteenth amino acid residue within each repeat is known as repeat-variable di-residue (RVD), and it determines the DNA binding specificity of the repeat. By assembling repeats with specific RVDs in order, a TAL effector DBD can bind to a specific DNA sequence (Boch, 2011, "TALEs of genome targeting," Nat Biotechnol 29 (2), p 135). Because FokI cleavage domain functions as a dimer, TALENs are typically used in tail-to-tail heterodimeric pairs to create double stranded breaks for genome editing (Miller et al., 2011, "A TALE nuclease architecture for efficient genome editing," Nat Biotechnol 29 (2), p 143). Such heterodimeric design generates high editing efficiency and improves specificity, but also presents challenges in TALEN synthesis as well as usage. A number of methods have been developed to synthesize TALEN expression DNA vectors (Briggs et al., 2012, "Iterative capped assembly: rapid and scalable synthesis of repeat-module DNA such as TAL effectors from individual monomers," Nucleic Acids Res, 40 (15), e117; Reyon et al., 2012, "FLASH assembly of TALENs for high-throughput genome editing," Nat Biotechnol, 30 (5), p 460; Ding et al., 2013, "A TALEN genome-editing system for generating human stem cell-based disease models," Cell Stem Cell, 12 (2), p 238; Kim et al., 2013, "A library of TAL effector nucleases spanning the human genome," Nat Biotechnol, 31 (3), p 251; Schmid-Burgk et al., 2013, "A ligation-independent cloning technique for high-throughput assembly of transcription activator-like effector genes," Nat Biotechnol, 31 (1), p 76).

Taking advantage of an optimized set of four base-pair junctions as well as preassembled di-repeat part library, a one-step assembly scheme was developed based on the Golden Gate method using a foundry (Liang et al., 2014, "FairyTALE: A high-throughput TAL effector synthesis platform," ACS Synth Biol, 3 (2), p 67). Custom TALEN vectors could be constructed in 24 hours at 96% success rate and a material cost of five dollars. These methods, however, can only assemble vectors harboring a single TALE-FokI monomer. Since TALEN requires a heterodimer to make a cut, two monomers are introduced into the host cells either on two separate vectors or a single sub-cloned vector with both monomers. Either option has significant drawbacks. For example, both of them will require twice as many vectors synthesized as the number of target sequences. When the monomers are on separate vectors, the number of cells transfected or transformed with both monomers can be reduced. More importantly, the dual vector scheme makes it very difficult to perform high throughput genetic screening. Thanks to fluorescence-activated cell sorting (FACS) and next-generation sequencing, a large number of cells with different genotypes can be screened for phenotypes of interest and sequenced (Shalem et al., 2014, "Genome-scale CRISPR-Cas9 knockout screening in human cells," Science, 343 (6166), p 84; Wang et al., 2014, "Genetic Screens in Human Cells Using the CRISPR-Cas9 System," Science, 343 (6166), p 80). As a precision genome editing tool, TALEN can potentially be used to generate a genomic knock-out library. However, because the two monomers of each TALEN pair need to be introduced to the same cell, library transfection or transformation is not possible using a dual vector system. Moreover, current methods to construct a single-vector TALEN require a lengthy and complicated subcloning procedure, which makes the synthesis process difficult to scale up. A high-throughput synthesis method for single-vector TALENs using a foundry will open up new possibilities.

Thus, prior to the present disclosure there existed a need for fully automated platform to custom manufacture TALENs in a versatile biological foundry. This is just one example of the many needs for improved biological foundries.

The information disclosed in this Background section is only for enhancement of understanding of the general background of the invention and should not be taken as an acknowledgement or any form of suggestion that this information forms the prior art already known to a person skilled in the art.

BRIEF SUMMARY

Advantageously, the systems and methods for supporting fully automated workflows detailed in the present disclosure address the shortcomings in the prior art detailed above.

Transcription activator-like effector nuclease (TALEN) is a programmable genome editing tool with wide applications. Since TALENs perform cleavage of DNA as heterodimers, a pair of TALENs must be synthesized for each target genome locus. Conventionally, TALEN pairs are either expressed on separate vectors or synthesized separately and then subcloned to the same vector. Neither approach allows high-throughput construction of TALEN libraries for large-scale applications. Here we present a single-step assembly scheme to synthesize and express a pair of TALENs in a single transcript format with the help of a P2A self-cleavage sequence. Furthermore, we developed a fully automated platform to custom manufacture TALENs in a versatile biological foundry. Using the systems and methods of the present disclosure, four hundred pairs of TALENs can be synthesized with over 96.2% success rate at a reasonable material cost per pair. This platform opens the door to TALEN-based genome-wide studies, as well as many other applications in the life sciences.

Building on our previously published "FairyTALE" protocol (Liang et al., 2014, "FairyTALE: A high-throughput TAL effector synthesis platform," ACS Synth Biol, 3 (2), p 67), we sought to assemble a pair of TALEN monomers onto a single vector in a one-step reaction. In previous work, 2A self-cleavage peptide (Donnelly et al., 2004, "Multiple gene products from a single vector: 'self-cleaving' 2A peptides," Gene Ther, 11 (23), p 1673; Kim et al., 2011, "High Cleavage Efficiency of a 2A Peptide Derived from Porcine Teschovirus-1 in Human Cell Lines, Zebrafish and Mice," Plos One, 6 (4)) was used to co-transcribe a pair of TALENs as one mRNA molecule but translated as separate functional proteins (Cermak et al., 2015, "High-frequency, precise modification of the tomato genome," Genome Biol, 16, p 232; Mariano et al., 2014, "Highly efficient genome editing via 2A-coupled co-expression of two TALEN monomers. BMC Res Notes, 7, p 628; Xu et al., 2013, "Targeted Myostatin Gene Editing in Multiple Mammalian Species Directed by a Single Pair of TALE Nucleases," Mol Ther Nucleic Acids, 2, e112). We operationalized this co-expression strategy in a 15-insert one-pot assembly scheme, and assembled single-plasmid TALENs in one step at more than 87.7% fidelity. TALENs synthesized using this one-step single-transcript design had comparable cleavage activity in mammalian cells as those synthesized using a two-plasmid design. We implemented the synthesis on iBioFAB (Illinois Biofoundry for Advanced Biomanufacturing), an integrated and versatile robotic system, to fully automate the synthesis process. In accordance with the present disclosure, four hundred pairs of TALENs can be generated on a daily basis at a material cost of $2.1 per pair with minimal human intervention. We envision that genome-wide studies using TALENs can be scaled up to screen hundreds of loci in parallel with such a simplified design and automated synthesis.

Accordingly, various aspects of the present disclosure are directed to providing systems and methods for supporting multiple automated workflows in a biological foundry.

One aspect of the present disclosure provides a non-transitory computer readable storage medium for implementing a workflow. The non-transitory computer readable storage medium stores instructions, which when executed by a first device, cause the first device to obtain a first plurality of organic engineering targets and assign the first plurality of organic engineering targets to a first uncompiled workflow. The first uncompiled workflow is configured to produce the first plurality of organic engineering targets and is associated with a first subset of process modules in a plurality of process modules. Each respective process module in the plurality of process modules is associated with a different subset of unit operation definitions in a plurality of unit operation definitions. Each respective unit operation definition in the plurality of unit operation definitions is independently associated with a corresponding time interval. Each respective unit operation definition in the plurality of unit operations is independently associated with a first subset of instruments in a plurality of instruments (e.g., biofoundry).

The instructions further cause the first device to translate, for each respective organic engineering target in the first plurality of organic engineering targets, the first uncompiled workflow into a corresponding instance of a compiled first workflow for the respective organic engineering target. The corresponding instance of the compiled first workflow comprises, for each respective instrument in the first subset of instruments, an address of the respective instrument and one or more execution instructions for the respective instrument, as well as a first plurality of unit operations. The first plurality of unit operations is temporally organized into a linear temporal order. Each respective unit operation in the first plurality of unit operations is characterized by the time interval of the corresponding unit operation definition, thereby forming a plurality of instances of the compiled first workflow.

Additionally, the instructions further cause the first device to obtain a second plurality of organic engineering targets and to assign the second plurality of organic engineering targets to a second uncompiled workflow. The second uncompiled workflow is configured to produce the second plurality organic engineering targets and is associated with a second subset of process modules in the plurality of process modules. The instructions further cause the first device to translate, for each respective organic engineering target in the second plurality of organic engineering targets, the second uncompiled workflow into a corresponding instance of a compiled second workflow for the respective organic engineering target. The corresponding instance of the compiled second workflow comprises for each respective instrument in the second subset of instruments an address of the respective instrument and one or more execution instructions for the respective instrument, as well as a second plurality of unit operations. The second plurality of unit operations is temporally organized into a linear temporal order. Each respective unit operation in the second plurality of unit operations is characterized by the time interval of the corresponding unit operation definition. A time interval of a unit operation in the second plurality of unit operations is adjusted from a time interval of the corresponding unit operation definition by an amount in accordance with a determination of an interlocking condition with a unit operation in the first compiled workflow, thereby forming a plurality of instances of the compiled second workflow.

In some embodiments, the first or second uncompiled workflow is selected from the group consisting of cloning, evolutionary organic engineering, genome organic engineering, genotyping, library screening, pathway construction, and protein organic engineering.

In some embodiments, the plurality of process modules comprises two or more process modules selected from the set of cell culture, DNA assembly, DNA purification, DNA quantification, normalization, polymerase chain reaction (PCR), protein extraction, sample analysis, sample preparation, sampling, and transformation. In some embodiments, the plurality of process modules comprises three or more process modules selected from the above set of process modules.

In some embodiments, the plurality of unit operation definitions comprises two or more unit operation definitions from the set of centrifugation, chilled incubation, chromatography, colony selection, colony separation, dispensing, electrophoresis, electroporation, heated incubation, labelling, magnetic separation, mass spectrometry, peeling, pipetting, plate reading, sealing, shaking incubation, spectrophotometry, and thermo-cycling. In some embodiments, the plurality of unit operation definitions comprises three or more unit operation definitions from the above set of unit operation definitions.

In some embodiments, the plurality of instruments comprises two or more instruments from the set of a liquid handling robot, a temperature controlled block, a microplate reader, a chilled incubator, a heated incubator, a shaking incubator, a reagent dispenser, a plate centrifuge, a storage carousel, a de-lidding station, a blow-dryer, a plate sealer, a label printer, a pipetting device, a shaker, a light box, and a camera. In some embodiments, the plurality of instruments comprises three or more instruments from the above set of instruments. In some embodiments, the plurality of instruments comprises four or more instruments from the above set of instruments. In some embodiments, the plurality of instruments comprises five or more instruments from the above set of instruments.

In some embodiments, the address of the respective instrument comprises Cartesian coordinates, polar coordinates, spherical coordinates, joint coordinates, or tool coordinates of the respective instrument. In some embodiments, the address of the respective instrument comprises a physical location of the respective instrument. In some embodiments, the address of the respective instrument comprises a unique electronic address of the respective instrument.

In some embodiments, the corresponding instance of the respective compiled workflow further comprises an operating condition for the respective instruction.

In some embodiments, the non-transitory computer readable storage medium further stores instructions for enabling a user of the first device, (e.g., via a graphical user interface), to adjust the linear temporal order of the first plurality of unit operations. In some embodiments, the non-transitory computer readable storage medium further stores instructions for enabling a user of the first device to adjust the linear temporal order of the first plurality of unit operations without using graphical user interface.

In some embodiments, the translating further comprises validating the second plurality of unit operations according to a predetermined validation list. The predetermined validation list comprises one or more criteria of the compiled second workflow. In some embodiments, the one or more criteria of the compiled second workflow comprises a priority of each unit operation in the second plurality of unit operations, a weight of each unit operation in the second plurality of unit operations, a time of completion for the second plurality of unit operations, a compatibility of the second plurality of unit operations to a different plurality of unit operations, a property of each unit operation in the second plurality of unit operations, and one or more constraints of the second plurality of unit operations.

In some embodiments, the property of each unit operation in the second plurality of unit operations is selected from the set of a viscosity value, a purity value, a composition value, a temperature value, a weight value, a mass value, and a volume value.

In some embodiments, the first device is in electronic communication with at least one transport path coupled to the plurality of instruments for receiving a sample from the plurality of instruments and returning the sample to the plurality of instruments. In some embodiments, the transport path comprises at least one transporter configured to move about the transport path, and a physical storage medium disposed on the at least one transporter. In some embodiments, the at least one transporter comprises a robotic arm, a ground vehicle, a drone, a conveyor belt, a transfer station, a lift, a crane, an elevator or a combination thereof. In some embodiments, the at least one transporter further comprises a liquid handling robot.

In some embodiments, the second plurality of organic engineering targets are determined from outputs of the plurality of instances of the compiled first workflow.

In some embodiments, each organic engineering target in the first plurality of organic engineering targets is an input into a corresponding instance of a compiled first workflow in the plurality of instances of the compiled first workflow.

In some embodiments, each organic engineering target in the first plurality of organic engineering targets is an output of a corresponding instance of a compiled first workflow in the plurality of instances of the compiled first workflow.

In some embodiments, each organic engineering target in the first plurality of organic engineering targets is an assembly of nucleic acid components.

In some embodiments, each organic engineering target in the first plurality of organic engineering targets is a plurality of reagents of nucleic acid components.

In some embodiments, each respective compiled workflow in the plurality of instances of the compiled first workflow is a scheme to synthesize and express a pair of TALENs in a single transcript format by a P2A self-cleavage sequence. In some embodiments, at least 400 pairs of TALENs are expressed in a 24-hour time interval.

In some embodiments, the instructions, when executed by the first device, further causes the first device to export the output of a corresponding instance of a compiled first workflow to a second device.

In some embodiments, the first device communicates with at least one external control server or an external database server.

In some embodiments, the instructions, when executed by the first device, further causes the first device to save workflow data describing data of the executed instructions.

In some embodiments, the non-transitory computer readable storage medium further comprises instructions for concurrently executing one or more instances of the compiled first workflow and one or more instances of the compiled second workflow.

In some embodiments, the non-transitory computer readable storage medium further comprises instructions for, at each respective time step in a recurring series of time steps, simulating a remainder of each of the one or more instances of the compiled first workflow thereby forming one or more first simulations. The non-transitory computer readable storage medium further comprises instructions for, at each respective time step in a recurring series of time steps, simulating a remainder of each of the one or more instances of the compiled second workflow thereby forming one or more second simulations. In such embodiments, the non-transitory computer readable storage medium further comprises instructions for firing an interlocking condition error handler associated with a first unit operation in an instance of the one or more instances of the compiled first workflow that forms an interlocking condition with a second unit operation in an instance of the one or more instances of the compiled second workflow.

In some embodiments, firing the interlocking condition error handler adjusts one or more time intervals of one or more unit operations in an instance of the compiled first workflow or an instance of the compiled second workflow that have not been executed.

In some embodiments, firing the interlocking condition error handler adjusts a weight one or more unit operations in an instance of the compiled first workflow or an instance of the compiled second workflow that have not been executed as a function of a priority assigned to the compiled first workflow versus a priority assigned to the compiled second workflow.

In some embodiments, firing the interlocking condition error handler adjusts one or more time intervals of one or more unit operations in an instance of the compiled first workflow or an instance of the compiled second workflow that have not been executed as a function of a priority assigned to the compiled first workflow versus a priority assigned to the compiled second workflow.

In some embodiments, firing the interlocking condition error handler aborts an instance of the compiled first workflow or an instance of the compiled second workflow.

In some embodiments, the interlocking condition error handler is a mutual exclusion error handler.

In some embodiments, the interlocking condition error handler suspends an instance of the compiled first workflow or an instance of the compiled second workflow.

In some embodiments, each time step in the recurring series of time steps occurs on a periodic basis.

In some embodiments, each time step in the recurring series of time steps occurs responsive to an occurrence of event in a plurality of event classes. In some embodiments, the event class is an instrument error, a power failure, a sample dropping, or an interlocking condition.

In some embodiments, each time step in the recurring series of time steps occurs every five minutes. In some embodiments, each time step in the recurring series of time steps occurs every 30 seconds, every minute, every 15 minutes, every 30 minutes, or every hour.

In some embodiments, the non-transitory computer readable storage medium further comprises instructions for concurrently executing two or more instances of the compiled first workflow and two or more instances of the compiled second workflow. In some embodiments, the non-transitory computer readable storage medium further comprises instructions for concurrently executing three or more instances of the compiled first workflow and three or more instances of the compiled second workflow.

In some embodiments, the non-transitory computer readable storage medium further comprises instructions, for each integer k in the set $\{1, \ldots, k, \ldots, n\}$, wherein n is a positive integer of two or greater, to obtain a $k^{th}$ plurality of organic engineering targets and to assign the $k^{th}$ plurality of organic engineering targets to a $k^{th}$ uncompiled workflow. The $k^{th}$ uncompiled workflow is configured to produce the $k^{th}$ plurality organic engineering targets, and the $k^{th}$ uncompiled workflow is associated with a $k^{th}$ subset of process modules in the plurality of process modules. The instructions further cause the first device to translate, for each respective organic engineering target in the $k^{th}$ plurality of organic engineering targets, the $k^{th}$ uncompiled workflow into a corresponding instance of a compiled $k^{th}$ workflow for the respective organic engineering target. The corresponding instance of the compiled $k^{th}$ workflow comprises, for each respective instrument in the $k^{th}$ subset of instruments, an address of the respective instrument and one or more execution instructions for the respective instrument as well as a $k^{th}$ plurality of unit operations. The $k^{th}$ plurality of unit operations is temporally organized into a $k^{th}$ linear temporal order, and each respective unit operation in the $k^{th}$ plurality of unit operations is characterized by the time interval of the corresponding unit operation definition. A time interval of a unit operation in the $k^{th}$ plurality of unit operations is adjusted from the corresponding unit operation definition by an amount in accordance with a determination of an interlocking condition with a unit operation in the first compiled workflow and a unit operation in a second compiled workflow, thereby forming a plurality of instances of the compiled $k^{th}$ workflow.

In some embodiments, the first subset of instruments comprises two or more different instrument classes, and the second subset of instruments comprises two or more different instrument classes.

In some embodiments, a first instrument class and a second instrument class is used by both the plurality of instances of the compiled first workflow and the plurality of instances of the compiled second workflow. The first instrument class has a first multiplex value, and the second instrument class has a second multiplex value, other than the first multiplex value. Furthermore, the non-transitory computer readable storage medium stores instructions for enacting a scheduler that maximizes a number of instances of the plurality of instances of the compiled first workflow, a number of instances of the plurality of instances of the compiled second workflow, or a number of instances of a combination of instances of the compiled first workflow and the compiled second workflow that can concurrently use instruments of the first instrument class and instruments of the second instrument class given the first multiplex value and the second multiplex value.

In some embodiments, the scheduler maximizes, at least in part, by invoking a first number of instances of the first instrument class as a function of the first multiplex value of the first instrument class and invoking a second number of instances of the second instrument class as a function of the second multiplex value of the second instrument class to be run concurrently support concurrently running instances of the compiled first workflow and the compiled second workflow.

In some embodiments, the scheduler maximizes, at least in part, by concurrently running a first number of instances of the first compiled workflow and a second number of instances of the second compiled workflow.

In some embodiments, the scheduler maximizes, at least in part, by adjusting, by an amount, a time interval of a respective unit operation in the first plurality of unit operations of an instance of the first compiled workflow from the time interval of the corresponding unit operation definition or by adjusting, by an amount, a time interval of a respective unit operation in the second plurality of unit operations of an instance of the second compiled workflow from the time interval of the corresponding unit operation definition.

In some embodiments, the method further comprises instructions to concurrently execute two or more of the plurality of instances of the compiled first workflow and two or more of the plurality of instances of the compiled second workflow.

In some embodiments, the method further comprises instructions to concurrently execute two or more of the plurality of instances of the compiled first workflow and two or more of the plurality of instances of the compiled second workflow. In such embodiments, the first subset of instruments comprises two or more instruments, the second subset of instruments comprises two or more instruments, and at least one instrument in the first subset of instruments is in the second subset of instruments.

In some embodiments, the method further comprises instructions to concurrently execute three or more of the plurality of instances of the compiled first workflow and three or more of the plurality of instances of the compiled second workflow. In such embodiments, the first subset of instruments comprises three or more instruments, the second subset of instruments comprises three or more instruments, and at least two instruments in the first subset of instruments is in the second subset of instruments.

In some embodiments, two or more instances of the compiled first workflow are being executed at a time when the translating is executed.

In some embodiments, the non-transitory computer readable storage medium further stores instructions for converting a first organic engineering target in the first plurality of organic engineering targets into one or more first inputs for the first uncompiled workflow.

In some embodiments, the first organic engineering target is synthesis of a first nucleic acid and the one or more first inputs for the first uncompiled workflow are a set of nucleic acid bases for synthesizing the first nucleic acid.

In some embodiments, the first uncompiled workflow includes a branch condition, a loop condition or a nested condition, and wherein the translating resolves a value associated with the branch condition, the loop condition or the nested condition in order to form the linear temporal order of the first plurality of unit operations.

Another aspect of the present disclosure provides methods of implementing workflows at a first device comprising one or more processors, memory storing one or more programs for execution by the one or more processors, a controller, a communications interface, a power supply, and one or more peripheral devices. The one or more programs singularly or collectively use the one or more processors to execute a method. The method comprises obtaining, via the one or more peripheral devices, a first plurality of organic engineering targets and assigning, via the controller, the first plurality of organic engineering targets to a first uncompiled workflow. The first uncompiled workflow is configured to produce the first plurality of organic engineering targets. The first uncompiled workflow is associated with a first subset of process modules in a plurality of process modules. Each respective process module in the plurality of process modules is associated with a different subset of unit operation definitions in a plurality of unit operation definitions. Each respective unit operation definition in the plurality of unit operation definitions is independently associated with a corresponding time interval. Each respective unit operation definition in the plurality of unit operations is independently associated with a first subset of instruments in a plurality of instruments. The methods further include translating, via the controller, for each respective organic engineering target in the first plurality of organic engineering targets, the first uncompiled workflow into a corresponding instance of a compiled first workflow for the respective organic engineering target. The corresponding instance of the compiled first workflow comprises, for each respective instrument in the first subset of instruments, an address of the respective instrument and one or more execution instructions for the respective instrument, as well as a first plurality of unit operations. The first plurality of unit operations is temporally organized into a linear temporal order. Each respective unit operation in the first plurality of unit operations is characterized by the time interval of the corresponding unit operation definition. In this way, a plurality of instances of the compiled first workflow are formed. The methods further comprise obtaining, via the one or more peripheral devices, a second plurality of organic engineering targets and assigning, via the controller, the second plurality of organic engineering targets to a second uncompiled workflow. The second uncompiled workflow is configured to produce the second plurality organic engineering targets. The second uncompiled workflow is associated with a second subset of process modules in the plurality of process modules. Furthermore, the method includes translating, via the controller, for each respective organic engineering target in the second plurality of organic engineering targets, the second uncompiled workflow into a corresponding instance of a compiled second workflow for the respective organic engineering target. The corresponding instance of the compiled second workflow comprises, for each respective instrument in the second subset of instruments, an address of the respective instrument and one or more execution instructions for the respective instrument, and a second plurality of unit operations. The second plurality of unit operations is temporally organized into a linear temporal order. Each respective unit operation in the second plurality of unit operations is characterized by the time interval of the corresponding unit operation definition. Furthermore, the method includes adjusting, via the controller, a time interval of a unit operation in the second plurality of unit operations from a time interval of the corresponding unit operation definition by an amount in accordance with a determination of an interlocking condition with a unit operation in the first compiled workflow. In this way, a plurality of instances of the compiled second workflow are formed.

Another aspect of the present disclosure provides systems for implementing workflows comprising a first device. The first device comprises a display, a power supply, a communications interface, one or more peripheral devices, one or more processors, memory, and one or more programs non-transiently stored in the memory. The one or more programs are configured to be executed by the one or more processors. The one or more programs include instructions for obtaining a first plurality of organic engineering targets and assigning the first plurality of organic engineering targets to a first uncompiled workflow. The first uncompiled workflow is configured to produce the first plurality of organic engineering targets. The first uncompiled workflow is associated with a first subset of process modules in a plurality of process modules. Each respective process module in the plurality of process modules is associated with a different subset of unit operation definitions in a plurality of unit operation definitions. Each respective unit operation definition in the plurality of unit operation definitions is independently associated with a corresponding time interval. Each respective unit operation definition in the plurality of unit operations is independently associated with a first subset of instruments in a plurality of instruments. The one or more programs further include instructions for translating, for each respective organic engineering target in the first plurality of organic engineering targets, the first uncompiled workflow into a corresponding instance of a compiled first workflow for the respective organic engineering target. The corresponding instance of the compiled first workflow comprises, for each respective instrument in the first subset of instruments, an address of the respective instrument and one or more execution instructions for the respective instrument, as well as a first plurality of unit operations. The first plurality of unit operations is temporally organized into a linear temporal order, and each respective unit operation in the first plurality of unit operations is characterized by the time interval of the corresponding unit operation definition. In this way, a plurality of instances of the compiled first workflow are formed. The one or more programs further include instructions for obtaining a second plurality of organic engineering targets and assigning the second plurality of organic engineering targets to a second uncompiled workflow. The second uncompiled workflow is configured to produce the second plurality organic engineering targets. The second uncompiled workflow is associated with a second subset of process modules in the plurality of process modules. The one or more programs further include instructions for translating, for each respective organic engineering target in the second plurality of organic engineering targets, the second uncompiled workflow into a corresponding instance of a compiled second workflow for the respective organic engineering target. The corresponding instance of the compiled second workflow comprises, for each respective instrument in the second subset of instruments, an address of the respective instrument and one or more execution instructions for the respective instrument, as well as a second plurality of unit operations. The second plurality of unit operations is temporally organized into a linear temporal order and each respective unit operation in the second plurality of unit operations is characterized by the time interval of the corresponding unit operation definition. Furthermore, the one or more programs further include instructions for adjusting a time interval of a unit operation in the second plurality of unit operations from a time interval of the corresponding unit operation definition by an amount in accordance with a determination of an interlocking condition with a unit operation in the first compiled workflow, thereby forming a plurality of instances of the compiled second workflow.

Another aspect of the present disclosure provides methods for implementing workflows comprising a first device. The first device comprises a display, a power supply, a communications interface, one or more peripheral devices, one or more processors, memory, and one or more programs non-transiently stored in the memory. The one or more programs are configured to be executed by the one or more processors. The one or more programs include instructions for obtaining a first plurality of organic engineering targets and assigning the first plurality of organic engineering targets to a first uncompiled workflow. The first uncompiled workflow is configured to produce the first plurality of organic engineering targets. The first uncompiled workflow is associated with a first subset of process modules in a plurality of process modules. Each respective process module in the plurality of process modules is associated with a different subset of unit operation definitions in a plurality of unit operation definitions. Each respective unit operation definition in the plurality of unit operation definitions is independently associated with a corresponding time interval. Each respective unit operation definition in the plurality of unit operations is independently associated with a first subset of instruments in a plurality of instruments. The one or more programs further include instructions for translating, for each respective organic engineering target in the first plurality of organic engineering targets, the first uncompiled workflow into a corresponding instance of a compiled first workflow for the respective organic engineering target. The corresponding instance of the compiled first workflow comprises, for each respective instrument in the first subset of instruments, an address of the respective instrument, and one or more execution instructions for the respective instrument, as well as a first plurality of unit operations. The address of the respective instrument includes a coarse grain address that is associated with a marker of the respective instrument. One or more instructions are executed, which includes a coarse traverse instruction and a fine traverse instruction. The coarse traverse instruction commands the transporter to traverse to the respective marker of the respective instrument. The fine traverse instruction commands an articulated handling robot associated with the transporter to move to at least one spatial coordinate associated with the respective instrument (e.g., to move the articulated handling robot). The first plurality of unit operations is temporally organized into a linear temporal order, and each respective unit operation in the first plurality of unit operations is characterized by the time interval of the corresponding unit operation definition. In this way, a plurality of instances of the compiled first workflow are formed.

In some embodiments, the transporter includes a positioning system that is configured to locate and guide the transporter within the transport path.

In some embodiments, the positioning system includes a global positioning system. Accordingly, the respective marker of the respective instrument is a global positioning system coordinate.

In some embodiments, the positioning system includes a representation (e.g., a map) of a surrounding environment of the transport path. Moreover, in some embodiments the representation of the marker positioning of the transport path is either an image feed or a video feed, which can have either a low-pass filter or a Gaussian blurring function is applied to the representation of the marker positioning of the transport path.

In some embodiments, the transporter includes an inertial measurement unit that is configured to verify and correct each execution of the coarse traverse instruction of the respective instruments.

In some embodiments, the articulated handling robot includes a variety of sensors. Each sensor provides information related to a spatial location of the articulated handling robot and a surrounding environment of the articulated handling robot.

In some embodiments, the transporter includes a proportional-integral-derivative (PID) controller. The PID controller communicates with the sensors in order to maintain a spatial location of the transporter through a control loop.

In some embodiments, the articulated handling robot transfers a first tray to a first instrument using a safety transfer procedure. The safety transfer procedure is activated, or enabled, when a readout from the sensors fails to satisfy a threshold proximity value with respect to an actual location of the first instrument. The articulated handling robot activates, or enables, a default transfer procedure when a readout from the sensors satisfies a threshold proximity value with respect to the actual physical location of the first instrument. In some embodiments, the threshold proximity value is a distance (e.g., millimeters) or a degree of rotation/orientation (e.g., degrees or Grad), or a combination thereof.

Yet another aspect of the present disclosure provides systems for implementing workflows, which includes a first device. The first device includes a display, a power supply, a communications interface, and one or more peripheral devices, which includes a reagent handling device. The reagent handling device includes a wash manifold, a primary valve that regulates an internal flow path in the reagent handling device, and variety of reagent containers. Each reagent container includes a valve that controls a flow from the respective reagent container to the primary valve. Moreover, the reagent handling device includes a sterilization container that holds a sterilizing fluid. Similar to the reagent containers, the sterilization container includes a valve that regulates a flow of the sterilization fluid either to the primary valve or to the wash manifold. The wash manifold is coupled to the respective valve of each reagent container, and regulates the flow of the sterilization fluid from the sterilization container to the reagent containers. Furthermore, a dispense manifold is coupled to the primary valve. The dispense manifold includes a variety of dispensers, and control a flow from the primary valve to the dispensers. The first device also includes one or more processors, memory, and one or more programs. The one or more programs are stored in the memory and are configured to be executed by the one or more processors. The one or more programs are configured to be executed by the one or more processors. The one or more programs include instructions for obtaining a first plurality of organic engineering targets and assigning the first plurality of organic engineering targets to a first uncompiled workflow. The first uncompiled workflow is configured to produce the first plurality of organic engineering targets. The first uncompiled workflow is associated with a first subset of process modules in a plurality of process modules. Each respective process module in the plurality of process modules is associated with a different subset of unit operation definitions in a plurality of unit operation definitions. Each respective unit operation definition in the plurality of unit operation definitions is independently associated with a corresponding time interval. Each respective unit operation definition in the plurality of unit operations is independently associated with a first subset of instruments in a plurality of instruments. The one or more programs further include instructions for translating, for each respective organic engineering target in the first plurality of organic engineering targets, the first uncompiled workflow into a corresponding instance of a compiled first workflow for the respective organic engineering target. The corresponding instance of the compiled first workflow comprises, for each respective instrument in the first subset of instruments, an address of the respective instrument, and one or more execution instructions for the respective instrument, as well as a first plurality of unit operations.

In some embodiments, a pressure regulator is coupled to each of the sterilization container, the primary valve, and each reagent container. Furthermore, in some embodiments each pressure regulator further includes a filter that prevents contamination. Moreover, in some embodiments, each pressure regulator further includes a check valve that prevents evaporation or vapor release of a reagent.

In some embodiments, the reagent handling device includes a pump that is coupled to the primary valve. The pump drives the internal flow path of the reagent handling device.

In some embodiments, the reagent handling device includes a dispensing cycle. The dispensing cycle dispenses a selection of reagents from a set of reagent containers. In some embodiments, the reagent handling device includes a first sterilization cycle, which sterilizes a portion of the system. Similarly, in some embodiments the reagent handling device includes a second sterilization cycle that purges a portion of the system.

In some embodiments, each component (e.g., each container, valve, etc.) of the reagent handling device is coupled through removable tubing.

In some embodiments, human intervention is only required to replenish a reagent container and/or to replenish the sterilization fluid of the sterilization container.

Yet another aspect of the present disclosure provides methods for implementing workflows comprising a first device. The first device comprises a display, a power supply, a communications interface, one or more peripheral devices, one or more processors, memory, and one or more programs non-transiently stored in the memory. The one or more programs are configured to be executed by the one or more processors. The one or more programs include instructions for obtaining a first plurality of organic engineering targets and assigning the first plurality of organic engineering targets to a first uncompiled workflow. The first uncompiled workflow is configured to produce the first plurality of organic engineering targets. The first uncompiled workflow is associated with a first subset of process modules in a plurality of process modules. Each respective process module in the plurality of process modules is associated with a different subset of unit operation definitions in a plurality of unit operation definitions. Each respective unit operation definition in the plurality of unit operation definitions is independently associated with a corresponding time interval. Each respective unit operation definition in the plurality of unit operations is independently associated with a first subset of instruments in a plurality of instruments. The one or more programs further include instructions for translating, for each respective organic engineering target in the first plurality of organic engineering targets, the first uncompiled workflow into a corresponding instance of a compiled first workflow for the respective organic engineering target. The corresponding instance of the compiled first workflow comprises, for each respective instrument in the first subset of instruments, an address of the respective instrument, and one or more execution instructions for the respective instrument, as well as a first plurality of unit operations. The one or more execution instructions include instructions for a multi-well plate centrifuge instrument. These instructions include determining a mass of each multi-well plate in a first set of multi-well plates. Each multi-well plate is disposed into the multi-well plate centrifuge. Furthermore, each respective multi-well plate has a corresponding counter balance in a set of counter balances, which is disposed in the multi-well plate centrifuge at a position opposite the respective multi-well plate. Without human intervention, a mass of each respective counter balance is adjusted to be equal to the corresponding multi-well plate. The multi-well centrifuge is then operated. The first plurality of unit operations is temporally organized into a linear temporal order, and each respective unit operation in the first plurality of unit operations is characterized by the time interval of the corresponding unit operation definition. In this way, a plurality of instances of the compiled first workflow are formed.

In some embodiments, the first set of multi-well plates is a single multi-well plate.

In some embodiments, the first set of multi-well plates is a set of from two multi-well plates to five multi-well plates.

In some embodiments, the adjusting includes pumping fluid (e.g., water, mineral oil, gas) to the respective counter balance in order to adjust the mass therein.

In some embodiments, the adjusting includes drawing fluid from the respective counter balance in order to adjust the mass therein.

In some embodiments, each counter balance includes a bottom end portion that is configured to pool fluid therein.

In some embodiments, the determining and the adjusting are performed simultaneously.

In some embodiments, the adjusting includes storing the adjusted mass of each counter balance.

In some embodiments, the one or more instructions for the multi-well plate centrifuge instrument includes determining a mass of each multi-well plate in a second set of multi-well plates, disposing each multi-well plate in the second set into the centrifuge, adjusting, without human intervention, the mass of each counter balance in a second set of counter balances to be equal to the mass of the corresponding multi-well plate in the second set of multi-well plates, and operating the multi-well plate centrifuge.

In some embodiments, the second set of multi-well plates are the first set of multi-well plates.

The automated biological foundry of the present invention has other features and advantages that will be apparent from, or are set forth in more detail in, the accompanying drawings, which are incorporated herein, and the following Detailed Description, which together serve to explain certain principles of exemplary embodiments of the present invention.

BRIEF DESCRIPTION OF THE DRAWINGS

FIGS. 3A, 3B, 3C, 3D, 3E, 3F, 3G, 3H, 3I, 3J, 3K, and 3L collectively illustrate a flow chart of methods for supporting automated workflows using a first device in accordance with an embodiment of the present disclosure, in which optional steps or embodiments are indicated by dashed boxes;

FIG. 11A and FIG. 11B illustrate a list of substrates according to an embodiment of the present disclosure;

FIG. 12 illustrates a list of results from T7E1 assay according to an embodiment of the present disclosure;

Figure 1A:
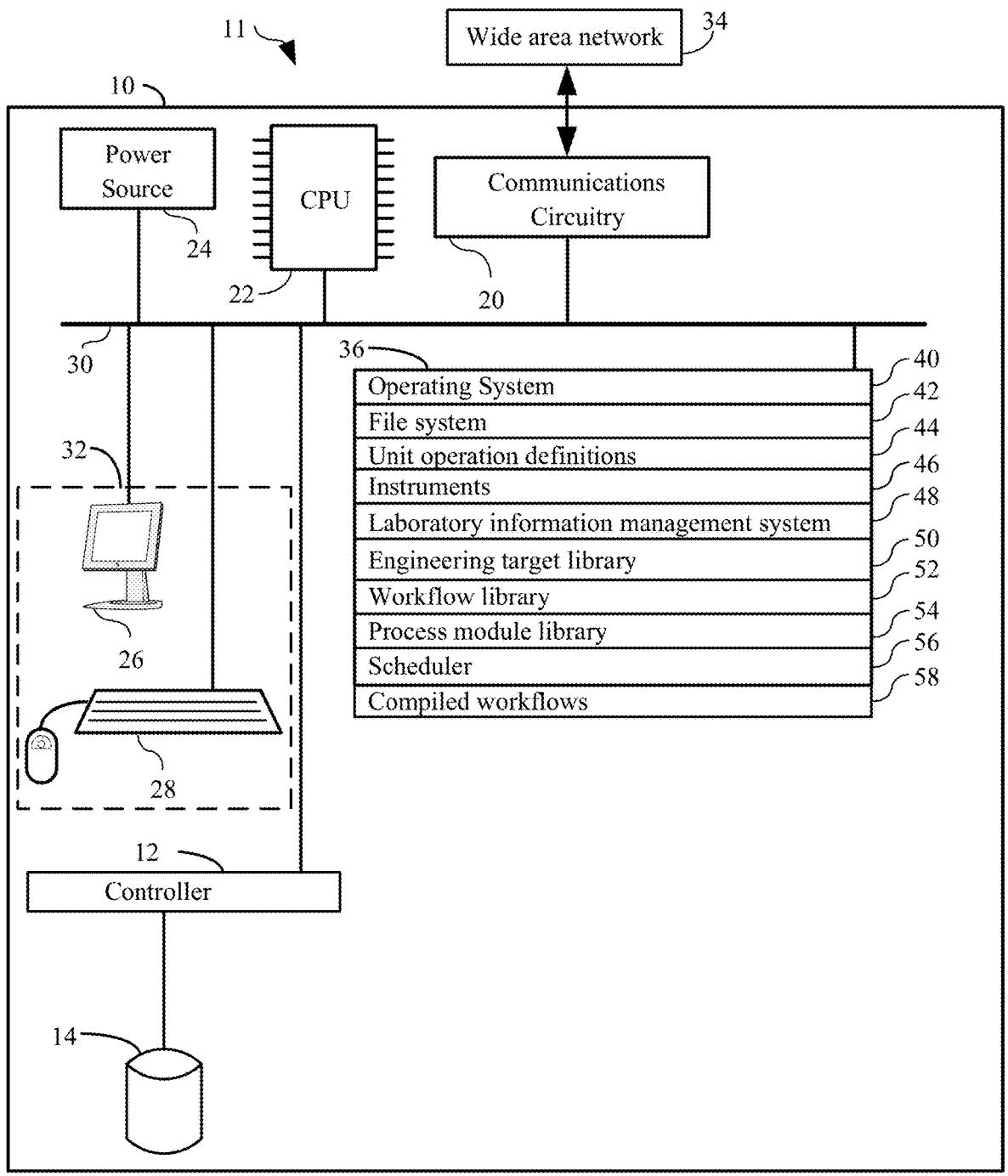
FIGS. 1A, 1B, 1C, and 1D illustrate a computer system in accordance with an embodiment of the present disclosure.
Figure 1B:
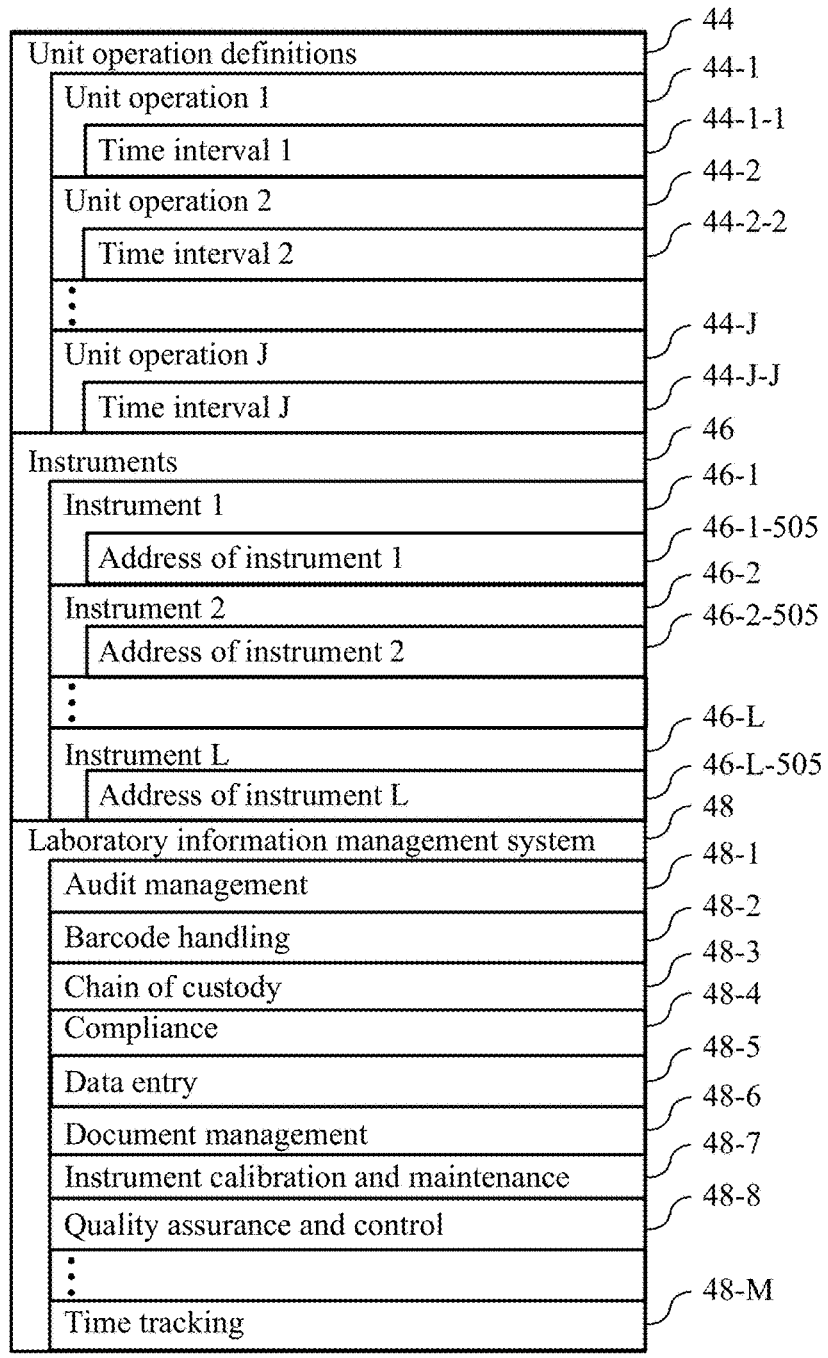
Figure 1C:
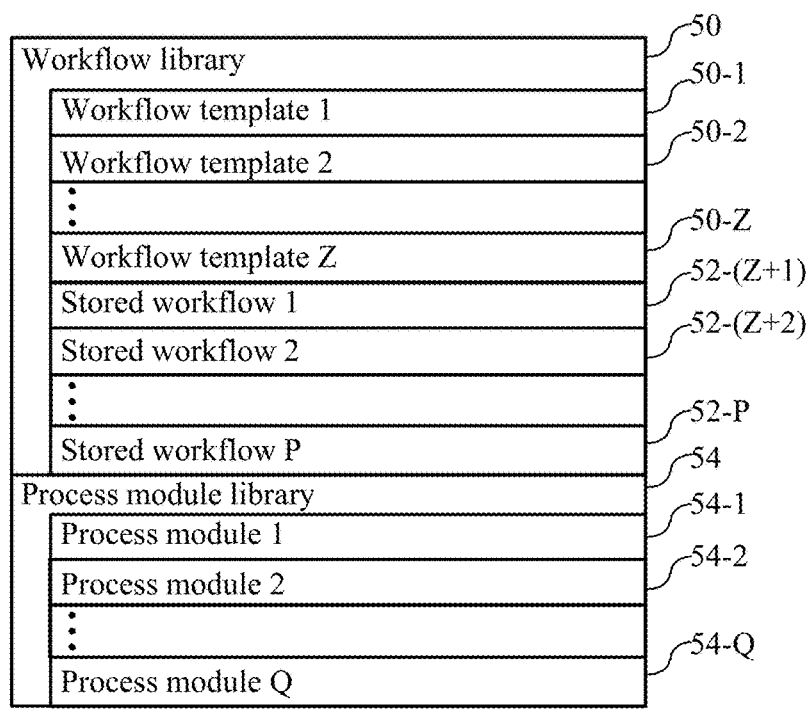
Figure 1D:
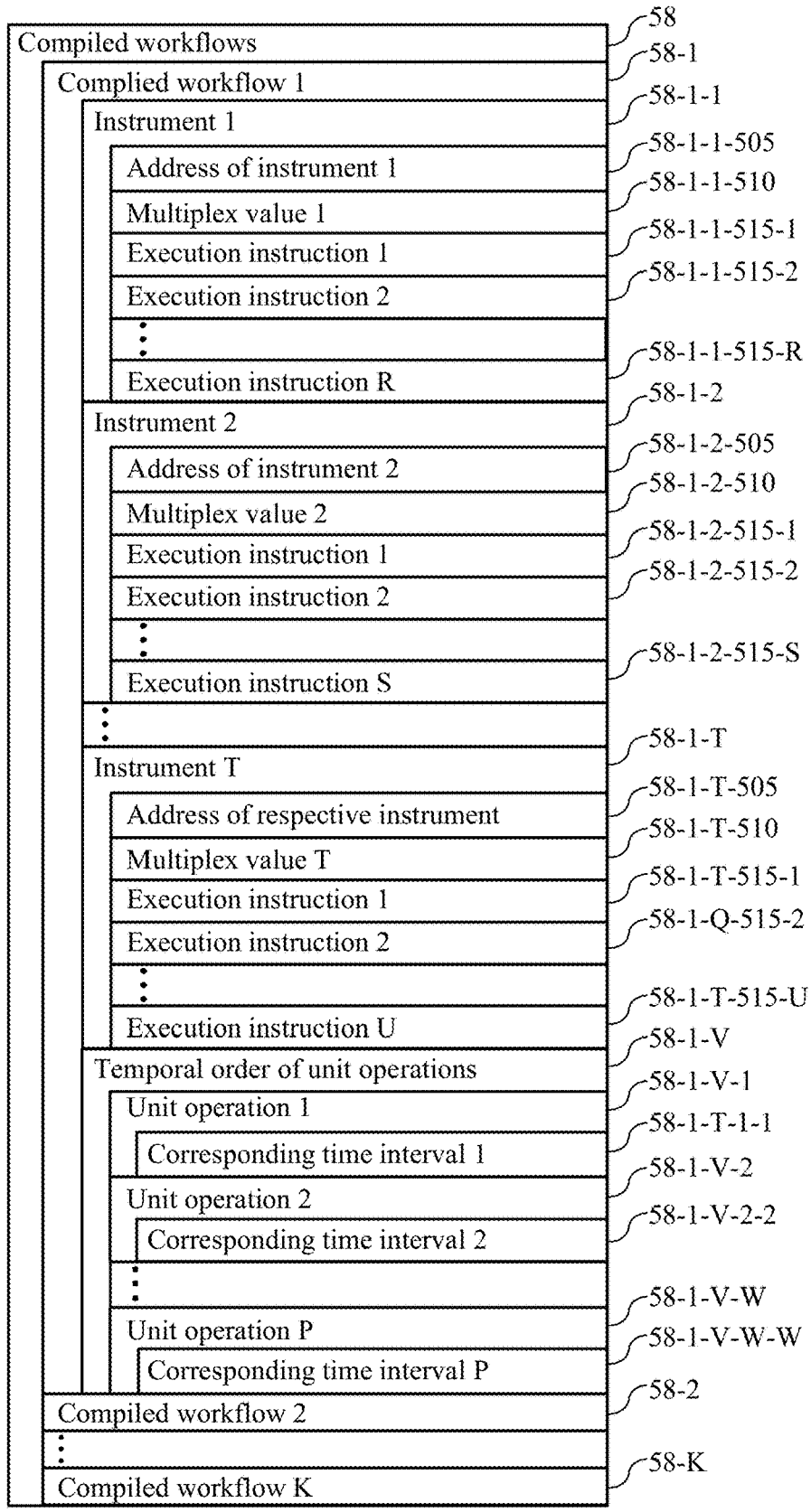

The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

As used herein, in some embodiments, the term "set" means two or more, three or more, or four or more.

It will also be understood that, although the terms first, second, etc. may be used herein to describe various elements, these elements should not be limited by these terms. These terms are only used to distinguish one element from another. For example, a first workflow could be termed a second workflow, and, similarly, a second workflow could be termed a first workflow, without departing from the scope of the present disclosure. The first workflow and the second workflow are both workflows, but they are not the same workflow.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

In some embodiments, systems and methods for supporting automated workflows in accordance with the present disclosure obtain a first set of targets and assign these targets to a first uncompiled workflow type. This first uncompiled workflow type is configured to produce the targets. Moreover, the first uncompiled workflow comprise process modules each of which is further associated with a subset of unit operation definitions. Each unit operation definition is associated with a time interval. Each unit operation is further associated with a subset of instruments. The present disclosure translates the first uncompiled workflow, for each target in the first set of targets, into an instance of a first compiled workflow. The instance of the first compiled workflow comprises an address of the instruments and execution instructions for the instruments. The unit operations are organized into a linear temporal order.

The systems and methods of the present disclosure further support obtaining a set of second targets and assigning them to an uncompiled second workflow. This uncompiled second workflow may be the same or different then the uncompiled first workflow. The uncompiled second workflow is configured to produce the second targets. The uncompiled second workflow is associated with different process modules from the first uncompiled workflow. The second uncompiled workflow is translated into an instance of a compiled second workflow for each respective target in the set of second targets. Moreover, a time interval of unit operations in the second workflow is adjusted from the corresponding unit operation definition by an amount in determination of an interlocking condition with a unit operation in the first compiled workflow. In this way, one or more of the second compiled workflows can be executed on the same foundry at the same time as one or more of the first compiled workflows are executed. In fact, in some embodiments, two or more of the second compiled workflows are executed on the same foundry at the same time as two or more of the first compiled workflows.

In this way, multiple workflows can be run on the same foundry in an efficient manner. Although mechanisms for compiling two different types of workflows and running them on the same foundry have been disclosed, the present disclosure is not so limited. In some embodiments, two or more instances of three or more, four or more, five or more, ten or more, twenty or more, or one hundred or more different types of compiled workflows are concurrently run on the same foundry by adjusting the time interval of unit operations in the respective workflows to avoid interlocking conditions.

FIG. 1 details just such an exemplary system 11 for use in supporting multiple workflows in a biological foundry. The system preferably comprises a computer system 10 having:

a central processing unit (CPU) 22;

a main non-volatile (non-transitory) storage unit 14, for example a hard disk drive, for storing software and data, the storage unit 14 controlled by storage controller 12;

a system memory 36, preferably high speed random-access memory (RAM), for storing system control programs, data, and application programs, comprising programs and data loaded from non-volatile storage unit 14; system memory 36 may also include read-only memory (ROM);

a user interface 32, comprising one or more input devices (e.g., keyboard 28, a mouse) and a display 26 or other output device;

optionally, a network interface card 20 (communications interface) for connecting to any wired or wireless communication network 34 (e.g., a wide area network such as the Internet);

a power source 24 to power the aforementioned elements; and an internal bus 30 for interconnecting the aforementioned elements of the system.

Operation of computer 10 is controlled primarily by operating system 40, which is executed by central processing unit 22. Operating system 40 can be stored in system memory 36. In a typical implementation, system memory 36 also includes:

a file system 42 for controlling access to the various files and data structures;

unit operation definitions 44 which includes execution instructions for a plurality of instruments and physical or chemical procedures to impart on the organic engineering targets conducted by a single instrument;

instruments 46 including addresses of each instrument;

laboratory information management system 48 which includes features support modules to manage operations of a laboratory;

an engineering target library 50 comprising tables of plausible and/or stored engineering targets;

a workflow library 52 comprising a table of predetermined workflows, workflow templates, and stored workflows;

a process module library 54 comprising a table of predetermined process modules and stored process modules;

a scheduler 56 which assists in managing and organizing operations of workflows; and compiled workflows 58 comprising the data of compiled workflows.

As illustrated in FIG. 1, computer 10 comprises data such as unit operation definitions 44, engineering target library 50, workflow library 52 and the like. Such data can be stored in any form of data storage system including, but not limited to, a flat file, a relational database (SQL), or an on-line analytical processing (OLAP) database (MDX and/or variants thereof). In some embodiments, as associated data is stored in a single database. In other embodiments, as well as associated data is stored in a plurality of databases that may or may not all be hosted by the same computer 10. In such embodiments, some components as well as associated data are stored on computer systems that are not illustrated by FIG. 1 but that are addressable by wide area network 34.

In some embodiments, unit operation definitions 44 as well as associated data for such instruments 46, engineered target library 50, workflow library 52, process modules 54, and related software modules illustrated in FIG. 1 are on a single computer (e.g., computer 10) and in other embodiments they are hosted by several computers (not shown). In fact, all possible arrangements of unit operation definitions 44, instruments 46, engineered target library 50, workflow library 52, process modules 54, and the modules illustrated in FIG. 1 on one or more computers are within the scope of the present disclosure so long as these components are addressable with respect to each other across computer network 34 or by other electronic means. Thus, the present disclosure fully encompasses a broad array of computer systems.

Now that a system has been described for supporting multiple automated workflows in accordance with various exemplary embodiments of the present disclosure, details regarding some processes in accordance with FIG. 3 will be disclosed. FIG. 3 collectively illustrates a flow chart of methods for supporting multiple automated workflows in accordance with an exemplary embodiment of the present disclosure. In the flow chart, the preferred parts of the methods are shown in solid line boxes whereas optional variants of the methods, or optional equipment used by the methods, are shown in dashed line boxes. As such, FIG. 3 illustrates methods for supporting multiple automated workflows.

Certain steps are performed by various modules in memory 36. It will be appreciated that the steps described in FIG. 3 can be encoded in a single module or any combination of modules.

In describing the methods of FIG. 3, a first workflow and a second workflow are described in many embodiments. It should be appreciated, however, that in accordance with the present disclosure there can, for each integer k in the set $\{1, \ldots, k, \ldots, n\}$, where n is a positive integer of two or greater, exist n total workflows. Additionally, n refers to a maximum number in a given set. Thus a $k^{th}$ workflow is a generic workflow in the set of n workflows. As such, a theoretical limit, or bottleneck, to a number of active workflows is a number of instruments in a given system or a throughput of a given instrument or class of instruments.

Referring to blocks 1002-1006 of FIG. 3A, a method for implementing workflows will now be described. At a first device (e.g., computer 10 of FIG. 1) comprising one or more processors, memory storing one or more programs for execution by the one or more processors, a controller (e.g., controller 12 of FIG. 1), a communications interface (e.g., communications circuitry 20 of FIG. 1), a power supply (e.g., power source 24 of FIG. 1), and one or more peripheral devices (e.g., keyboard 28 and display 26 of FIG. 1), the one or more programs singularly or collectively executing a given method.

In some embodiments, the first device communicates with at least one external control server or external database server. In some embodiments, data is saved by the first device which describes data of the workflow and/or executed instructions. For instance, in some embodiments the data is exported as one or more tab delimited files, CSV files, EXCEL spreadsheets, GOOGLE Sheets, or in a form suitable for an SQL database. Additionally, such communication can be utilized for a plurality of purposes, including, but not limited to, communicating with first devices of other systems, saving data of a workflow to an external webserver or database server, saving data which describes the executed instructions of instruments, or the like. Examples of networks include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document (1004, 1006).

Figure 3A:
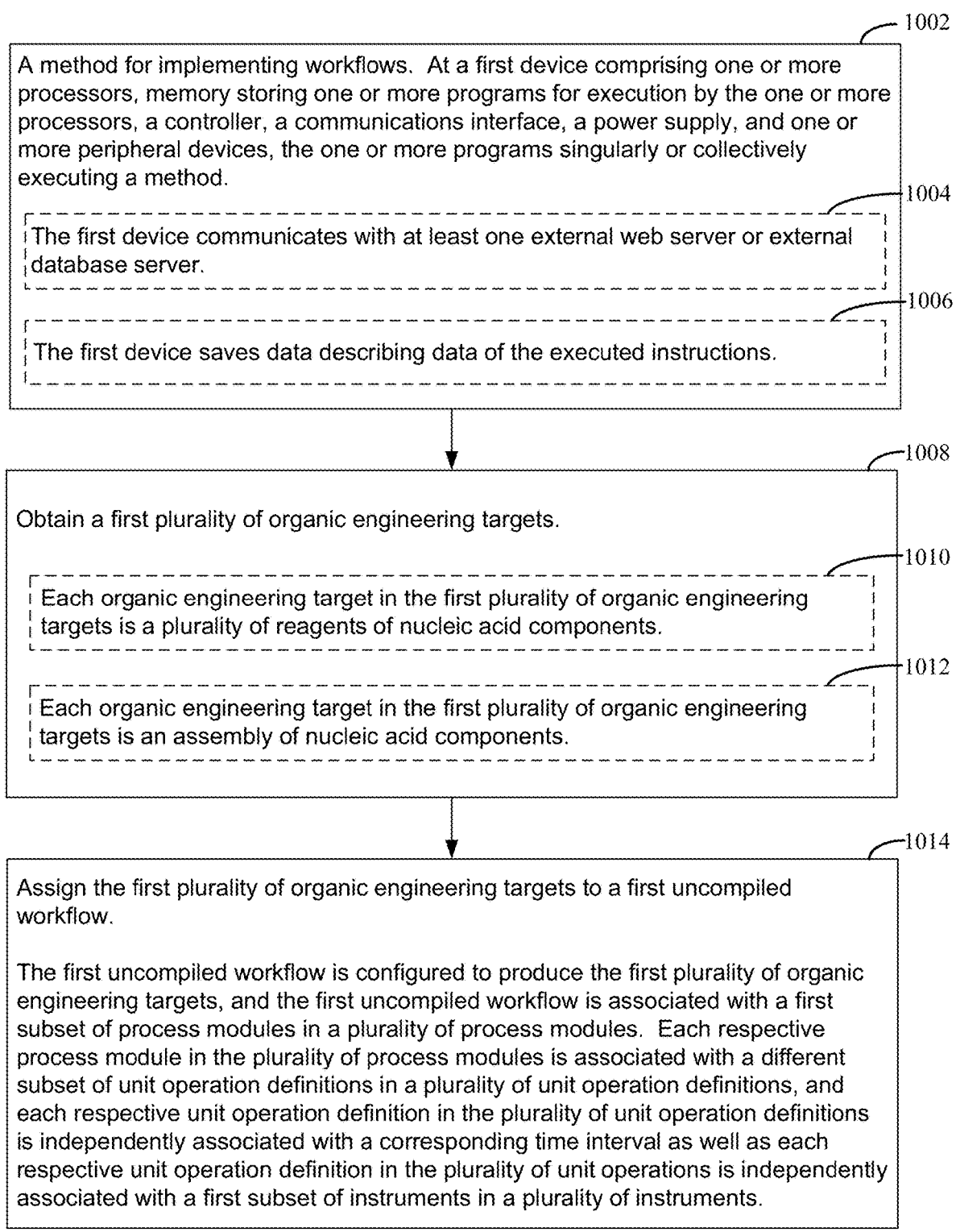
Figure 3C:
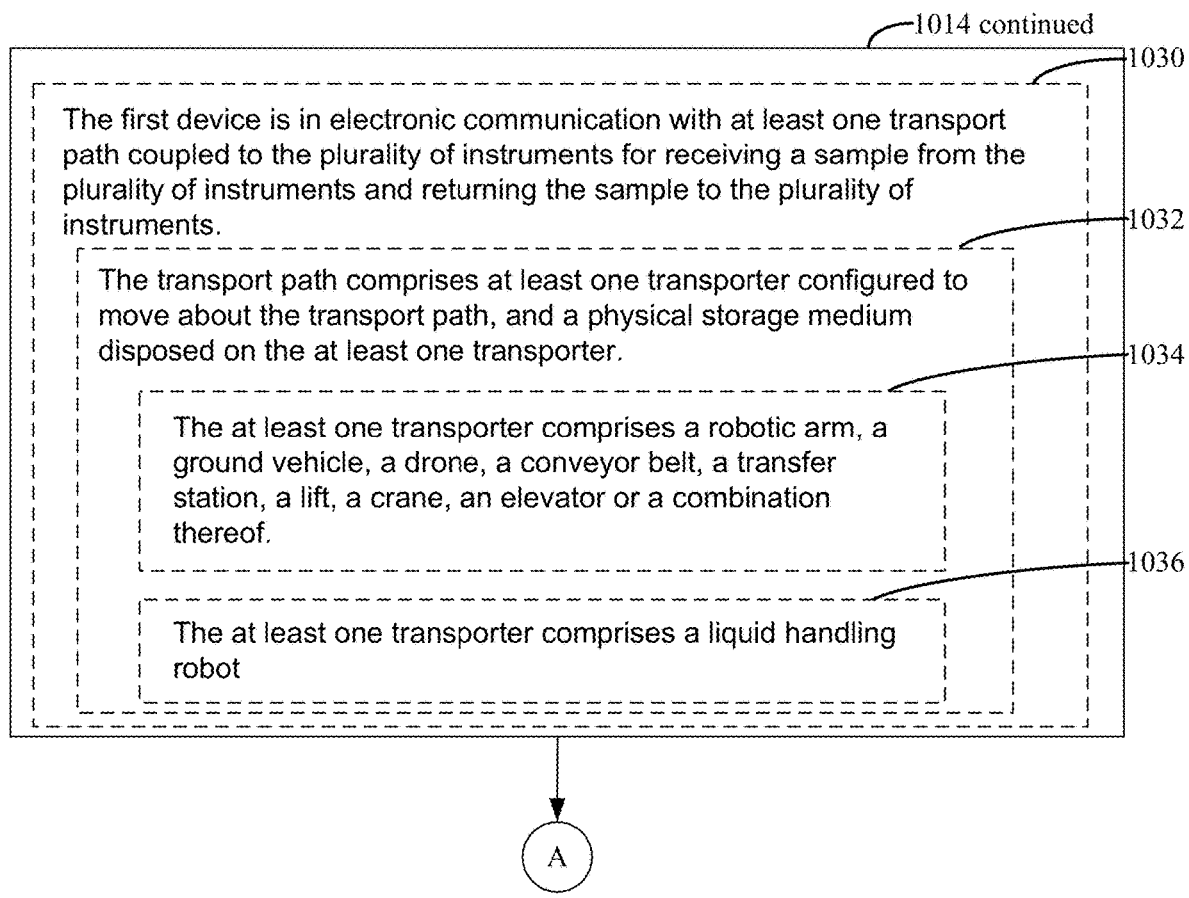
Figure 3D:
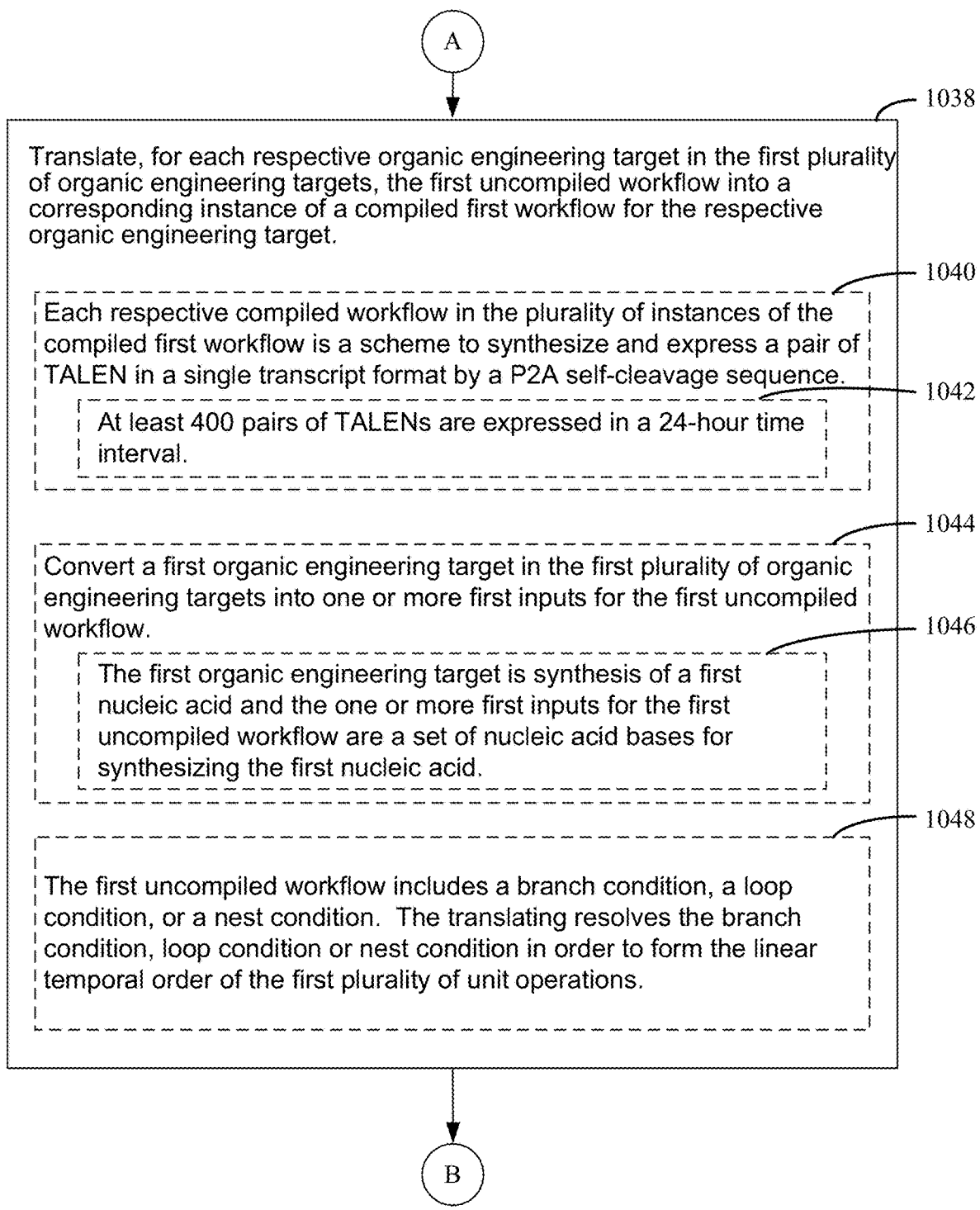
Figure 3E:
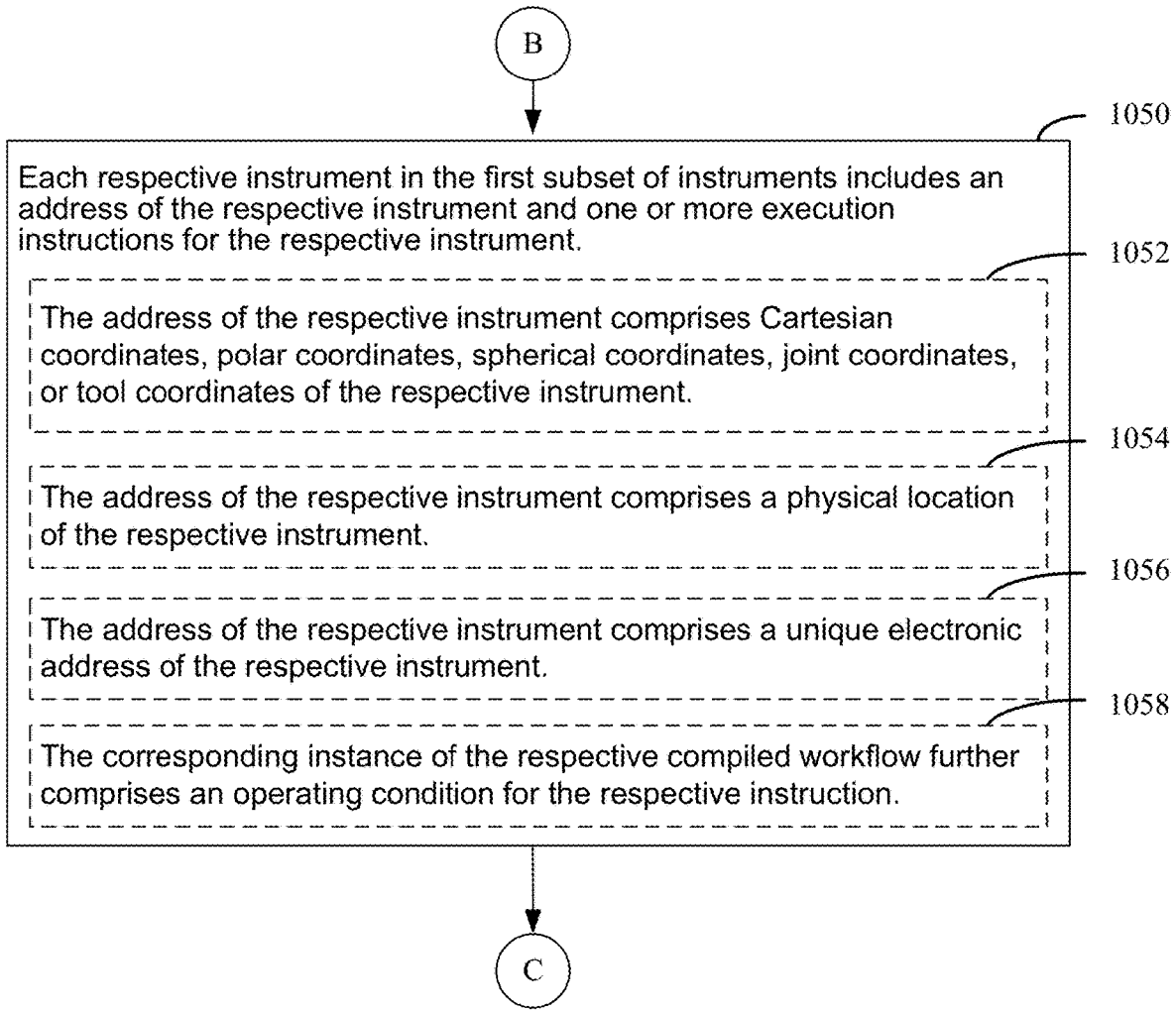
Figure 3F:
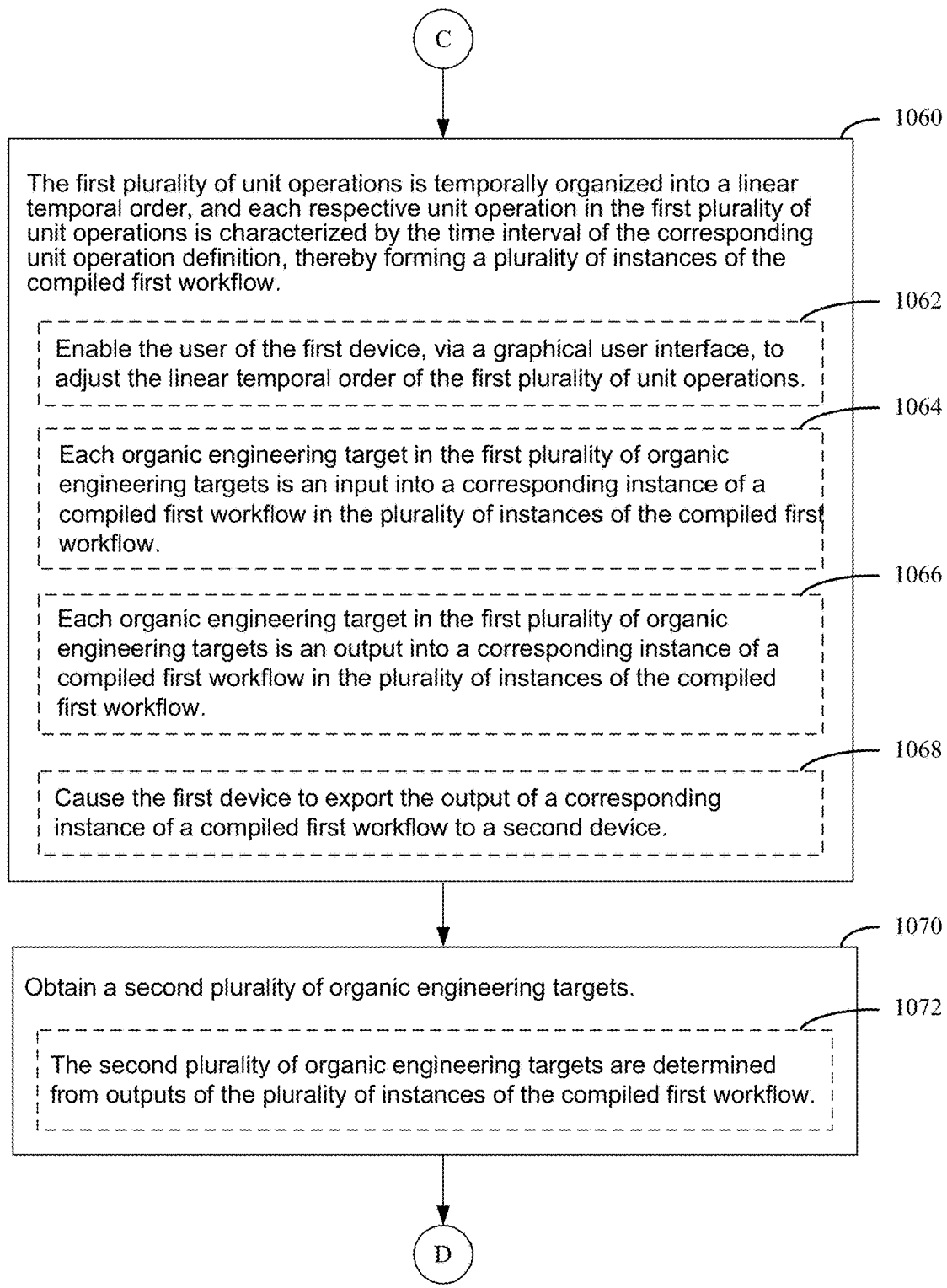
Figure 3G:
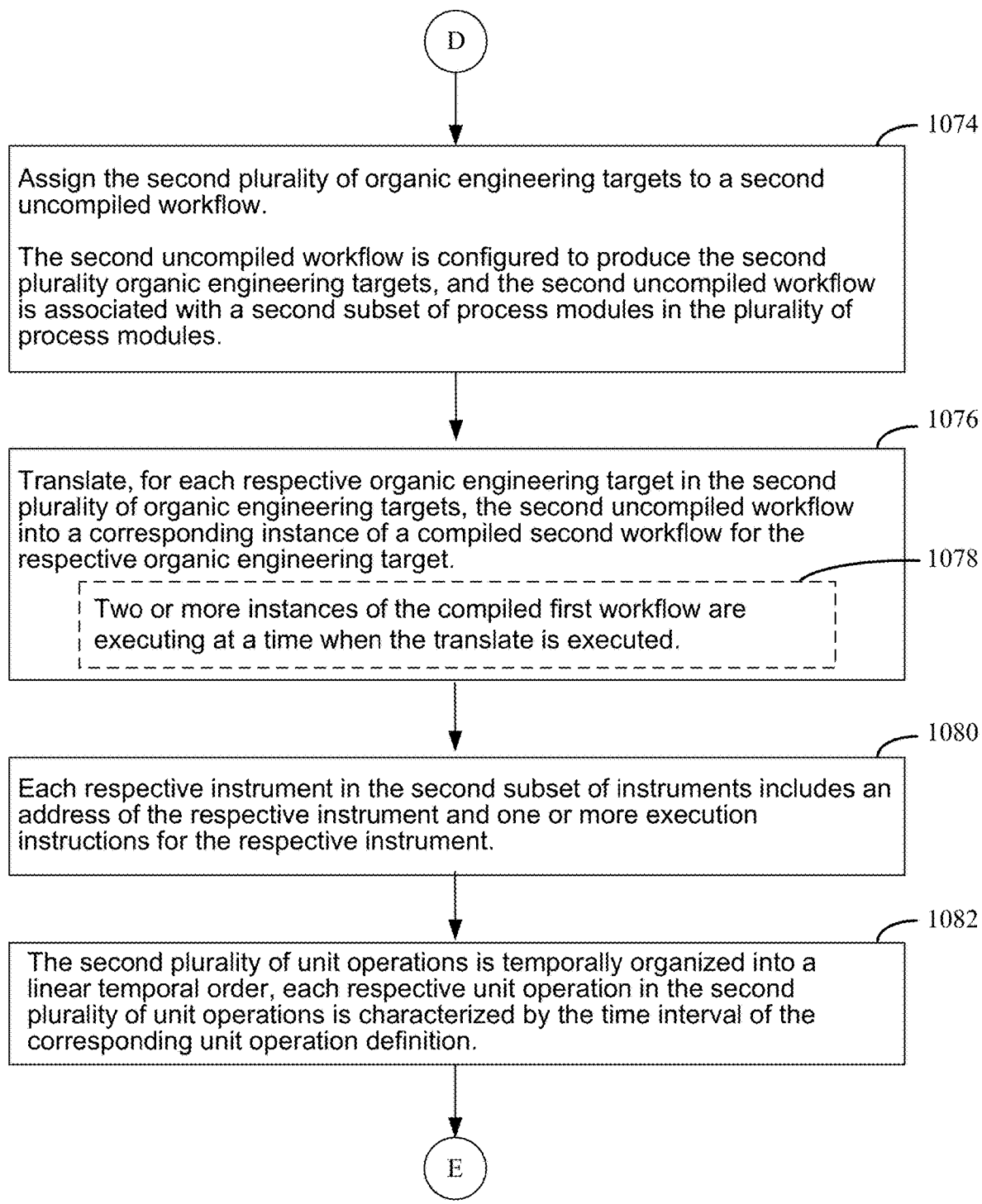
Figure 3H:
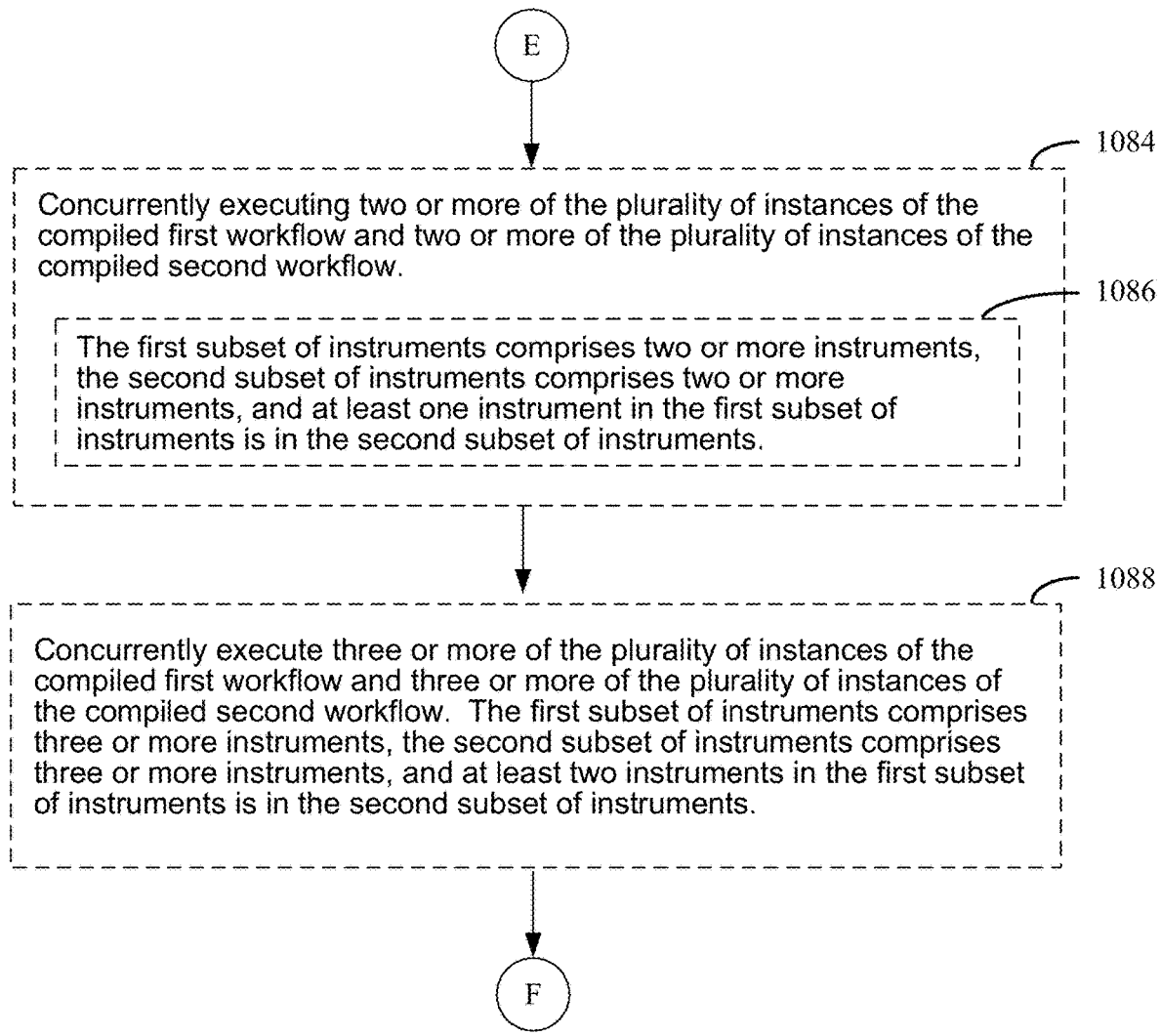
Figure 3I:
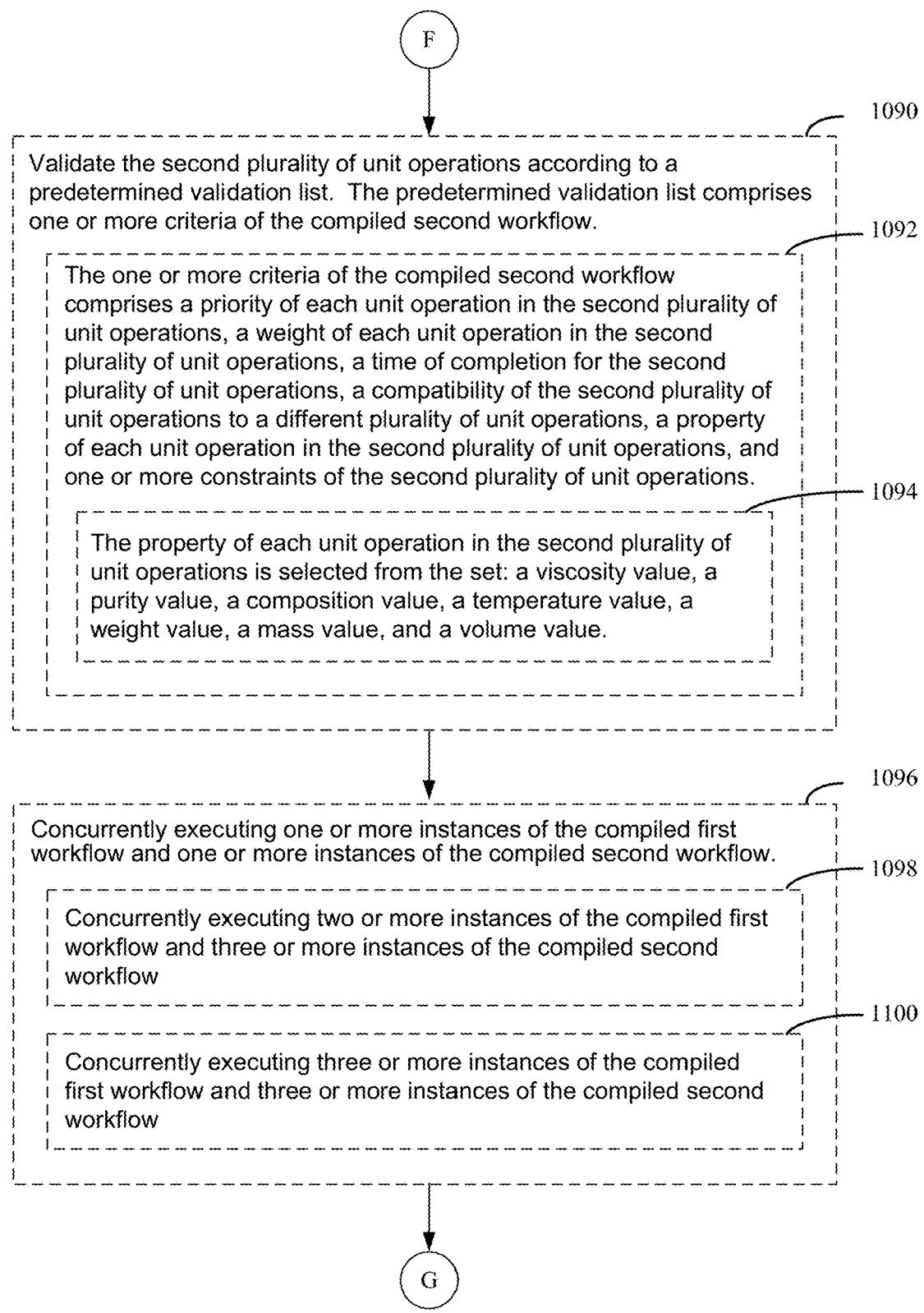
Figure 3J:
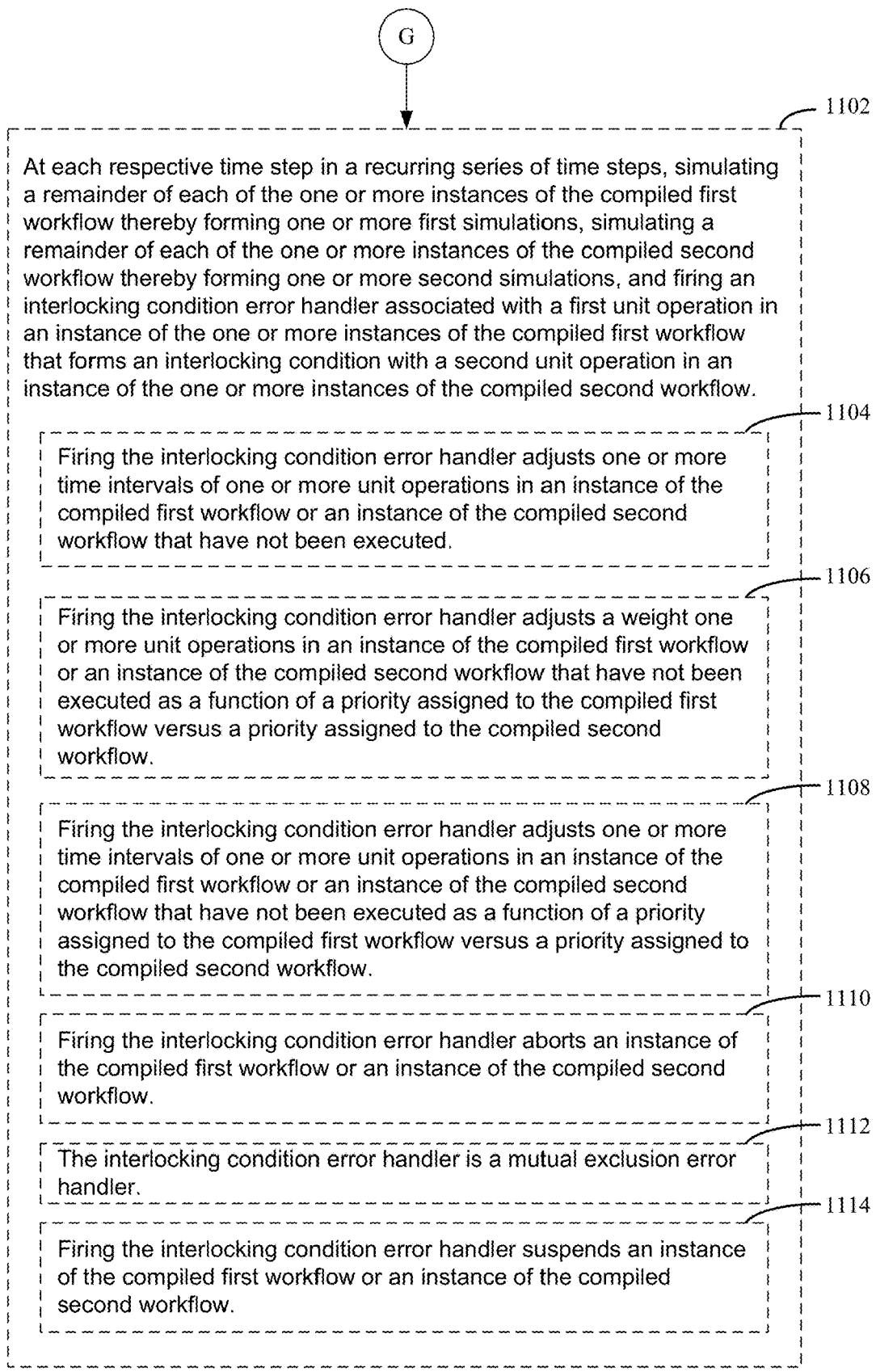
Figure 3K:
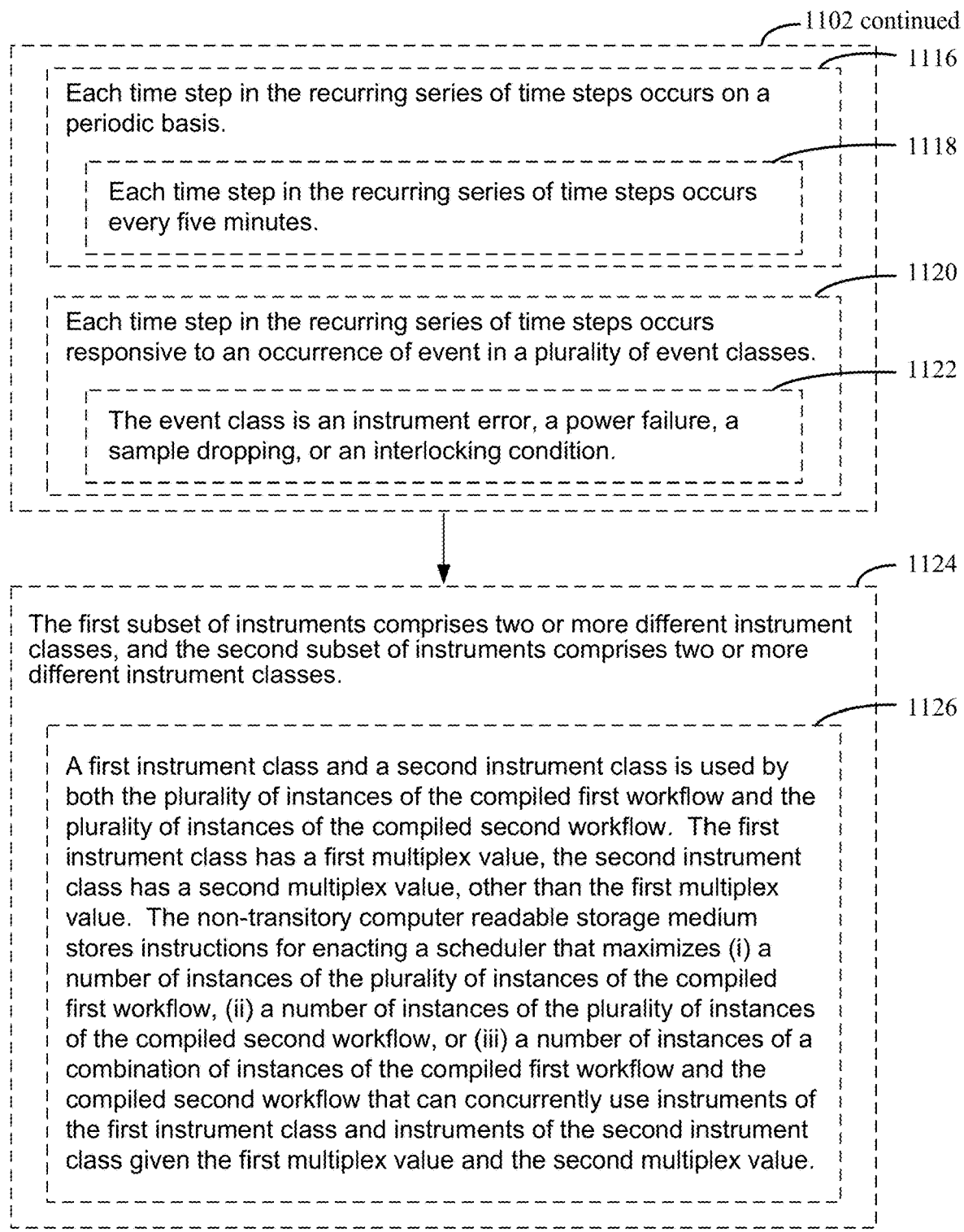

Referring to blocks 1008 through 1012 of FIG. 3A, the method further requires obtaining, via the one or more peripheral devices (e.g., keyboard 28 of FIG. 1), a first plurality of organic engineering targets. In some embodiments, such as automating workflows in a biological foundry, each organic engineering target in the first plurality of organic engineering targets is a plurality of reagents of nucleic acid components. In some embodiments, each organic engineering target in the first plurality of organic engineering targets is an assembly of nucleic acid components. For instance, in some embodiments, each organic engineering target in the first plurality of organic engineering targets is a plasmid, and the nucleic acid components are predetermined promoters, repressors, stop codon, and exons. In some embodiments, each organic engineering target in the first plurality of organic engineering targets is a different predetermined nucleic acid with a different predetermined nucleic acid sequence. In some embodiments, each organic engineering target in the first plurality of organic engineering targets is a different predetermined ribonucleic acid (mRNA) with a different predetermined nucleic acid sequence. In some embodiments, each organic engineering target in the first plurality of organic engineering targets is a different predetermined deoxyribonucleic acid (DNA) with a different predetermined nucleic acid sequence. In some embodiments, each organic engineering target in the first plurality of organic engineering targets is a different predetermined polymer. In some embodiments, each organic engineering target in the first plurality of organic engineering targets is a different predetermined peptide. In some embodiments, each organic engineering target in the first plurality of organic engineering targets is a different predetermined protein.

In some embodiments, each organic engineering target in the first plurality of organic engineering targets comprises a different heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. (A-B-A-B-B-A-A-A-A-B-B-B)$_1$). Additional examples of copolymers are statistical copolymers in which the sequence of monomer residues in the copolymer follows a statistical rule. If the probability of finding a given type monomer residue at a particular point in the chain is equal to the mole fraction of that monomer residue in the chain, then the polymer may be referred to as a truly random copolymer. See, for example, Painter, 1997, Fundamentals of Polymer Science, CRC Press, 1997, p 14, which is hereby incorporated by reference herein in its entirety. Still other examples of copolymers that may be evaluated using the disclosed systems and methods are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, each organic engineering target in the first plurality of organic engineering targets comprises a plurality of polymers, where the respective polymers in the plurality of polymers do not all have the same molecular weight. In such embodiments, the polymers in the plurality of polymers fall into a weight range with a corresponding distribution of chain lengths. In some embodiments, the polymer is a branched polymer molecular system comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, Polymer physics, Oxford; New York: Oxford University Press. p. 6, which is hereby incorporated by reference herein in its entirety.

In some embodiments, each organic engineering target in the first plurality of organic engineering targets comprises a polypeptide. As used herein, the term "polypeptide" means two or more amino acids or residues linked by a peptide bond. The terms "polypeptide" and "protein" are used interchangeably herein and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

In some embodiments, each organic engineering target in the first plurality of organic engineering targets comprises a polypeptide having any number of posttranslational modifications. Thus, a polypeptide includes those that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, each organic engineering target in the first plurality of organic engineering targets comprises an organometallic complex. An organometallic complex is chemical compound containing bonds between carbon and metal. In some instances, organometallic compounds are distinguished by the prefix "organo-"e.g. organopalladium compounds. Examples of such organometallic compounds include all Gilman reagents, which contain lithium and copper. Tetracarbonyl nickel, and ferrocene are examples of organometallic compounds containing transition metals. Other examples include organomagnesium compounds like iodo(methyl)magnesium MeMgI, diethylmagnesium ($Et_2Mg$), and all Grignard reagents; organolithium compounds such as n-butyllithium (n-BuLi), organozinc compounds such as diethylzinc ($Et_2Zn$) and chloro(ethoxycarbonylmethyl)zinc ($ClZ_nCH_2C(=O)OEt$); and organocopper compounds such as lithium dimethylcuprate ($Li^+[CuMe_2]^-$). In addition to the traditional metals, lanthanides, actinides, and semimetals, elements such as boron, silicon, arsenic, and selenium are considered form organometallic compounds, e.g. organoborane compounds such as triethylborane ($Et_3B$).

In some embodiments, each organic engineering target in the first plurality of organic engineering targets comprises two different types of polymers, such as a nucleic acid bound to a polypeptide. In some embodiments, the polymer includes two polypeptides bound to each other. In some embodiments, the polymer under study includes one or more metal ions (e.g. a metalloproteinase with one or more zinc atoms) and/or is bound to one or more organic small molecules (e.g., an inhibitor). In such instances, the metal ions and or the organic small molecules may be represented as one or more additional particles $p_i$ in the set of $\{p_1, \ldots, p_K\}$ particles representing the native polymer.

In some embodiments, each organic engineering target in the first plurality of organic engineering targets comprises a protein. The basic structural elements of proteins are well-known in the art. Nonterminal amino acids typically have the structure —NH—$C^\alpha$HR—CO—, where R represents an amino acid side chain as is known in the art. Atoms such as N, $C^\alpha$, $C^\circ$ and O that are not in the sidechain represent backbone atoms. Atoms of the sidechain, especially the heteroatoms of the sidechain, are referred to as "terminal" atoms. Thus, terminal atoms include $C^\beta$ in alanine, $S^\gamma$ in cysteine, and $N^{\epsilon 1}$ and $C^{\eta 1}$ in tryptophan, for example. Such terminal atoms can be unique. C-alpha or $C^\alpha$ is the carbon atom in the center of each amino acid. The protein backbone includes N, C-alpha, C and O atoms. The backbone dihedral angles of proteins are called $\phi$ (phi, involving the backbone atoms C'—N—$C^\alpha$—C'), $\psi$ (psi, involving the backbone atoms N—$C^\alpha$—C'—N) and $\omega$ (omega, involving the backbone atoms $C^\alpha$—C'—N—$C^\alpha$). Thus, $\phi$ controls the C'—C' distance, $\psi$ controls the N-N distance and o controls the $C^\alpha$—$C^\alpha$ distance. The planarity of the peptide bond usually restricts o to be 180° (the typical trans case) or 0° (the rare cis case). The sidechain dihedral angles tend to cluster near 180°, 60°, and −60°, which are called the trans, gauche$^+$, and gauche$^-$ conformations. The choice of sidechain dihedral angles is affected by the neighbouring backbone and sidechain dihedrals. A Ramachandran map (Ramachandran, Ramakrishnan, and Sasisekharan 1963) is a representation of the stereochemically allowed protein backbone geometries as a function of their variable torsion angles.

There are different levels of describing the structure of a protein. Primary structure refers to the linear sequence of amino acids that make up the polypeptide chain. The bond between two amino acids is a peptide bond. The sequence of amino acids determines the positioning of the different R groups relative to each other. This positioning determines the way that the protein folds and the final structure of the molecule. The secondary structure of protein molecules refers to the formation of a regular pattern of twists or kinks of the polypeptide chain. The regularity is due to hydrogen bonds forming between the atoms of the amino acid backbone of the polypeptide chain. The two most common types of secondary structure are called the "α-helix" and "β-pleated sheet". Tertiary structure refers to the three dimensional globular structure formed by bending and twisting of the polypeptide chain. This process often means that the linear sequence of amino acids is folded into a compact globular structure. The folding of the polypeptide chain is stabilized by multiple weak, noncovalent interactions. These interactions include hydrogen bonds, electrostatic interactions, hydrophobic interactions, and sometimes covalent bonds. Quaternary structure refers to the fact that some proteins contain more than one polypeptide chain, adding an additional level of structural organization: the association of the polypeptide chains. Each polypeptide chain in the protein is called a subunit. The subunits can be the same polypeptide chain or different ones. For example, the enzyme P-galactosidase is a tetramer, meaning that it is composed of four subunits, and, in this case, the subunits are identical—each polypeptide chain has the same sequence of amino acids. Hemoglobin, the oxygen carrying protein in the blood, is also a tetramer but it is composed of two polypeptide chains of one type (141 amino acids) and two of a different type (146 amino acids).

In some embodiments, each organic engineering target in the first plurality of organic engineering targets comprises a chemical compound that satisfies the Lipinski rule of five criteria. In some embodiments, the chemical compound is an organic compounds that satisfies two or more rules, three or more rules, or all four rules of the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a LogP under 5. The "Rule of Five" is so called because three of the four criteria involve the number five. See, Lipinski, 1997, Adv. Drug Del. Rev. 23, 3, which is hereby incorporated herein by reference in its entirety. In some embodiments, the organic engineering target satisfies one or more criteria in addition to Lipinski's Rule of Five. For example, in some embodiments, the test perturbation is a compound with five or fewer aromatic rings, four or fewer aromatic rings, three or fewer aromatic rings, or two or fewer aromatic rings.

As such, in the context of biological engineering, an organic engineering target is one of the objectives of a research and development project that defines the desired biological trait to be achieved. The organic engineering target can be either quantitative or qualitative. For example, in one embodiment, an organic engineering target(s) can be a genetic configuration for a biosynthetic pathway that produces more compound of interest than a current level. In another embodiment, the organic engineering target(s) is a genetic configuration for a microbial host that has a tolerance to an inhibitor over X mg/L. Additionally, in some embodiments an organic engineering target is a polynucleotide or nucleic acid sequence. The terms "polynucleotide" and "nucleic acid sequence" interchangeably refer to a polymer composed of nucleotide units as would be understood by one of skill in the art. Preferred nucleotide units include but are not limited to those comprising adenine (A), guanine (G), cytosine (C), thymine (T), and uracil (U). Useful modified nucleotide units include but are not limited to those comprising 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. Polynucleotides include naturally occurring nucleic acids, such as deoxyribonucleic acid ("DNA") and ribonucleic acid ("RNA"), as well as nucleic acid analogs. Nucleic acid analogs include those that include non-naturally occurring bases, nucleotides that engage in linkages with other nucleotides other than the naturally occurring phosphodiester bond or that include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like.

Furthermore, in some embodiments an organic engineering target refers to a polynucleotide sequence that can be assembled together to form an "engineered nucleic acid construct" using the methods of polynucleotide assembly described herein. A "component polynucleotide," alternately referred to as "bits" herein, refers to any isolated or isolatable molecule of DNA. Useful examples include but are not limited to a protein-coding sequence, reporter gene, fluorescent marker coding sequence, promoter, enhancer, terminator, intron, exon, poly-A tail, multiple cloning site, nuclear localization signal, mRNA stabilization signal, selectable marker, integration loci, epitope tag coding sequence, degradation signal, or any other naturally occurring or synthetic DNA molecule. In some embodiments, the DNA segment is of natural origin. Alternatively, a DNA segment can be completely of synthetic origin, produced in vitro. Furthermore, a DNA segment can comprise any combination of isolated naturally occurring DNA molecules, or any combination of an isolated naturally occurring DNA molecule and a synthetic DNA molecule. For example, a DNA segment may comprise a heterologous promoter operably linked to a protein coding sequence, a protein coding sequence linked to a poly-A tail, a protein coding sequence linked in-frame with an epitope tag coding sequence, and the like. Working examples of various organic engineering targets to described infra (1008, 1010, 1012).

Figure 6A:
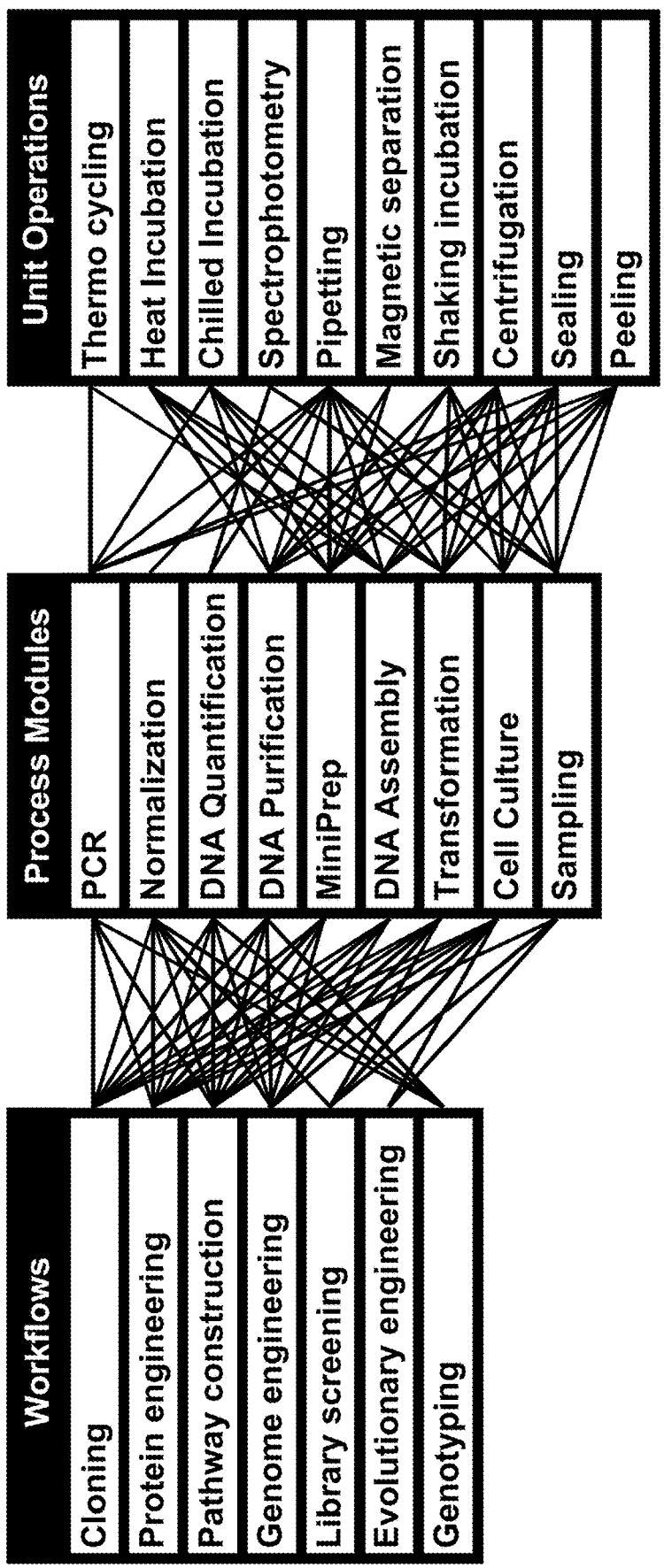
FIGS. 6A and 6B illustrate a breakdown of unit operations of an iBioFAB system according to an embodiment of the present disclosure.

Referring to block 1014 of FIG. 3A, following selection of the first plurality of engineering targets, the method includes assigning the first plurality of organic engineering targets to a first uncompiled workflow. In general, a workflow is a generalized laboratory process that includes a series of unit operations to achieve an engineering target. Workflows can be applied to different sample, or organic engineering target, batches with different parameter sets. The first uncompiled workflow is configured to produce the first plurality of organic engineering targets, and the first uncompiled workflow is associated with a first subset of process modules in a plurality of process modules. A process module is a generalized laboratory process that consists of a series of unit operations. In most cases, a process module is routinely performed in workflows and shared by research projects. When developing workflows, process modules can be called from a library (e.g., process module library 54) and configured with an appropriate parameter set to simplify and standardize programming practice. Process modules can be nested to form complex workflows. For instance, referring to FIG. 6A, an exemplary evolutionary engineering workflow is associated with a subset of process modules including cell culture and sample, whereas a library screening workflow is associated with normalization, transformation, cell culture, and sample process modules. Each respective process module in the plurality of process modules is associated with a different subset of unit operation definitions in a plurality of unit operation definitions. Each respective unit operation definition in the plurality of unit operation definitions is independently associated with a corresponding time interval as well as each respective unit operation definition in the plurality of unit operations is independently associated with a first subset of instruments in a plurality of instruments. In the context of biological engineering, a unit operation is a basic step in a laboratory process. Unit operations involve a physical or chemical procedure on the samples conducted by a single instrument. In scheduling, a unit operation or action is a largest inseparable unit that may consist of a sequence of micro steps (e.g. no other procedure or delay can be cut into these micro steps). As shown in FIG. 6A, an exemplary process module "normalization" includes the unit operation(s) pipetting, whereas the process module "DNA quantification" includes unit operations "spectrophotometry" and "pipetting" (1014).

Figure 18:
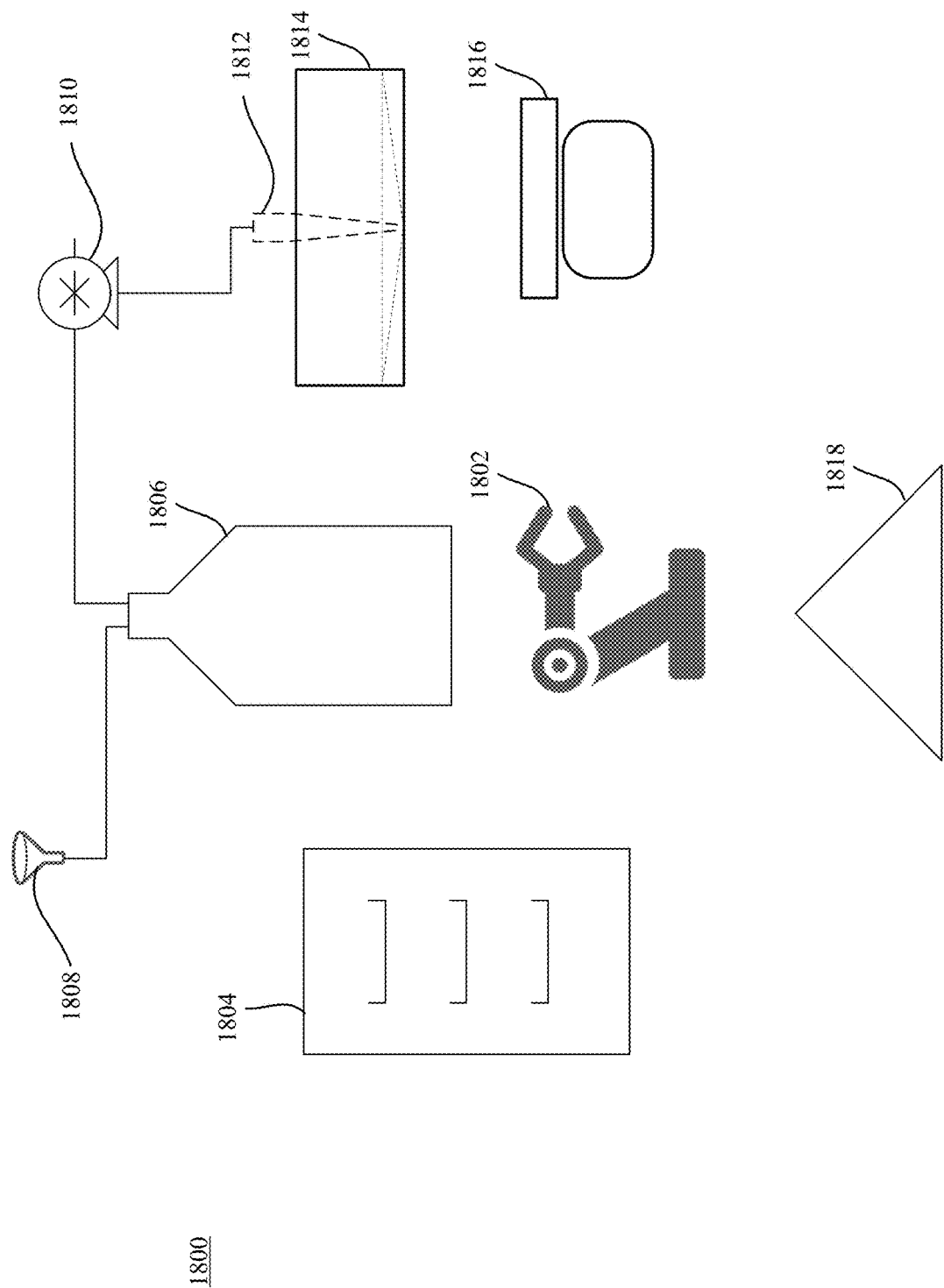
FIG. 18 illustrates an automated centrifuge handling system according to an embodiment of the present disclosure.

Subsets of instruments include but are not limited to systems and/or devices that perform unit operations. For instance, referring to FIG. 18, in some embodiments a subset of instruments includes an automated centrifuge handling system 1800. The automated centrifuge handing system 1800 includes a robotic arm that operates various instruments of the system and handles samples.

In some embodiments, the robotic arm is a Cartesian robotic arm. In some embodiments, the robotic arm is an articulated robotic arm, including four axis robotic arms, five-axis robotic arms, six-axis robotic arms, and seven-axis robotic arms. For instance, in some embodiments the robotic arm is a Kuka KR 3 R540 AGILUS robotic arm or a Kuka KR 1000 titan F robotic arm. In some embodiments, the robotic arm is a selective compliance assembly robot arm (SCARA). In some embodiments, the robotic arm is the previously described transporter. In some embodiments, the robotic arm is a conveyer belt, a linear transfer stage, a gantry, or an elevator.

The robotic arm 1802 transfers samples from a storage device 1804 to a multi-well plate, or similar device which is utilized by a centrifuge 1818 such as a vial, a bottle, a screw-top tube, a snap-top tube, an open tube, a flip-top tube, etc. Once the multi-well plate, or in some embodiments a multitude of multi-well plates, is filled, a mass of each multi-well plate is determined. In some embodiments, these multi-well plates form a first set of multi-well plates (e.g., the multi-well plates of a first operation of the centrifuge). A number of multi-well plates in a set of multi-well plates is determined by a type and size of the centrifuge 1818. For instance, in some embodiments the centrifuge is configured to hold one multi-well plate, is configured to hold two sets of multi-well plates, three sets of multi-well plates, four sets of multi-well plates, five sets of multi-well plates, etc. A number of multi-well plates and a type of multi-well plate is dictated by a type of centrifuged utilized in the present disclosure. Accordingly, in some embodiments the multi-well plates are 6-well plates, are 12-well plates, are 24-well plates, are 48 well-plates, are 96-well plates, are 384-well plates, or are 1536-well plates. Similarly, in some embodiments these plates are formed with a U-shaped bottom end portion, with a V-shaped bottom end portion, or with a flat-shaped bottom end portion. For instance, in some embodiments the multi-well plates are Fisherbrand 96-well plates No.: N95029340FP; are Thermo Fisher Scientific Nunc U96 Microwell Plates, PS; are Thermo Fisher Scientific Nunc V96 Microwell Plates, Clear, PS; are CELL-TREAT 96 Well Non-Treated Microplates, F-Bottom, Clear, Sterile; are iSci d75-712 Microplates; or are Corning 3370 Plates, 96 well, PS, Flat, 100/cs, Clear. However, the present disclosure is not limited thereto.

Centrifuges of the present disclosure include, but are not limited to, small benchtop centrifuges, micro-centrifuges (e.g., a microfuge), high speed centrifuges, or ultra-centrifuges. In some embodiments, the centrifuge is an Eppendorf 5430 Centrifuge R, an Eppendorf 5920 R Centrifuge, a Jouan Robotics GR4 Auto Centrifuge, or a Thermo Fisher Scientific Heraeus Multifuge X3 Series Centrifuge. However, the present disclosure is not limited thereto.

Each multi-well plate has a corresponding counter balance 1814, which ensures the centrifuge 1818 is stable during operation. Without human intervention, a mass of each counter balance 1814 is adjusted to be equal to the mass of the corresponding multi-well plate. This adjustment is accomplished by pumping fluid (e.g., water, mineral oil, aqueous solutions, organic solutions, etc.) from a container 1806, which includes a pressure regulator 1808, or in some embodiments an air intake, to the counter balance 1814 via a pump 1810. In some embodiments, the pump 1808 is a siphon. Attached to the pump is a nozzle, which either dispenses fluid from the container 1806 to the counter balance 1814 or draws fluid from the counter balance 1814 to the container 1806. In some embodiments, a bottom end portion of each counter balance 1814 is formed with a slope to allow the for pooling of the fluid of the container 1806 in the counter balance 1814. The pooling of the fluid in the counter balance 1814 ensures that the entire fluid can be completely removed from the counter balance. In some embodiments, the slope is formed as a V-shape, as a U-shape, or as a slant. Moreover, in some embodiments each counter balance 1814 is configured to have a relatively low empty mass (e.g., a few grams) to allow for higher accuracy and precision in determining a mass of the counter balance while minimizing energy consumption required to move the counter balance. Each counter balance holds a high internal volume or capacity to ensure that sufficient mass can be added therein, and a high tolerance to centrifugal action to ensure that the counter balance survives operating in the centrifuge.

In some embodiments, a multi-well plate and the corresponding counter balance 1814 are disposed on a balance 1816, or scale, in order to ensure that the masses of the multi-well plate and the corresponding counter balance 1814 are equal. This also ensure that the measurements are conducted simultaneously. Likewise, in some embodiments the mass of the multi-well plate is determined using the scale 1816 and stored for later use. The multi-well plate is disposed into the centrifuge 1818 by the robotic arm 1802. The mass of the corresponding counter balance is then determined the scale 1816, and adjusted in accordance with the stored mass of the multi-well plate. In some embodiments, the mass of the corresponding counter balance is stored for later use, such that the adjustment of the mass of the counter balance in a later operation of the centrifuge does not require as much of an adjustment (e.g., adjusting a previous mass of 20 g to 21 g instead of adjusting a mass of 0 g to 21 g). Once the mass of the multi-well plate and the mass of the corresponding counter balance 1814 are equal, and both devices are disposed in the centrifuge 1818, the centrifuge is operated.

In some embodiments, after operating the centrifuge 1818 with the first set of multi-well plates and corresponding counter balances 1814, a second set of multi-well plates are prepared accordingly. In some embodiments, the second set of multi-well plates is the first set of multi-well plates, which were previously sterilized. A mass of each multi-well plate in this second set is determined, and masses of corresponding counter balances 1814, are determined in accordance with the above descriptions of the first set of multi-well plates (e.g., determined simultaneously or consecutively). Accordingly, the utilized automated centrifuge system of the present disclosure enables the centrifuge 1818 to be fully operated (e.g., multi-well plates are produced and masses of counter balances are determined and adjusted) without human intervention.

Workflows can include processes for pathway construction, expression fine-tuning, genome editing, and cell adaptation but the present disclosure is not limited thereto. Other workflows include cloning, evolutionary organic engineering, genome organic engineering, genotyping, library screening, pathway construction, and protein organic engineering (1016).

Examples of process modules includes, but are not limited to, cell culture, DNA assembly, DNA purification, DNA quantification, normalization, polymerase chain reaction (PCR), sample preparation, sampling, sample analysis, protein extraction, and transformation; however, the present disclosure is not limited thereto. For instance, in other embodiments, such as a surgical pathology system or a toxicology system, process modules can various from system to system (1018, 1020).

Examples of unit operations include, but are not limited to, centrifugation, chilled incubation, heated incubation, magnetic separation, peeling, pipetting, dispensing, sealing, shaking incubation, spectrophotometry, chromatography, mass spectrometry, microscopic imagining, electrophoresis, electroporation, clone separation, colony selection, and thermal cycling. Other unit operations include freezing, purifying, heating, cryogenic storage, sonication, milling, sterilizing, and the like (1022, 1024).

Figure 6B:
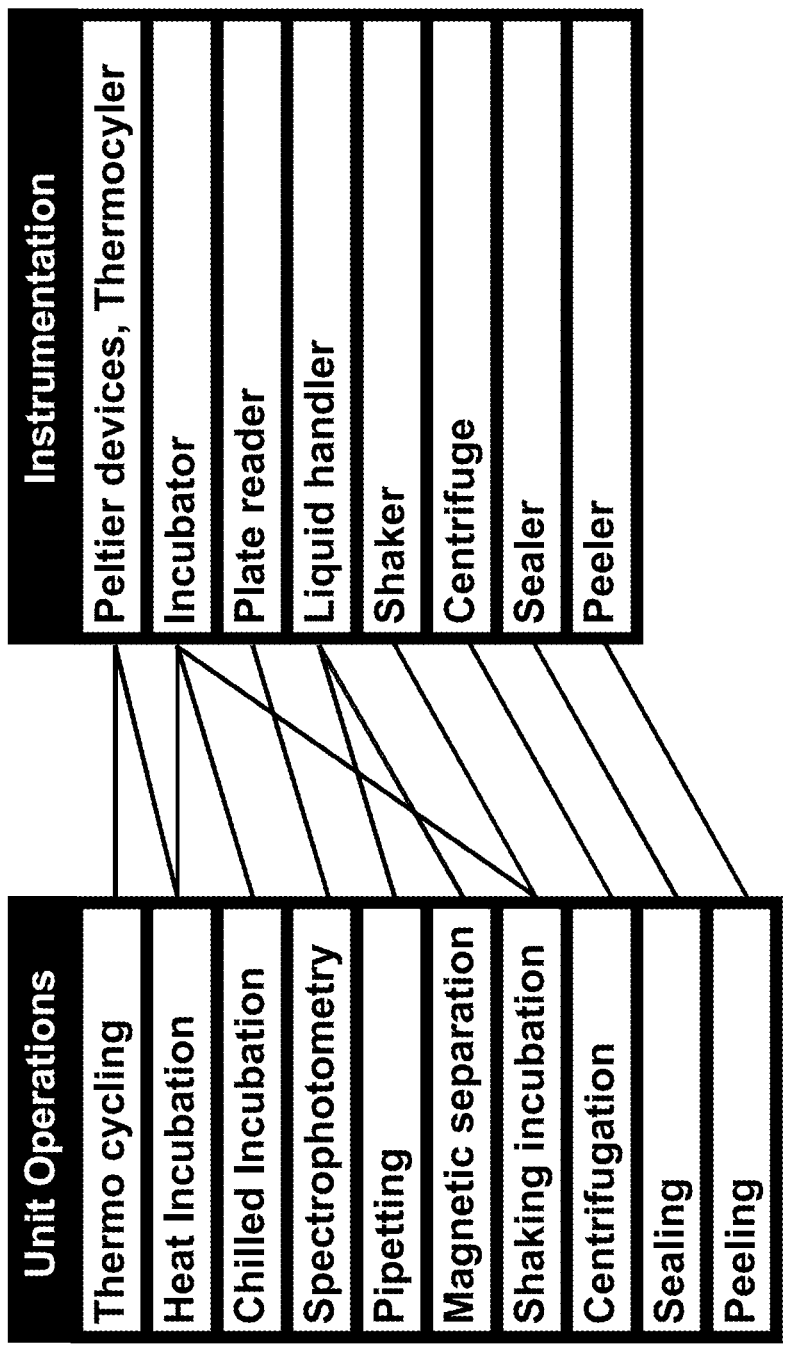
Figure 6C:
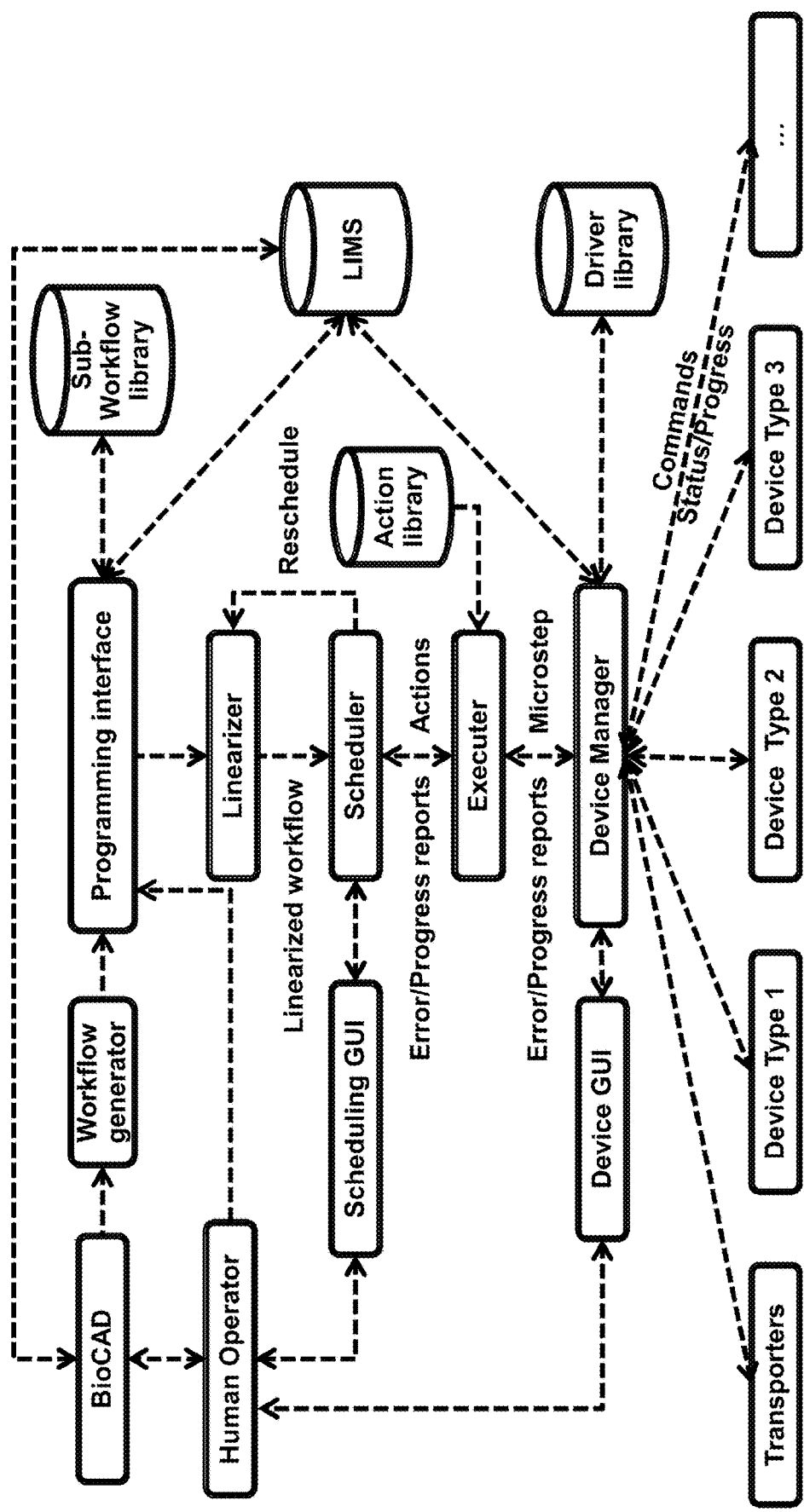
FIGS. 6C and 6D illustrate various control hierarchies of an iBioFAB system according to embodiments of the present disclosure.
Figure 6D:
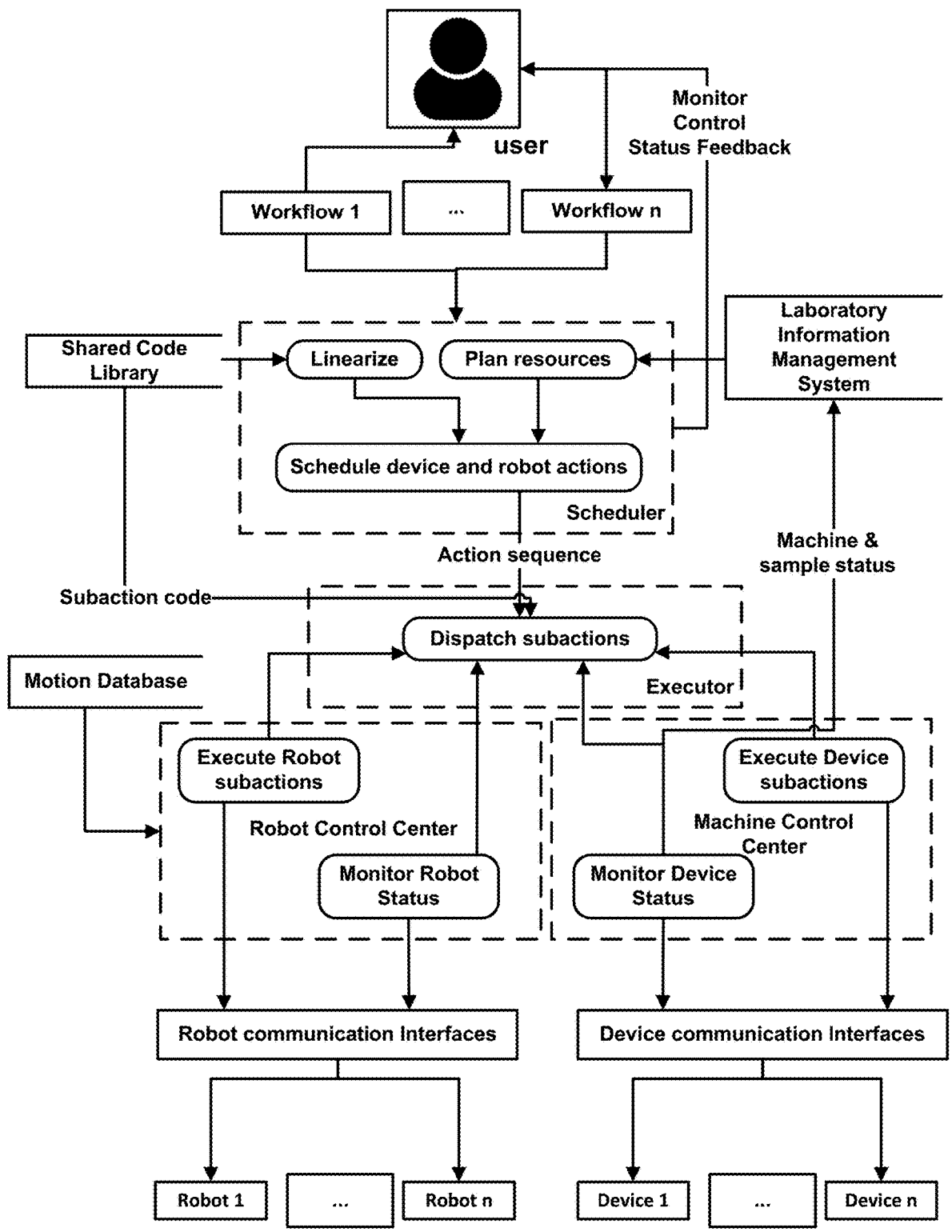

An instrument is a device that conducts a specific function or functions in the automated system. In most cases, an instrument is a device that conducts a unit operation or unit operations to samples or organic engineering targets. Examples of instruments include, but are not limited to, a centrifuge, a Peltier temperature controller, an incubator, a shaking incubator, a magnetic separator, a peeler, a liquid handling robot, a dispenser, a sealer, a plate reader, a liquid chromatography system, a gas chromatography system, a mass spectrometry system, a microscope, a electrophoresis device, a electroporation device, a clone separation device, a clone selection device, and a thermal cycler. FIG. 6B depicts relations between exemplary unit operations and a plurality of instruments. Other instruments include, but are not limited to, fume hoods, glove boxes, stability chambers, sterilizers, mills, burners, water baths, coolers, and similar instruments which are found in scientific laboratories and biological foundries (1026, 1028).

Figure 13:
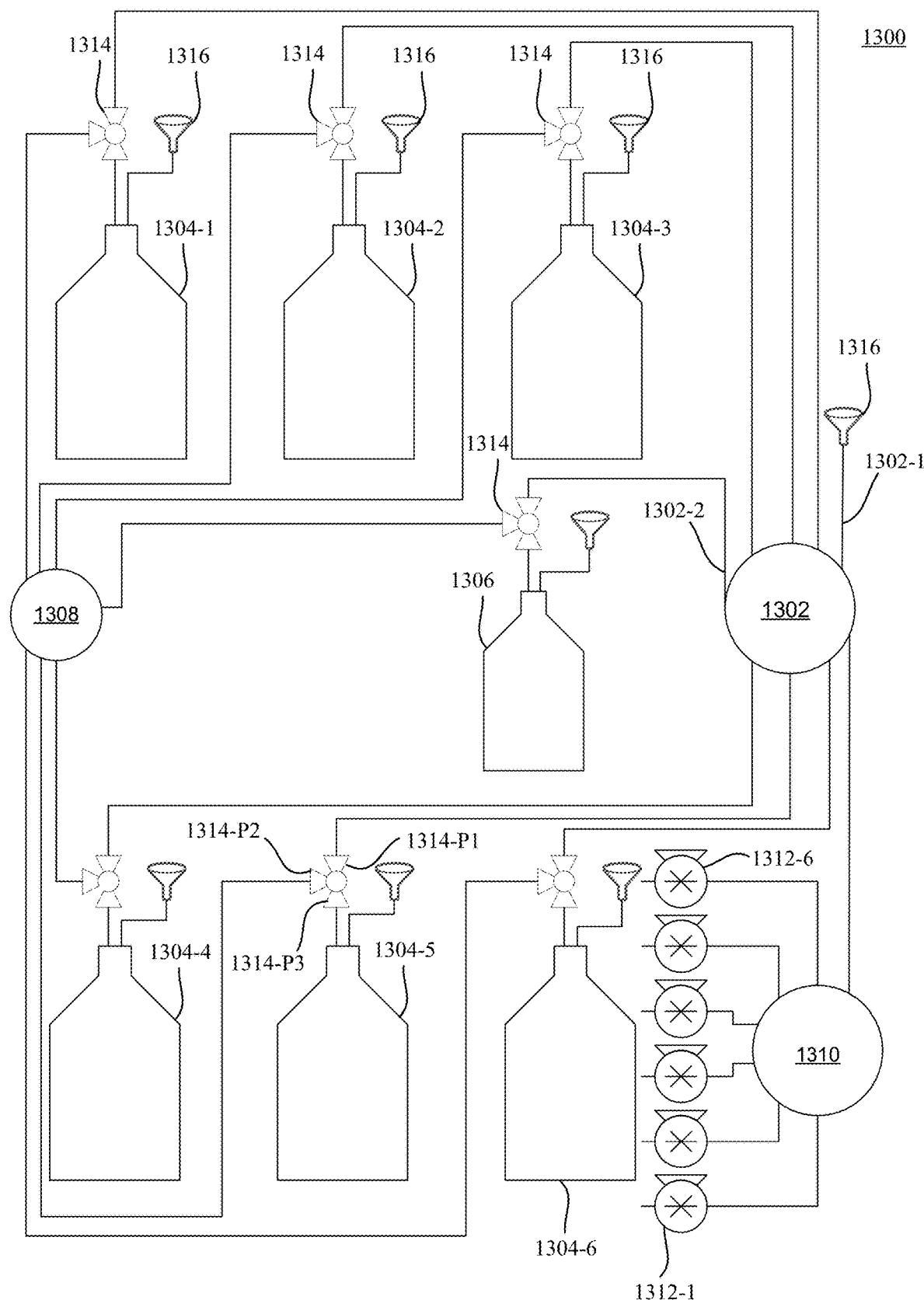
FIG. 13 illustrates a fluid management system according to an embodiment of the present disclosure.

For instance, referring to FIG. 13, in some embodiments an instrument includes a reagent handling device 1300. The reagent handling device 1300 of the present disclosure in configured to store and dispense a variety of reagents (e.g., liquids and/or gases reagents) for prolonged periods of time. For instance, if a reagent is honey, which has an infinite expiration date, the reagent handling device could store and dispense the honey as long as there is power supplied to the robot 1300.

The reagent handling device 1300 of FIG. 13 includes a primary switch 1302 (e.g., a primary valve) which is configured as a master control of the robot. Control of the reagent handling device 1300 is conducted through one or more pumps (e.g., a multitude of individual pumps, a multichannel pump, or a combination thereof), that allows for control of a dispensing cycle and a sterilization cycle. The primary switch 1302 is programmatically controlled to allow for automated operation of the robot 1300 in a workflow. However, in some embodiments, the primary switch 1302 is controlled manually and/or the primary switch 1302 is a plurality of selective valves. In some embodiments, the primary switch 1302 includes at least a first port 1302-1 and a second port 1302-2, which are dedicated ports dedicated to various cycles of the reagent handling device 1300, which will be described in more detail infra.

The dispensing cycle includes a dispense manifold 1310 and a reagent container portion. An inlet of the dispense manifold 1310 is coupled to an outlet of the primary switch 1302, allowing reagents to flow or traverse from the reagent container portion to the dispense manifold. An outlet of the dispense manifold 1310 is coupled to one or more dispensers 1312. The present illustration depicts six dispensers (e.g., dispenser 1312-1, dispenser 1312-2, ..., dispenser 1312-6). However, the present disclosure is not limited thereto. For instance, in some embodiments there exists a one-to-one relation between reagents and dispensers 1312 of the reagent handling device 1300. In some embodiments, there exists multiple dispensers 1312 in order to allow each reagent and combinations thereof to be dispensed through a dedicated dispenser 1312.

Furthermore, in the present illustration there is one connection from the primary switch to the dispense manifold. In some embodiments, there are multiple connections from the primary switch to the dispense manifold. Multiple connections for a dedicated connection to the dispense manifold 1302 for each reagent that the reagent handling device 1300 is configured to dispense. Each coupling or connection of the reagent handling device 1300 is a tubing that allows for a sterile for of reagent therein. In some embodiments, these connections are removable.

The reagent container portion includes a variety of reagent containers 1304 (e.g., reagent container 1304-1, reagent container 1304-2, ..., reagent container 1304-6, ... reagent container 1304-i), each storing a unique reagent. In some embodiments, the reagent containers are formed of a sterile material, are sealed from an external environment, are resistance to electromagnetic radiation (e.g., ultraviolet light, visible light, infrared light, etc.), or a combination thereof. Moreover, there is no maximum or minimum number of reagent containers 1304 that are utilizable by the reagent handling device 1300, since the robot is configured to store and dispense any number of reagents.

In some embodiments, each reagent container 1304 is coupled to a pressure regulator 1316. The pressure regulator 1316 allows for a control of pressure within the reagent container in order to either increase a pressure of the reagent container or decrease the pressure. Control of pressure within the reagent container 1304 enables displacement of an internal reagent with air, or another fluid. In some embodiments, the pressure regulator 1316 includes an air filter that prevents contamination of the reagent container 1304. Air filters should be appropriately selected in relation to prevent microbial and particulate contaminants from entering the reagent container. In some embodiments, the pressure regulator 1316 includes a check valve, which prevents evaporation and/or vapor release of a reagent in the reagent container 1304. Furthermore, each reagent container 1304 is coupled to a valve 1314 (e.g., a selection valve), which controls a flow of material to/from the reagent container and the primary valve 1302 or a wash manifold 1308.

The sterilization cycle includes the wash manifold 1308 and a sterilization container 1306. The wash manifold 1308 controls a flow of a sterilization fluid from the sterilization container 1306 to each reagent container 1304. In some embodiments, the sterilization container is a reagent container 1304 that is dedicated to storing the sterilization fluid. Sterilization fluids include liquid chemical sterilants, disinfectants (e.g., high level disinfectants), distilled water, detergents, and similar cleaning solutions such as a buffer. In some embodiments, the sterilization fluid is a fluid which thermally sterilizes, such as steam. In some embodiments, the sterilization fluid is a low temperature gas, vapor, or plasma. The sterilization container 1306 is configured in a similar manner as the reagent container 1306, in that a valve 1314 and a pressure regulator 1316 are coupled thereto.

While describing the cycles of the liquid handling robot 1300, a first position of a valve 1314, hereinafter "P1," refers to a valve position 1314-P1 as shown and described by exemplary reagent container 1304-5 of FIG. 13; a second position of a valve 1314, hereinafter "P2," refers to valve position 1314-P2 as shown and described by exemplary reagent container 1304-5 of FIG. 13; a third position of a valve, hereinafter "P3," refers to valve position 1314-P3 as shown and described by exemplary reagent container 1304-5 of FIG. 13.

In some embodiments, the sterilization cycle is a two-part cycle (e.g., a first sterilization cycle and a second sterilization cycle). The first cycle is configured to sterilize select portions of the reagent handling device 1300 that require, or have previously required, attention (e.g., repair or replacement), while the second cycle is configured to sterilize portions of the reagent handling device during automated use of the robot.

In some embodiments, the second cycle is configured to sterilize select portions of the reagent handling device 1300 that were recently dispensed or activated, and purge select portions of the reagent handling device 1300 with air, gas, distilled water, or a similar medium.

While describing the cycles of the liquid handling robot 1300, a first position of a valve 1314, hereinafter "P1," refers to a valve position 1314-P1 as shown and described by exemplary reagent container 1304-5 of FIG. 13; a second position of a valve 1314, hereinafter "P2," refers to valve position 1314-P2 as shown and described by exemplary reagent container 1304-5 of FIG. 13; a third position of a valve, hereinafter "P3," refers to valve position 1314-P3 as shown and described by exemplary reagent container 1304-5 of FIG. 13.

The first sterilization cycle (e.g., an initial sterilization cycle), is conducted by selecting a portion of the reagent handling device 1300 (e.g., reagent container 1304-5) to sterilize. The primary valve 1302 is switched to the selected reagent container, the valve 1314 of the selected reagent container 1304 is switched to P1 and P2 (e.g., P1 open, P2 open, P3 closed), and the valve 1314 of the selection sterilization container 1306 to P2 and P3. This first sterilization cycle allows for, in part, various amounts of sterilization fluid to be dispensed to a variety of dispensers 1312 from the sterilization container 1306 through the wash manifold 1308 to the selected reagent containers 1304.

The second sterilization cycle (e.g., an automated sterilization cycle), is conducted by switching the primary valve 1302 to the second port 1302-2. This second sterilization cycle allows for, in part, various amounts of sterilization fluid to be dispensed to a variety of dispensers 1312 from the sterilization container 1306 through the wash manifold 1308 to the selected dispensers 1304. To purge the primary valve 1302 and the dispenser 1312, the primary valve is switch to port one 1302-1, which allows gas or air to be pumped through portions of the system.

The dispensing cycle is conducted by switching each reagent container 1304 to P1 and P3. The primary valve 1302 is switch to a selected reagent container 1304, which allows a flow of material from the selected reagent container to a predetermined dispenser 1312.

Figures 14A, 14B:
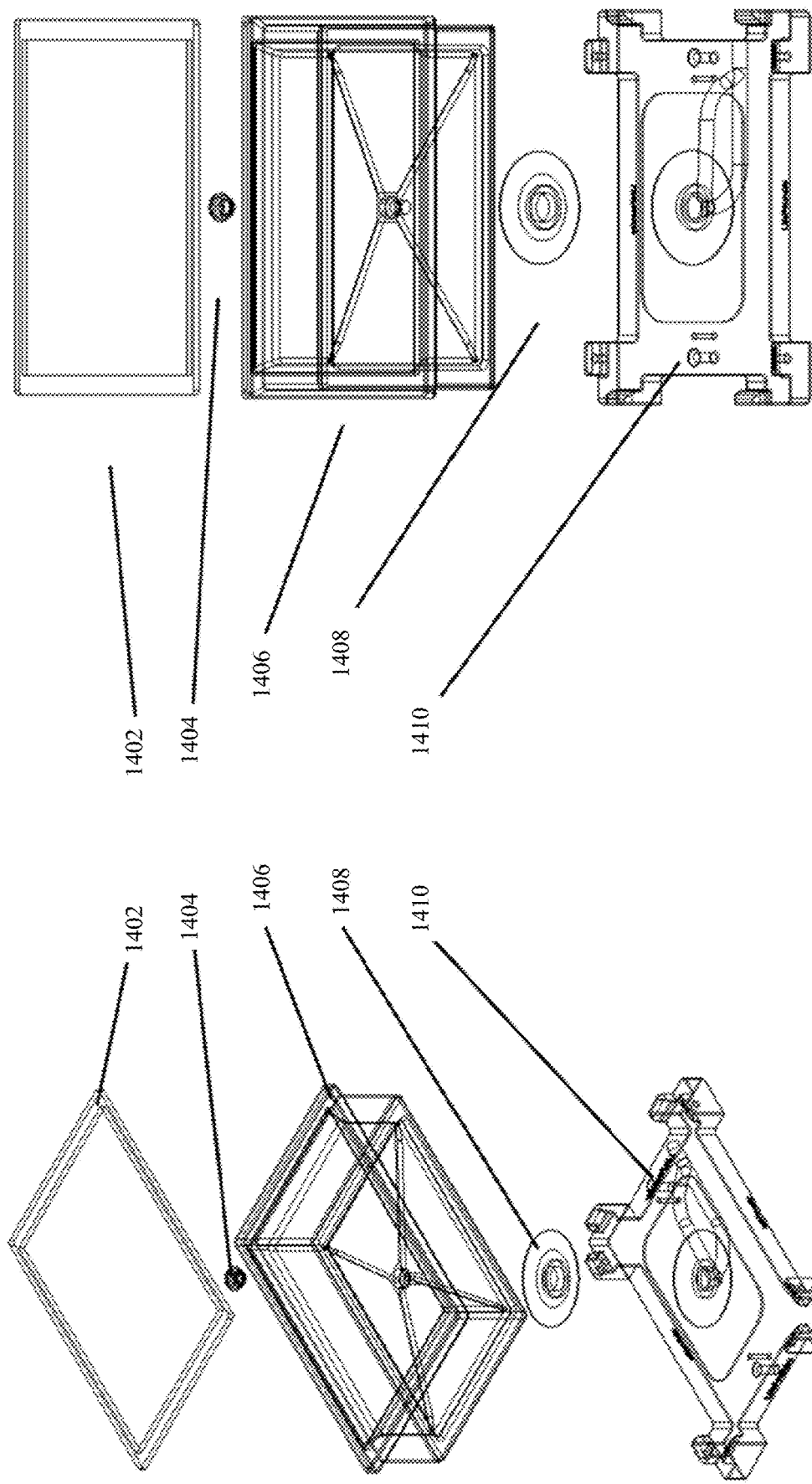
FIGS. 14A, 14B, and 14C illustrate a centrifuge compatible vacuum manifold according to an embodiment of the present disclosure.
Figure 14C:
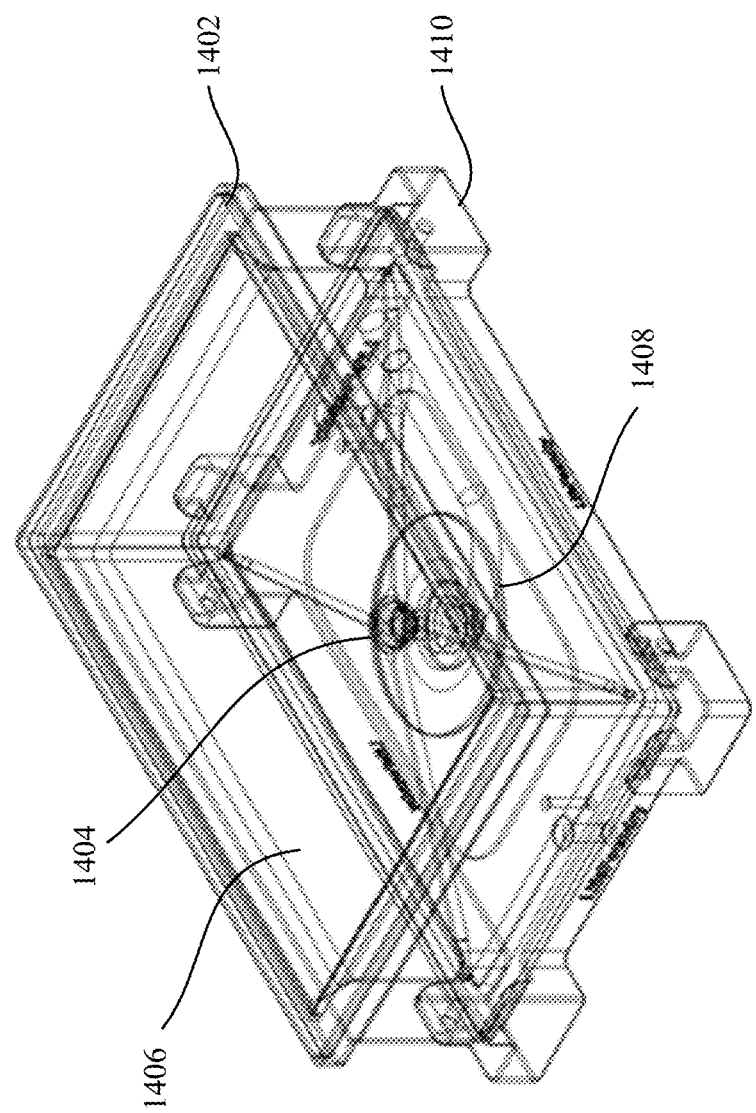

Referring to FIG. 14, in some embodiments the instruments include a centrifuge compatible vacuum manifold 1400. The centrifuge compatible vacuum manifold drives fluid through a resin or a filter column. As illustrated in FIG. 14, in some embodiments the centrifuge vacuum manifold 1400 includes a plate gasket 1402, which seals a portion (e.g., a top end portion) of the manifold 1400. The manifold 1400 also includes a channel plug 1404, which controls and prevents a flow of fluid out of a container body 1406 of the manifold. The container body includes one or more fluid channels formed therein, which guide a flow of fluid towards the channel plug 1404. In some embodiments, the fluid channels are formed with a declined slope on a bottom surface of the container body 1406 to assist a flow of fluid. The channels of the container body 1406 are configured to have a first opening of the container body 1406 be at a lowest point of the container body, to have at least a portion of one or more channels at a higher point than the lowest point of the container body, and have a second opening at an outside portion of the container body 1406 that attaches to an external vacuum. Furthermore, a vacuum coupler gasket 1408 is coupled to the manifold 1400 to seal the manifold to the external vacuum, which rests in a vacuum nest 1410. The vacuum next is removably coupled to the manifold 1400, and supports, or couples to the external vacuum. In some embodiments, the manifold 1400 is configured to have a footprint in accordance with guidelines of the Society for Biomolecular Screening (SBS). ANSI SLAS 1-2004 (R2012)., the contents of which are hereby expressly incorporated by reference. Moreover, in some embodiments the manifold 1400 is configured to have a low profile in order to fit the manifold into a variety of centrifuges and dispensers. The low profile allows the manifold 1400 to couple to centrifuges which may have column arrays attached to thereto. In some embodiments, the vacuum gasket 1408 and the vacuum nest 1410 have chamfered and/or filleted boundary portions to enable a fit and positioning of the container body 1406. As previously described, chamfered and/or filled boundary portions of instruments and components thereof is preferred in order to allow an automated robot to fit trays, multi-well plates, samples, and the like into instruments without yielding a hard collision. For instance, if a tray is misallied by 0.1 mm, and a fillet has a radius larger than this misalignment, than the tray will follow the curve of the fillet and fit into a receptacle. Furthermore, in some embodiments the vacuum gasket 1408 and the vacuum nest 1410 are removably coupled to the container body 1406. In some embodiments, each component of the manifold 1400 is removably coupled, such that the entire manifold can be disassembled into its constituent components. Accordingly, the centrifuge compatible vacuum manifold 1400 of the present disclosure is operable by a robot arm (e.g., robotic arm 1802 of FIG. 18, robotic arm 1902 of FIG. 19), acts as a vacuum manifold, and stores any fluid dripped from a column array until a vacuum is applied.

Figure 15:
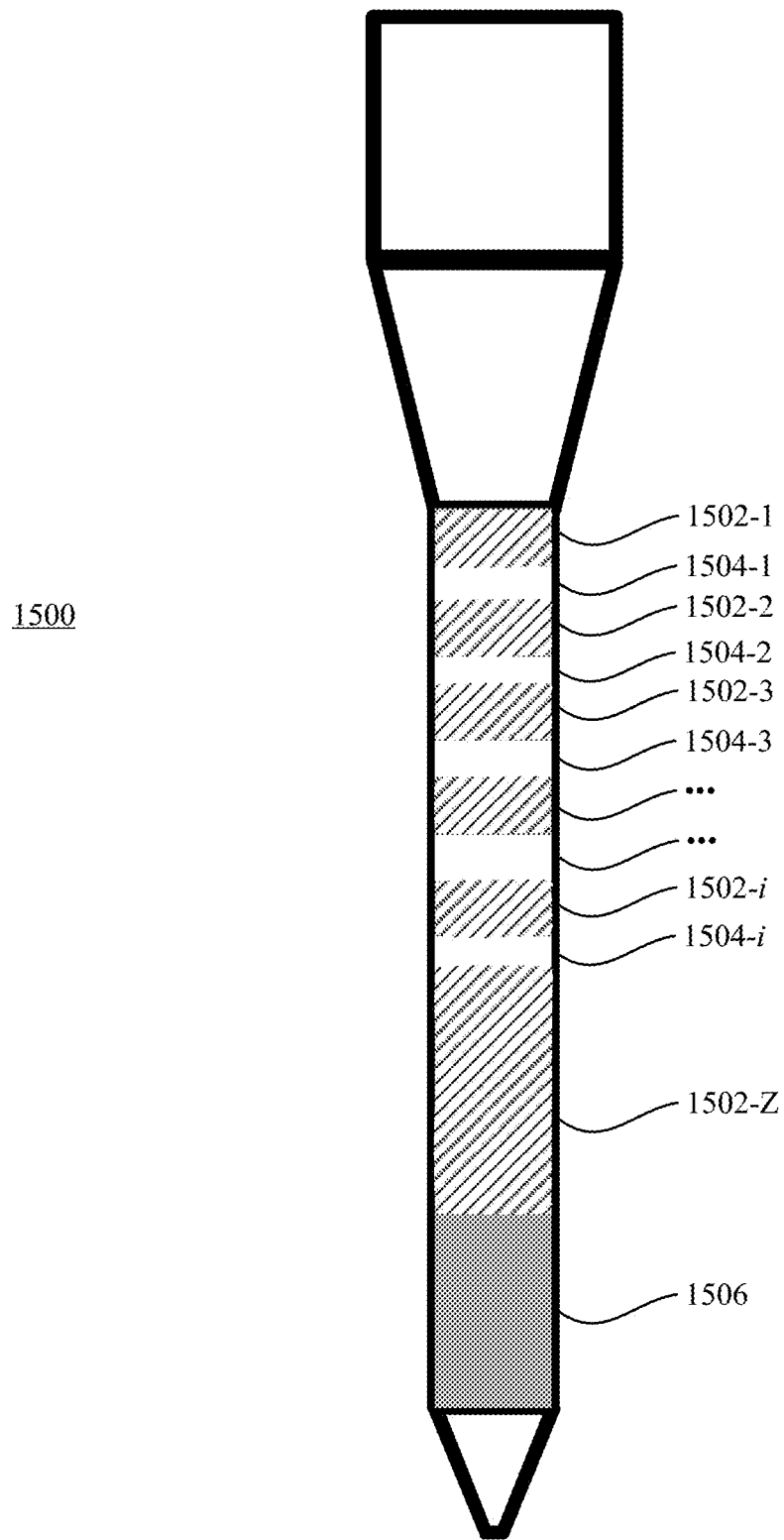
FIG. 15 illustrates a pipette tip according to an embodiment of the present disclosure.
Figure 16B:
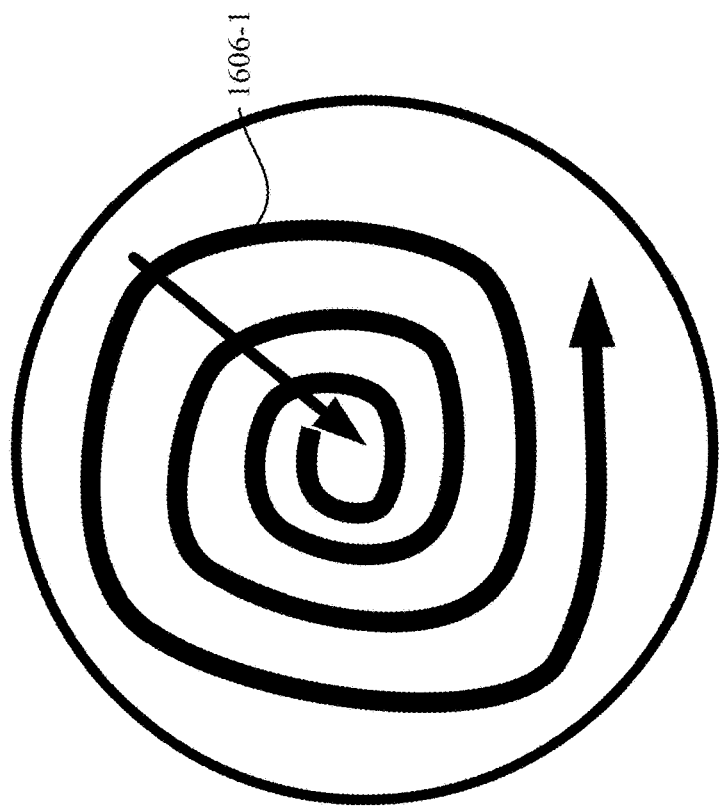
FIGS. 16A and 16B illustrate a dispending pattern and streaking patterning according to an embodiment of the present disclosure.
Figure 16A:
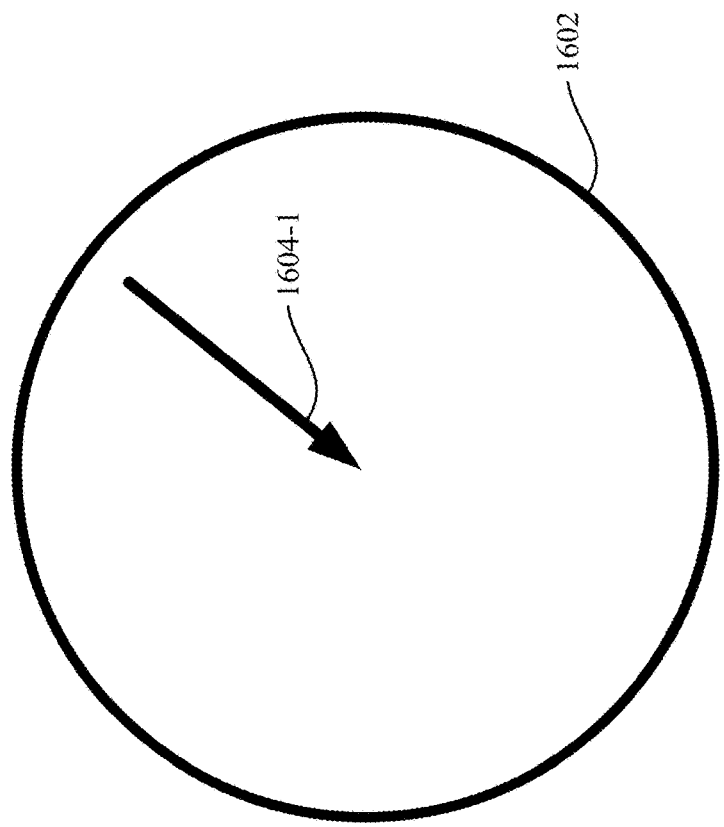
Figure 16D:
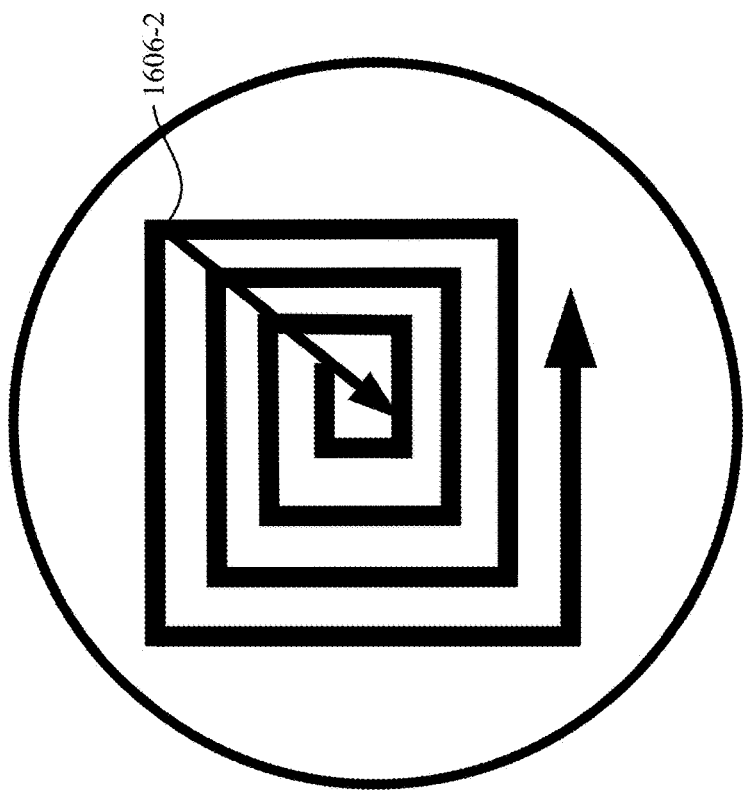
FIGS. 16C and 16D illustrate another dispending pattern and streaking patterning according to an embodiment of the present disclosure.
Figure 16C:
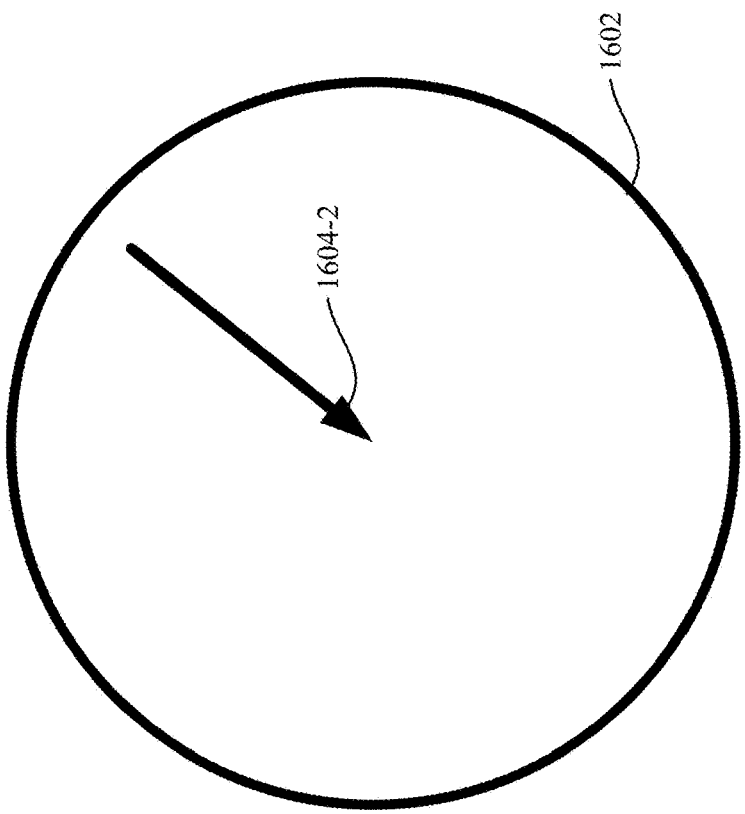
Figure 17B:
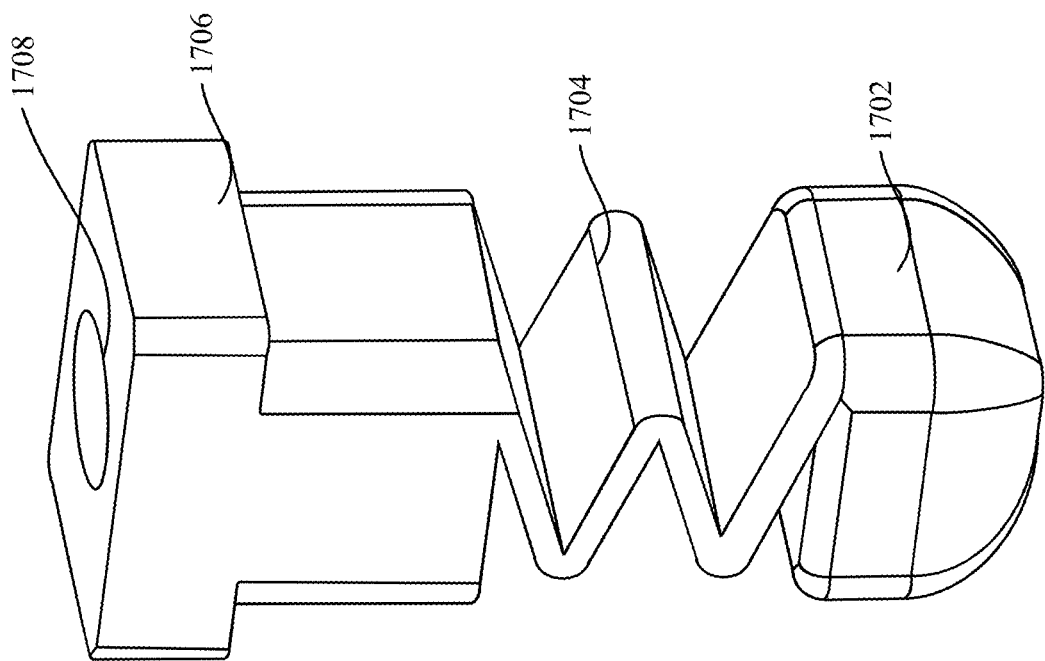
FIGS. 17A and 17B illustrate a streaking cone according to an embodiment of the present disclosure.
Figure 17A:
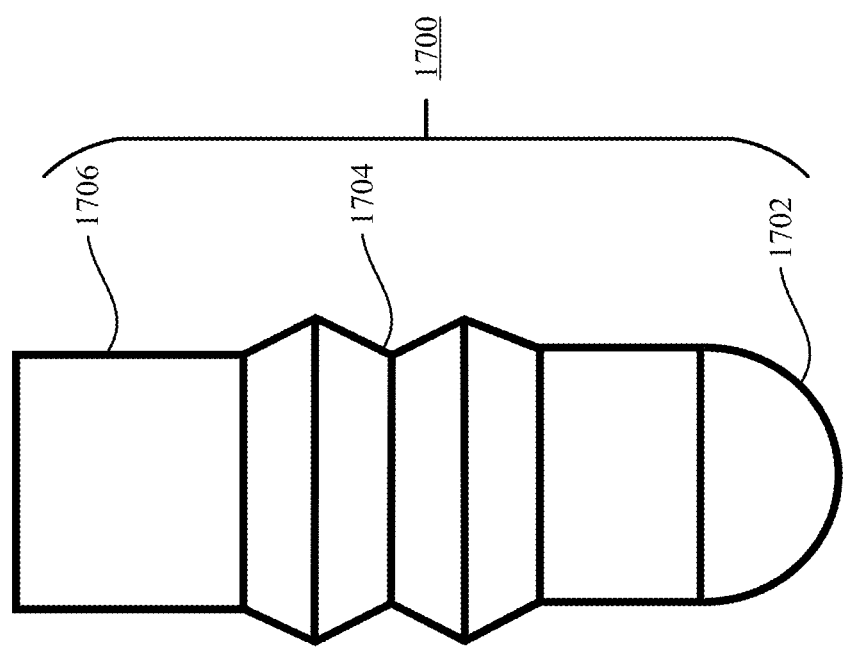

Referring to FIGS. 15 through 17, in some embodiments the instruments include a clone separate apparatus, which allows for an automated microbial culture generation. As illustrated in FIG. 15, a pipette 1500 is utilized to aspirate distilled water 1502, or a similar buffer or diluent medium, and air 1504, or a similar gas or medium, in an alternating manner. These alternative aspirations are repeated a predetermined number of times, according to a design of the present disclosure. For instance, in some embodiments, there are five total alternations, ten total alternations, twenty total alternations, or fifty total alternations. In some embodiments, a volume of each aspiration is uniform (e.g., a volume of aspiration 1502-1 is equal to a volume of aspiration 1504-1, which is equal to a volume of aspiration 1502-2, etc.). In some embodiments, a volume of each type of aspiration is uniform (e.g., a volume of aspiration 1502-1 is equal to a volume of aspiration 1502-2, which is equal to a volume of aspiration 1502-3, etc.). Furthermore, in some embodiments a volume of each aspiration is non-uniform (e.g., a volume of aspiration 1502-1 is not equal to a volume of aspiration 1504-1 or a volume of aspiration 1502-2, which is not equal to a volume of aspiration 1502-3, etc.) Once the final aspiration of air 1504-$i$ is drawn, a final portion of diluent 1502-Z is aspirated. However, the present invention is not limited thereto, as in some embodiments the final aspiration 1502-Z is omitted. Finally, a cell culture 1506 is aspirated.

Referring to FIG. 16, once the contents of the pipette 1500 have been full aspirated, the contents are gradually dispensed into a cell culture medium 1602 (e.g., a petri dish). The dispensing direction is indicated by an arrow 1604 of FIG. 16A and FIG. 16B. In some embodiments, the dispensing direction is a line, a predetermined curve (e.g., a sine curve, a parabolic, a cubic function, etc.), or series of curves (e.g., a parabolic function coupled to a linear line). During dispensing of the contents of the pipette 1500, diluent 1502, air 1504, and the cell culture 1506 exhibit plug flow. However, the present disclosure is not limited thereto, as one skilled in the art may which to exhibit other flow types during dispensing of the contents of the pipette 1500. In some embodiments, a density of contents dispensed decreases as the contents are dispensed, such that an initial dispensing area has a high density while a final dispensing area has a low density. Similarly, in some embodiments the initial dispensing area has a lower density while the final dispensing area has a high density.

Referring to FIG. 17, a streaking cone 1700 is coupled to either the pipette 1500 or a similar device through a coupling portion 1706 of the streaking cone. In some embodiments, the coupling portion 1706 includes a cavity 1708 configured to receiving the pipette 1500. The streaking cone 1700, or a device coupled thereto (e.g., the pipette 1500), is then moved in a continuous motion from a first position to a second position. In some embodiments, the streaking cone is moved in a first continuous motion from a first position to a second position, then in a second continuous motion from a third position to a fourth position. FIGS. 16B and 16D illustrate various spiral continuous motions of the streaking cone 1700 according to embodiments of the present disclosure. However, the present invention is not limited thereto.

For instance, in some embodiments, the streaking is performed in a concentric pattern (e.g., concentric circles, concentric rectangles, concentric triangles) or in an array (e.g., an array of lines, an array of circles, etc.) The continuous motion of the streaking cone is configured to spread the dispensed contents of the pipette 1500 using a tip 1702 of the streaking cone. The tip 1702 of the streaking cone can be designed in a variety of shapes which promote various spreads of cell cultures. Furthermore, in some embodiments the streaking cone 1700 includes an elastic, or flexible, portion 1704 which allows for motion in a vertical axis of the streaking cone. In the present illustration, the flexible portion 1704 is formed as type of spring. However, in some embodiments, the flexible portion 1704 is formed as a damper or similar energy absorbing device. Accordingly, the clone separation apparatus of the present disclosure enables a full range of dilution ratios are realized, which guarantees generation of multiple single colonies.

In some embodiments, the first device is in electronic communication with at least one transport path coupled to the plurality of instruments for receiving a sample from the plurality of instruments and returning the sample to the plurality of instruments. The transport path is utilized to transfer a sample or organic engineering target from an instrument, a unit operation, or a process module to another instrument, unit operation, and/or process module. In many embodiments, the transport path allows a given sample or organic engineering target to traverse three dimensions in a laboratory without human input. In many embodiments, the transport path is the free volume in the system which a transporter can operation unobstructed. The transport path can comprise a multi-lane path or a grid of paths (1030).

In many embodiments, the transport path comprises at least one transporter configured to move about the transport path. A physical storage medium, or buffer, is disposed on the at least one transporter. The buffer is configured to hold a sample or an organic engineering target temporarily to free, or allow, additional operations in the system. For instance, when a sample needs to be disposed in an incubator, but said incubator is occupied for 10 minutes and the instrument said sample was previously disposed requires immediate use by another second sample, the original sample can be disposed in the buffer temporarily to free instruments or arms of a transporter for further use. In many embodiments, the at least one transporter comprises a robotic arm, a ground vehicle, a reduced friction ortho-multilane conduit, a drone, a conveyor belt, a transfer station, a lift, a crane, an elevator or a combination thereof. The present disclosure is not limited thereto, and many types of transportation devices can be utilized by a person skilled in the art of the present disclosure. In many embodiments, the at least one transporter comprises a liquid handling robot. In such embodiments, a typical transporters configuration requires a first transporter as a general transporter and a second transport as a liquid handling robot. Transporters can utilize series or parallel routes, as well as combination routing of series and parallel processing routes. These combinations can reduce travelling times through optimized flexible routing between unit operations and/or instruments. Additionally, the transporter and transport path should be configured to reduce friction, thus minimizing operating forces, to increase smoothness of transportation. This decrease a risk of sample dropping, spilling, cross contamination and the like. (1032, 1034, 1036).

The method further requires translating, for each respective organic engineering target in the first plurality of organic engineering targets, the first uncompiled workflow into a corresponding instance of a compiled first workflow for the respective organic engineering target. In general, an uncompiled workflow is a workflow prior to obtaining a particular sample input. An instance of a compiled workflow is a single iteration of a workflow among a plurality of iterations of said workflow (1038).

In some embodiments, such as biofoundry, each respective compiled workflow in the plurality of instances of the compiled first workflow is a scheme to synthesize and express a pair of TALEN in a single transcript format by a P2A self-cleavage sequence (1040).

In such embodiments, at least 400 pairs of TALENs are expressed in a 24-hour time interval; however, the present disclosure is not limited thereto. In some embodiments, at least 200 pairs of TALENs are expressed in a 24-hour time interval, and in another embodiment at least 600 pairs of TALENs are expressed in a 24-hour time interval. An exact number of completed workflows or expressed organic engineering targets may vary depending on a number of environment, workflow, and system conditions (1042).

In some embodiments, the first organic engineering target in the first plurality of organic engineering targets is converted into one or more first inputs for the first uncompiled workflow. For instance, when the first organic engineering target is an end goal or desired output, such as salt (NaCl), the engineering target is converted into the reagent components of that output, such as Sodium (Na) and Chlorine (Cl) (1044).

In some embodiments, the first organic engineering target is a synthesis of a first nucleic acid and the one or more first inputs for the first uncompiled workflow are a set of nucleic acid bases for synthesizing the first nucleic acid (1046).

In some embodiments, the first uncompiled workflow includes a branch condition, a loop condition, or nested condition, and the translating resolves the branch condition, loop condition or nested condition based on a value associated with the branch condition, loop condition or nested condition in order to form the linear temporal order of the first plurality of unit operations. In some embodiments, loop conditions are logical criterion to exit a loop. In some embodiments, branch conditions are logical criterion to determine the branch for the program to proceed at a fork. The logical conditions usually require the input from the experiment or workflow itself. For example, after running a sample batch in Process Module A, when all measurements surpass threshold X, then execute Branch N. (1048).

Each respective instrument in the first subset of instruments includes an address of the respective instrument and one or more execution instructions for the respective instrument. Instrument execution instruction(s) are at least parameter sets used in programming of unit operations, process modules, and workflows. The instrument execution instructions sets are the configurations of machines and process conditions. Such machine configurations and process conditions include, but are not limited to, adjusting rotations per minute (RPM) of a machine, changing a status of a machine from or to ON and OFF, and the like. Another interpretation of instrument execution instructions is a logical dependency of unit operations in a workflow that defines the procedures that samples are processed (1050).

For example, an instrument executable instruction(s) can include, but are not limited to:
    run Unit Operation 1 with Parameter Set 1 for Sample IDs A-Z
    run Process module 1 with Parameter Set 2 for Sample IDs A-Z
    if Results from Process module 1>Threshold 1, then
    run Process module 2 with Parameter Set 3 for Sample IDs A-Z
    else if
    run Process module 3 with Parameter Set 4 for Sample IDs A-Z Instrument execution instructions can either be interpreted as specific value or coordinate instructions such as:
    Parameter Set 1 through n
    Sample 1 through n
    Threshold 1 through n Additionally, instrument execution instructions can be interpreted as dependencies in the process such as:
    execute 2) after 1)
    execute 3) after 2)
    execute 4) after logic decision 3)
    execute 6) after logic decision 3

In some embodiments, the address of the respective instrument comprises spatial coordinates including, but not limited to, Cartesian coordinates, polar coordinates, spherical coordinates, joint coordinates, or tool coordinates of the respective instrument. In some embodiments, the address of the respective instrument comprises a physical location of the respective instrument. In many embodiments, the address of the respective instrument comprises a unique electronic address of the respective instrument such that the first device, such as computer 10, can communicate with the instruments electronically. The corresponding instance of the respective compiled workflow further comprises an operating condition for the respective instruction. The operating condition of the respective instruction can include a parameter of an instruction such as a final value check or initial verification. (1052, 1054, 1056, 1058).

Figure 19:
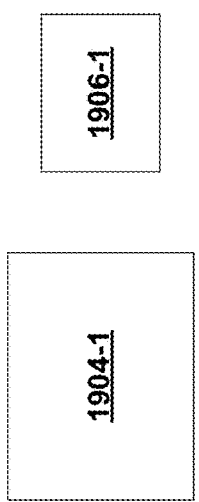
FIG. 19 illustrates a positioning system according to an embodiment of the present disclosure.

Referring to FIG. 19, positioning and control methods and systems of various instruments will be described in relation to a sample foundry 1900. The foundry 1900 includes a transporter 1902, a variety of instruments 1904, and a variety of markers 1906. In some embodiments, the transporter 1902 includes an articulated handling robot, or extension, which handles various samples and subcomponents of the instruments 1904. In some embodiments, the articulated handling robot is the handling robot 1802 of FIG. 18.

Each instrument 1904 of the foundry 1900 includes a respective address, which is a coarse grain address, that is identified through a corresponding marker 1906. Coarse grain addresses allow the transporter 1902 to position itself in a position suitable to operate a respective instrument within a tolerance of from 1 millimeter (mm) to 20 mm. Markers 1906 provide positional information to localize the transporter 1902. Accordingly, the positioning system locates and guides the transporter 1902 to a position proximate to the respective instrument 1904 of the marker 1906 using the coarse grain address.

In some embodiments, instruments 1904 and corresponding markers 1906 exist in a one-to-one relation (e.g., instrument 1904-1 is unique to marker 1906-1), a many-to-one relationship (e.g., instruments 1904-3 and 1904-4 are associated with marker 1906-2), or a one-to-many relationship (e.g., instrument 1904-2 is associated with markers 1906-3 through 1906-6 which correspond to different orientations of the instrument). In some embodiments, when an address, or position, of a marker 1906 is determined, the address is stored for later user. For instance, when a position of a first marker is detected, the detected position is stored such that when the first marker is recalled upon in a later instance of a workflow, the position of the marker does not need to be redetected. In some embodiments, the position is stored in non-volatile memory. In some embodiments, the position is stored in volatile memory. Accordingly, the position of a marker is re-determined for each workflow.

In some embodiments, the positioning system is a global positioning system (GPS) and each marker 1906 is a GPS coordinate. Likewise, in some embodiments the positioning system is a radio frequency (RF) system and each marker 1906 is a RF signal generator. Moreover, in some embodiments each marker 1906 is a two-dimensional (2D) marker (e.g., a barcode, a quick-reference (QR) code, a color patch, etc.), which is detected and captured using a variety of sensors (e.g., light detection and ranging (LIDAR) sensors, ultrasonic sensors, encoders, a compass, etc.) or a camera (e.g., a high resolution camera such as the JS 1080p, 120 degrees, distortion free camera or RerVision USB8MPO2G camera) attached to the transporter 1902. These sensors and/or camera feed real time information to a controller and provide information related to a spatial location of the transporter and/or articulated handling robot of the transporter, as well as their surrounding environment. For instance, in some embodiments, the transporter includes one or more LIDAR sensors or detectors which use electromagnetic waves to detect obstacles in a three-dimensional environment (e.g., a biological foundry). In some embodiments, the LIDAR sensor is a SICK LMS-111 LIDAR sensor. This LIDAR sensor operate at a wavelength of 905 nanometers (nm) (e.g., infrared), with an aperture angle of 2700 and a scanning frequency of 25 Hertz (Hz) to 50 Hz. However, the present disclosure is not limited thereto. For instance, in some embodiments the wavelength of light used by a sensor is of from 10 micrometers to 250 nm.

In some embodiments, the positioning system is a set of predetermined paths. An inertial measurement unit (IMU) sensor is coupled to the transporter 1902 in order to detect disturbances to the transporter and correct for the disturbances. The IMU sensor includes an accelerometer, a gyroscope, and a magnetometer. When a disturbance is detected through the IMU sensor, the transporter 1902 adjusts its position to accord for the disturbance and remain in a stationary position, or remain on its current transport path. In some embodiments, the IMU sensor is a Lord Sensing 3DM-GX5-25 IMU sensor. Furthermore, in some embodiments the positioning system includes a series of magnetic scales, where the markers 1906 are magnetic markers. Accordingly, the transporter 1902 traverses the magnetic scales and locates the instruments through the magnetic makers 1906. In some embodiments, the sensors of the present disclosure have a suitable range such that all instruments of a foundry are within the range of the sensor.

In some embodiments, the above described positioning systems are utilized to form a map, or representation, of a surrounding environment of the foundry 1900 in order to generate predetermined paths for the transporter 1902. In some embodiments, the above described positioning systems are utilized to form a map, or representation, of a marker positioning in the foundry 1900 in order to generate predetermined paths for the transporter 1902. Furthermore, in some embodiments, a Gaussian blurring function or low-pass filter is applied to either the representation or captured feed to de-noise an image and limit a range of error in determining a positioning of each marker 1906. In some embodiments, the representation is formed such that the transporter 1902 is an origin, or zero, of the representation. Similarly, in some embodiments the representation is formed such that a center of a surrounding environment of the transporter 1902 is an origin, or zero, of the representation.

In accordance with a determination that the transporter is at a correct coarse grain address (e.g., marker 1906) of a respective instrument 1904, the transporter is held in position. In some embodiments, the transporter is held in position by being lifted through one or more extending linear actuators. Similarly, in some embodiments the transporter is held in position through feedback of a proportional-integral-derivative loop controller in communication with the sensors.

In some embodiments, while the transporter 1902 is actively moving, the sensors (e.g., LIDAR sensor and/or IMU sensor) are active in detecting the surrounding environment of the transporter and marker positions. Accordingly, the transporter 1902 is capable of reacting to a disturbance in its transport path (e.g., detecting a person or obstacle moving through, or standing in, the transport path). This reaction allows the transporter to slow down, stop, or reroute to a different transport path depending on each disturbance and workflow.

The articulated hand utilizes a fine transverse instruction to move to at least one spatial coordinate of a respective instrument. For instance, in some embodiments a fine traverse instruction is a command to extend the articulated arm in a horizontal line.

In some embodiments, while handling various samples the articulated handling robot transfers a tray (or similar component of an instrument or workflow such as a vial or container) to an instrument 1904 using a safety transfer procedure, which is type of fine traverse instruction. This safety transfer procedure is conducted when a readout from the sensors, or similar positioning system, fails to satisfy a threshold proximity location (e.g., a threshold of 1 mm, a threshold of 5 mm, a threshold of 20 mm, a threshold of 100 mm, a threshold of 0.1 degrees' rotation, a threshold of 0.25 degrees' rotation, a threshold of 0.5 degree's rotation, a threshold of 1 degree rotation, etc.) of an actual location of the instrument. Similarly, when the threshold proximity location is satisfied, a default transfer procedure is conducted. For instance, in some embodiments the transporter 1902 determines that it is in a correct positioning in relation to a corresponding marker 1906. However, the sensors detect that the transporter 1902 is in an incorrect position, which enables the safety transfer procedure.

In some embodiments, the safety transfer procedure includes utilizing a force detection sensor, which allows for compliance in the motion of the robot. In some embodiments, the force detection sensor is a torque sensor. The safety transfer procedure initiates a small (e.g., tightly grouped), slow oscillating motion to gradually load a container to a receiving portion of an instrument. The oscillating motion includes a simple oscillation, a Lissajous oscillation, or a spiral-shaped oscillation. For instance, in some embodiments the articulated arm extends in a direction, with small (e.g., 2 mm radius) spirals oriented about the direction of extension. When a force is detected by the force sensor, the path of extension is modification to be compliant with the detected force. Since the robot is compliant to detected forces and disturbances, the oscillating motion is constrained to the boundaries and chafers of the instrument, which allows for the articulated handling robot to find and fit the container into the instrument without a hard collision caused by incorrect positioning.

The method further requires the first plurality of unit operations to be temporally organized into a linear temporal order. Each respective unit operation in the first plurality of unit operations is characterized by the time interval of the corresponding unit operation definition. For example, referring to FIG. 6A, process module DNA Quantification includes unit operations Spectrophotometry and Pipetting. The unit operation definition(s) for Spectrophotometry defines a 40-minute time interval, and the unit operation definition(s) for Pipetting defines a 10-minute time interval. Thus, the first plurality of unit operations would have required at least 50 minutes and have at least two plausible workflows. As such, a plurality of instances of the compiled first workflow are formed (1060).

Figure 10:
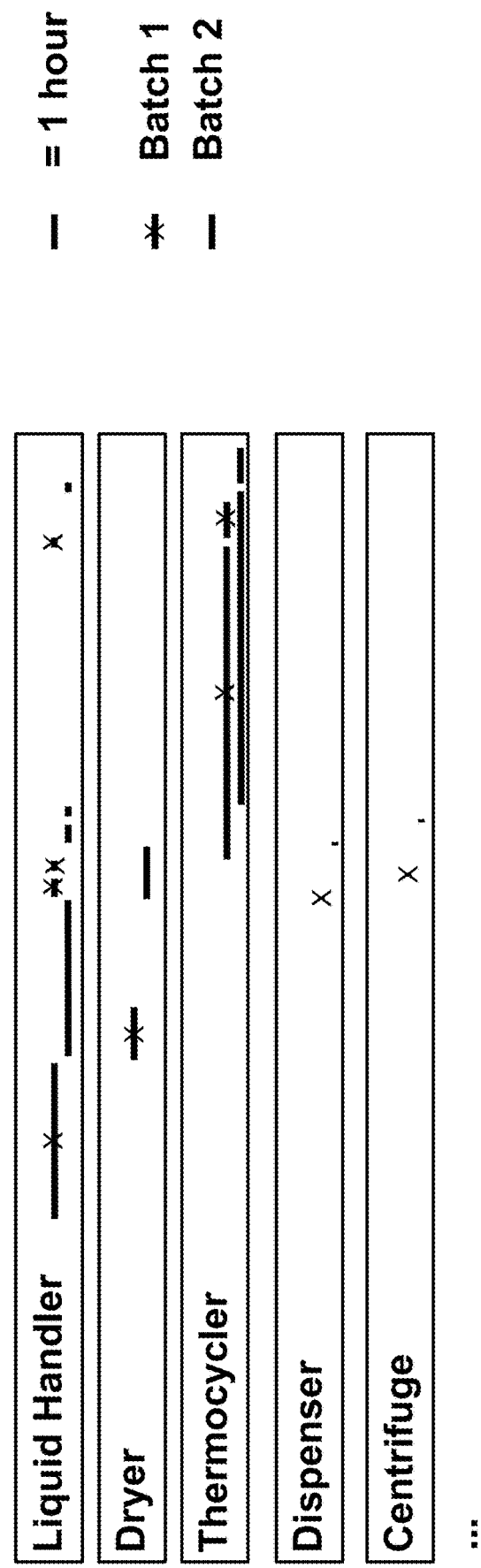
FIG. 10 illustrates a Gantt chart for automated Golden Gate DNA assembly workflow according to an embodiment of the present disclosure.

In some embodiments, the method enables the user of the first device, via a graphical user interface or otherwise, to adjust the linear temporal order of the first plurality of unit operations. Such graphical user interfaces include, but are not limited to, the Gantt chart depicted in FIG. 10. In FIG. 10, "Batch 1" refers to a first workflow and "Batch 2" refers to a second workflow. A user of the first device can adjust and order the unit operations of a workflow of at their discretion. In some embodiments, predetermined contingency checks may prevent a user from ordering unit operations in less than optimal configurations or configurations which trigger a predetermined alert (1062).

In some embodiments, each organic engineering target in the first plurality of organic engineering targets is an input into a corresponding instance of a compiled first workflow in the plurality of instances of the compiled first workflow.

In some alternative embodiments, each organic engineering target in the first plurality of organic engineering targets is an output into a corresponding instance of a compiled first workflow in the plurality of instances of the compiled first workflow.

In general, an engineering target can be, at any given point in time, an input or output of an instance of the same compiled workflow. Likewise, an input of a workflow can be the input of another workflow (1064, 1066).

In some embodiments, the method further requires obtaining, via the one or more peripheral devices, a second plurality of organic engineering targets. As previously described, the second plurality of engineering targets or samples can exist is a variety of forms, including, but not limited to, the forms of the first plurality of organic engineering targets (1070).

In some embodiments, the second plurality of organic engineering targets are determined from outputs of the plurality of instances of the compiled first workflow. In such embodiments, the second workflow can commence subsequent completion of the compiled first workflow (1072).

Furthermore, in some embodiments, the method assigns the second plurality of organic engineering targets to a second uncompiled workflow. Like the first uncompiled workflow, the second uncompiled workflow is configured to produce the second plurality organic engineering targets, and the second uncompiled workflow is associated with a second subset of process modules in the plurality of process modules (1074).

In some embodiments, the method further performs a second translating, for each respective organic engineering target in the second plurality of organic engineering targets, the second uncompiled workflow into a corresponding instance of a compiled second workflow for the respective organic engineering target (1076).

In many embodiments, two or more instances of the compiled first workflow are executing at a time when the second translating is executed. (1078) As used here, a compiled workflow is "executing" when at least one unit operation of the compiled workflow is presently being serviced by an instrument specified by the unit operation. For example, consider the case where a unit operation in a compiled workflow specifies that an aliquot of fluid be pipetted into a tube. In some embodiments, the compiled workflow that contains unit operation is "executing" during the actual physical pipetting operation specified by the unit operation while the instrument is performing the pipetting as instructed by the unit operation. In some embodiments, the compiled workflow that contains a unit operation is "executing" during the entire time interval in the unit operation that contains this pipetting operation, not just the actual physical amount of time that it takes the instrument to perform the pipetting. Thus, in such embodiments, the compiled workflow is deemed to be "executing" across the entire time interval of the unit operation, even if the physical instructions of the unit operation are completed by the specified instrument before the entire time interval is completed. More generally, a compiled workflow is deemed to be executing in some embodiments when the execution instructions of any respective unit operation of the compiled workflow is currently controlling an instrument in the plurality of instruments within the time interval specified by the respective unit operation.

Each respective instrument in the second subset of instruments includes an address of the respective instrument and one or more execution instructions for the respective instrument. Like the instruments of the first subset of instruments, the respective addresses can exist is a plurality of forms including physical addresses and unique electronic addresses (1080).

The second plurality of unit operations is temporally organized into a linear temporal order. Each respective unit operation in the second plurality of unit operations is characterized by the time interval of the corresponding unit operation definition. Like the linear temporal order of the first plurality of unit operations, the second plurality of unit operations can be manipulated, via a graphical interface, by a user of the device or computer. (1082).

In some embodiments, two or more of the plurality of instances of the compiled first workflow and two or more of the plurality of instances of the compiled second workflow are concurrently executed. As used herein, a "concurrently running" element refers to a unit operation of a workflow is being currently enacted on an instrument in a plurality of instruments (1084).

In some embodiments, the first subset of instruments comprises two or more instruments, the second subset of instruments comprises two or more instruments, and at least one instrument in the first subset of instruments is in the second subset of instruments (1086).

In some embodiments, the method requires concurrently executing three or more of the plurality of instances of the compiled first workflow and three or more of the plurality of instances of the compiled second workflow, wherein, the first subset of instruments comprises three or more instruments, the second subset of instruments comprises three or more instruments, and at least two instruments in the first subset of instruments is in the second subset of instruments. (1088)

In some embodiments, the method requires validating the second plurality of unit operations according to a predetermined validation list. The predetermined validation list comprises one or more criteria of the compiled second workflow. The one or more criteria of the compiled second workflow comprises a priority of each unit operation in the second plurality of unit operations, a weight of each unit operation in the second plurality of unit operations, a time of completion for the second plurality of unit operations, a compatibility of the second plurality of unit operations to a different plurality of unit operations, a property of each unit operation in the second plurality of unit operations, and one or more constraints of the second plurality of unit operations. The property of each unit operation in the second plurality of unit operations is selected from the set: a viscosity value, a purity value, a composition value, a temperature value, a weight value, a mass value, and a volume value. (1090, 1092, 1094)

In some embodiments, the method requires concurrently executing one or more instances of the compiled first workflow and one or more instances of the compiled second workflow, concurrently executing two or more instances of the compiled first workflow and three or more instances of the compiled second workflow, or concurrently executing three or more instances of the compiled first workflow and three or more instances of the compiled second workflow (1096, 1098, 1100).

In some embodiments, the method requires, at each respective time step in a recurring series of time steps, simulating a remainder of each of the one or more instances of the compiled first workflow. This forms one or more first simulations, each simulating a remainder of each of the one or more instances of the compiled second workflow, thus forming one or more second simulations. Simulating a remainder of the one or more instances of a compiled workflow allows greater optimization in real time and allows adaptation to new inputs and completed workflows. An interlocking condition error handler associated with a first unit operation in an instance of the one or more instances of the compiled first workflow is fired which forms an interlocking condition with a second unit operation in an instance of the one or more instances of the compiled second workflow. (1102)

In some embodiments, firing the interlocking condition error handler adjusts one or more time intervals of one or more unit operations in an instance of the compiled first workflow or an instance of the compiled second workflow that have not been executed. An interlocking condition is a logical conflict in scheduling when one action require resources that is being occupied by another action but can only be released when the first action proceeds. Firing the interlocking condition error handler can adjust various parameters, including, but not limited to, a weight one or more unit operations in an instance of the compiled first workflow or an instance of the compiled second workflow that have not been executed as a function of a priority assigned to the compiled first workflow versus a priority assigned to the compiled second workflow, one or more time intervals of one or more unit operations in an instance of the compiled first workflow or an instance of the compiled second workflow that have not been executed as a function of a priority assigned to the compiled first workflow versus a priority assigned to the compiled second workflow, or an instance of the compiled first workflow or an instance of the compiled second workflow. In some embodiments, the interlocking condition error handler is a mutual exclusion error handler. The interlocking condition error handler can also include a race condition or a lock condition (1104, 1106, 1108, 1110, 1112)

In some embodiments, firing the interlocking condition error handler suspends an instance of the compiled first workflow or an instance of the compiled second workflow. Suspending a workflow, as used herein, means aborting or ending a workflow or temporarily halting a workflow (1114).

In some embodiments, each time step in the recurring series of time steps occurs on a periodic basis. In some embodiments, each time step in the recurring series of time steps occurs every five minutes. In further embodiments, each time step in the recurring series of time steps occurs every 10 minutes, every 15 minutes, every 25 minutes, every 30 minutes, every 45 minutes, every 60 minutes, every 120 minutes, every half day, every day or the like (1116, 1118).

In some embodiments, each time step in the recurring series of time steps occurs responsive to an occurrence of event in a plurality of event classes. An event class is an event triggered rescheduling condition. This describes one type of rescheduling conditions that are triggered by events such as equipment malfunction. Other such events include, but are not limited to, adding a new compiled workflow, instances of compiled workflows finishing with a delay or advance, when actual decisions or looping cycles are not included in the simulated instances or workflows, abnormal resource status, such as malfunction, user interruption, instrument error, a power failure, a sample dropping, or an interlocking condition and the like. A rescheduling condition is a logical criterion for a rescheduling routine to be executed (1120, 1122).

In many embodiments, the first subset of instruments comprises two or more different instrument classes, and the second subset of instruments comprises two or more different instrument classes. Typically, an instrument class can refer to a type of instrument, such as the previously mentioned 96 well and 24 well plates (1124).

A first instrument class and a second instrument class is used by both the plurality of instances of the compiled first workflow and the plurality of instances of the compiled second workflow. The first instrument class has a first multiplex value and the second instrument class has a second multiplex value other than the first multiplex value. The method enacts a scheduler that maximizes a number of instances of the plurality of instances of the compiled first workflow, a number of instances of the plurality of instances of the compiled second workflow, or a number of instances of a combination of instances of the compiled first workflow and the compiled second workflow that can concurrently use instruments of the first instrument class and instruments of the second instrument class given the first multiplex value and the second multiplex value. The scheduler orchestrates the unit operations on a container level, while a script generator (to be described infra) handles individual samples in said container in a pipetting operation. As such, the script generator converts experimental designs, such as DNA construct design, enzyme assay design, and/or restriction digestion design, into instrument executable instructions. The scripts generated by the by the script generator will be utilized as a part of a configuration for unit operations when the scheduler dictates a workflow. Additionally, classes of instruments can be utilized when instruments exist in various multiplex. For instance, when well plates exist in 96 well implementations and 24 well implementations, a first subclass includes each 96 well plate having a first multiplex value of 1 and a second subclass includes each 24 well plate having a second multiplex value of 4. The multiplex values are typically utilized when instruments exist is various configurations and throughput of a plurality of devices needs to be optimized (1126).

The scheduler maximizes, at least in part, by invoking a first number of instances of the first instrument class as a function of the first multiplex value of the first instrument class and invoking a second number of instances of the second instrument class as a function of the second multiplex value of the second instrument class to be run concurrently support concurrently running instances of the compiled first workflow and the compiled second workflow (1128).

The scheduler maximizes, at least in part, by concurrently running a first number of instances of the first compiled workflow and a second number of instances of the second compiled workflow (1130).

The scheduler maximizes, at least in part, by adjusting, by an amount, a time interval of a respective unit operation in the first plurality of unit operations of an instance of the first compiled workflow from the time interval of the corresponding unit operation definition or by adjusting, by an amount, a time interval of a respective unit operation in the second plurality of unit operations of an instance of the second compiled workflow from the time interval of the corresponding unit operation definition (1132).

Incorporated by reference in the present document is "Chao et al., 2017, "Fully Automated One-Step Synthesis of Single-Transcript TALEN Pairs Using a Biological Foundry," ACS Synth Biol, 6, p 678".

Example I—Design of a Single-Transcript TALEN Synthesis Scheme

Figure 11A:
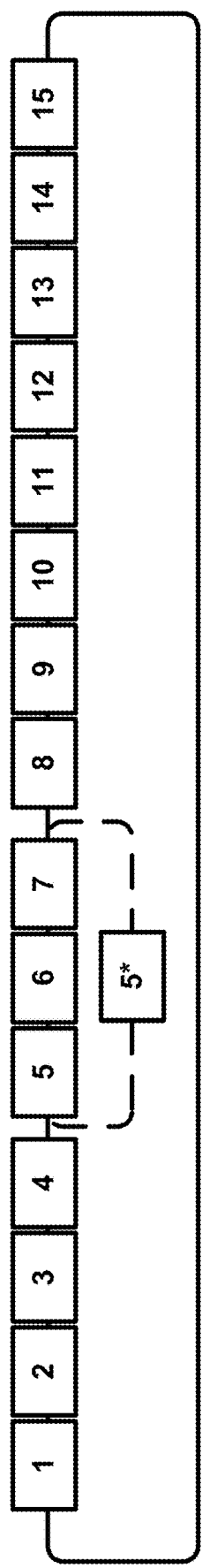

The TALEN architecture used in this work is based upon the AvrXa10 TALE from *Xanthomonas oryzae* pv. *oryzae* as previously reported (Liang et al., 2014, "FairyTALE: A high-throughput TAL effector synthesis platform," ACS Synth Biol, 3 (2), p 67). In brief, it utilizes a +207 aa N-terminus extension and a +63 aa C-terminus extension, which negates the 5'-T requirement and allows greater flexibility in target sequence design (Sun et al., 212, "Optimized TAL effector nucleases (TALENs) for use in treatment of sickle cell disease," Mol Biosyst, 8 (4), p 1255). Attached at the C-terminus is an engineered FokI cleavage domain that showed greater cleavage efficiency in yeast as well as human cells (Sun et al., 2014, "SunnyTALEN: a second-generation TALEN system for human genome editing," Biotechnol Bioeng, 111 (4), p 683). The central repeat domains of the two TALENs are constructed from a library of di-repeat substrates, i.e., each substrate contains two TALE repeats that recognize two consecutive DNA bases. For this work, we used a library of 441 di-repeat substrates, adapted from "FairyTALE", equally divided into 17 groups according to their position in the assembly (Liang et al., 2014, "FairyTALE: A high-throughput TAL effector synthesis platform," ACS Synth Biol, 3 (2), p 67) (FIG. 11). In addition to the 4×4 substrates to cover all possible DNA di-bases at each assembly position, we included the option to use either NH or NN to code for guanine "organic engineering targets". To separate the two TALENs on the single plasmid, we employed a poly-cistronic format utilizing a P2A self-cleaving peptide sequence (Donnelly et al., 2004, "Multiple gene products from a single vector: 'self-cleaving' 2A peptides," Gene Ther, 11 (23), p 1673; Kim et al., 2011, "High Cleavage Efficiency of a 2A Peptide Derived from Porcine Teschovirus-1 in Human Cell Lines, Zebrafish and Mice," Plos One, 6 (4)). Both TALENs are coded as a single transcript, but during translation, the P2A peptide will self-cleave the growing polypeptide to give two independent TALENs (FIG. 3A).

Figure 4A:
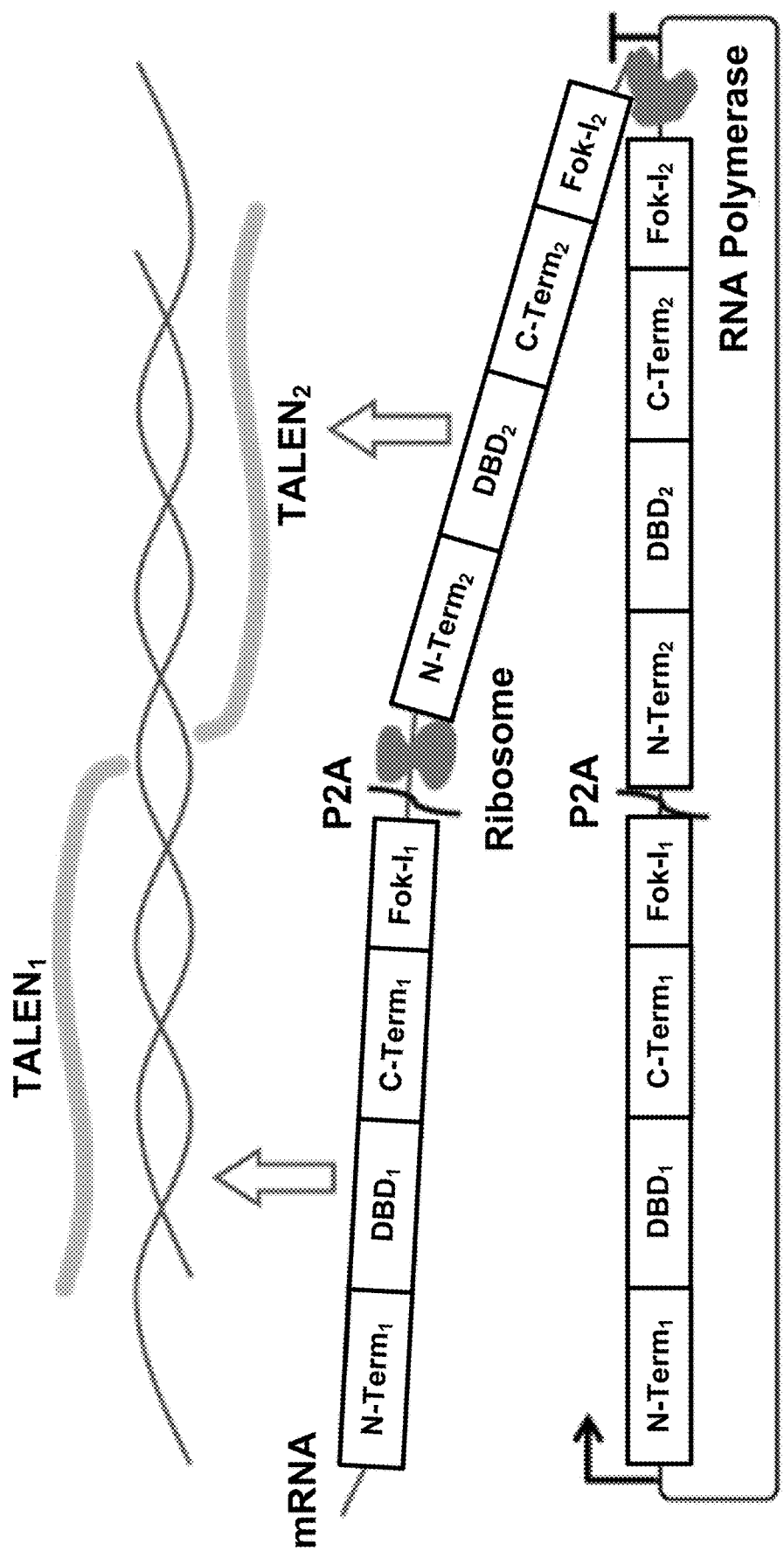
FIG. 4A illustrates an overall design for single-transcript TALEN synthesis according to an embodiment of the present disclosure.
Figure 4B:
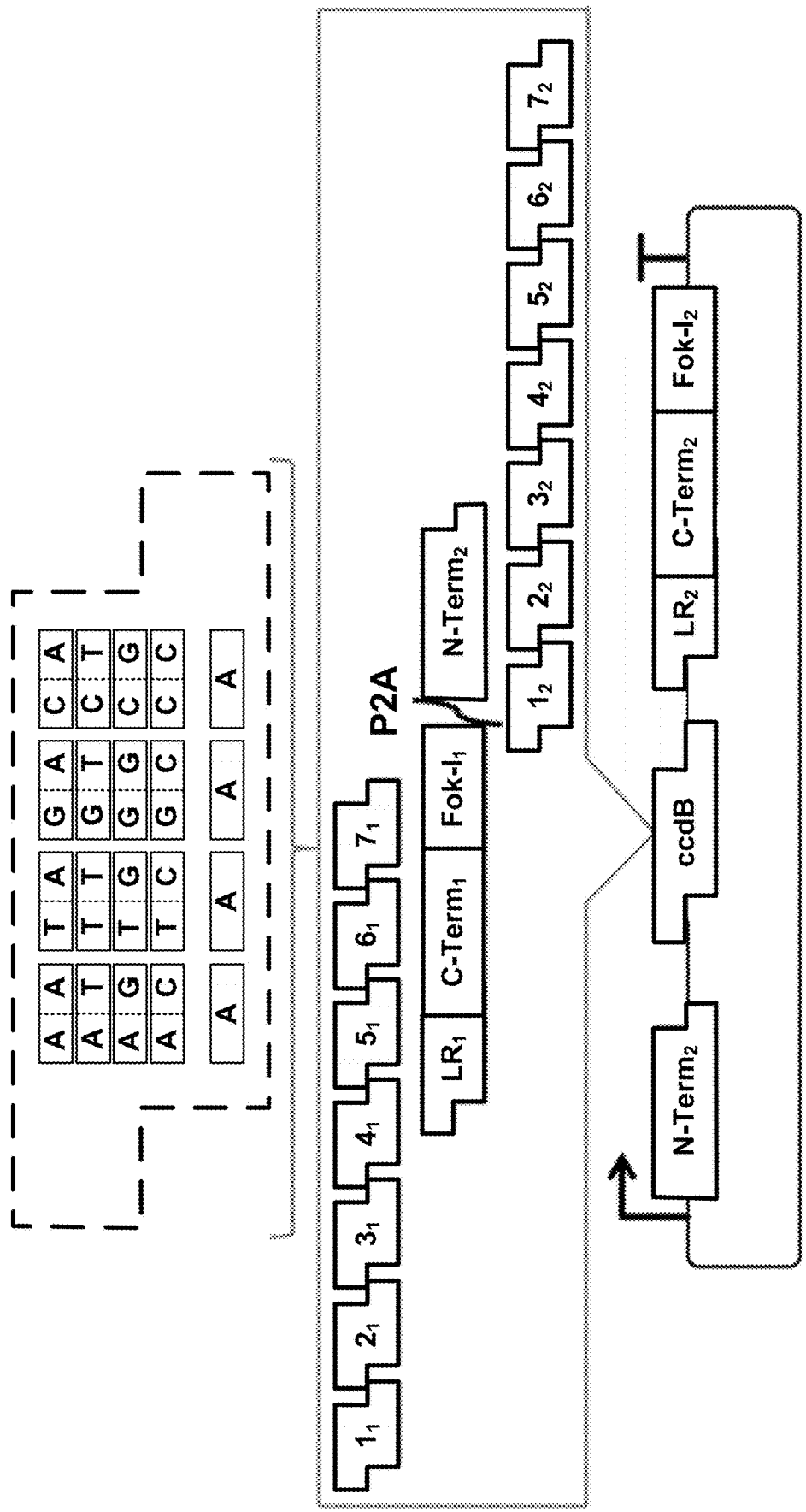
FIG. 4B illustrates an assembly scheme of the design and preliminary test of single-transcript TALEN synthesis according to an embodiment of the present disclosure.

Using the set of optimized 4-bp junctions in the "fairyTALE" construction scheme, 2 sets of 7 di-repeats substrates, with a P2A linker substrate in between, were ligated onto a TALEN receiver vector in a single step via Golden Gate assembly. The N-terminus extension of the first TALEN and the C-terminus extension of the second TALEN were carried by the vector, whereas the C-terminus extension of the first TALEN and the N-terminus extension of the second TALEN were carried by the linker substrate. Since the linker substrate and the receiver carried the last repeat of the two TALENs, 4 TALEN receivers and 4 linker substrates were created (FIG. 4B). This construction scheme assembled 15 DNA fragments onto a 5 kb mammalian expression vector to create a single-plasmid TALEN pair that recognized a 30 bp DNA sequence.

Example II—One-Pot Assembly of TALENs

Figure 4C:
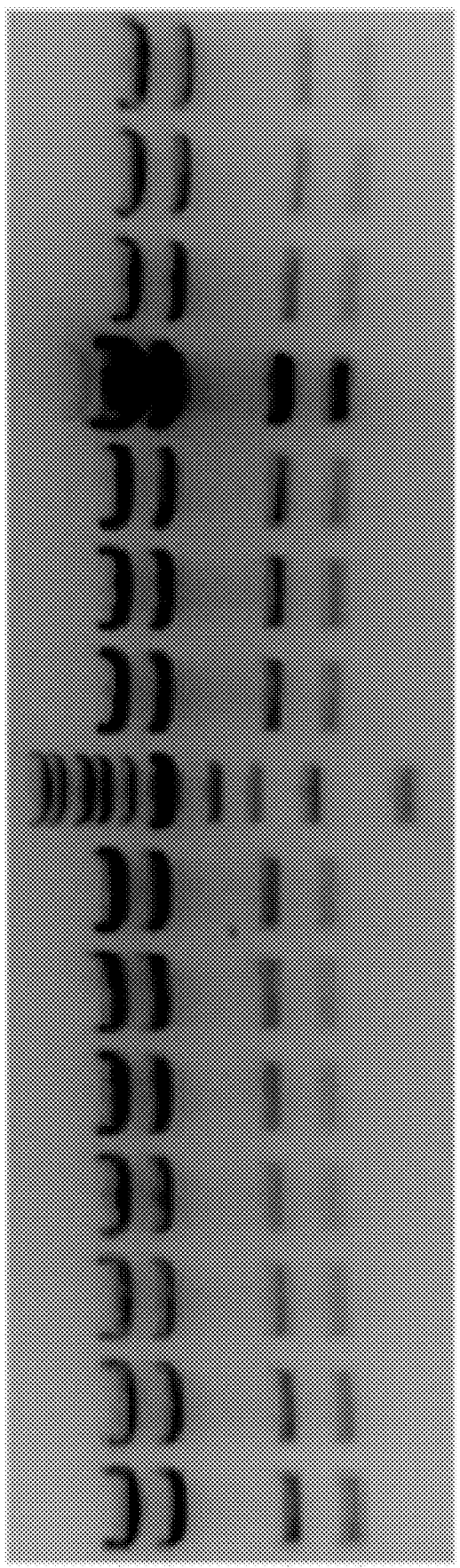
FIG. 4C illustrates a test assembly of a single-transcript TALEN pair according to an embodiment of the present disclosure.
Figure 4C:
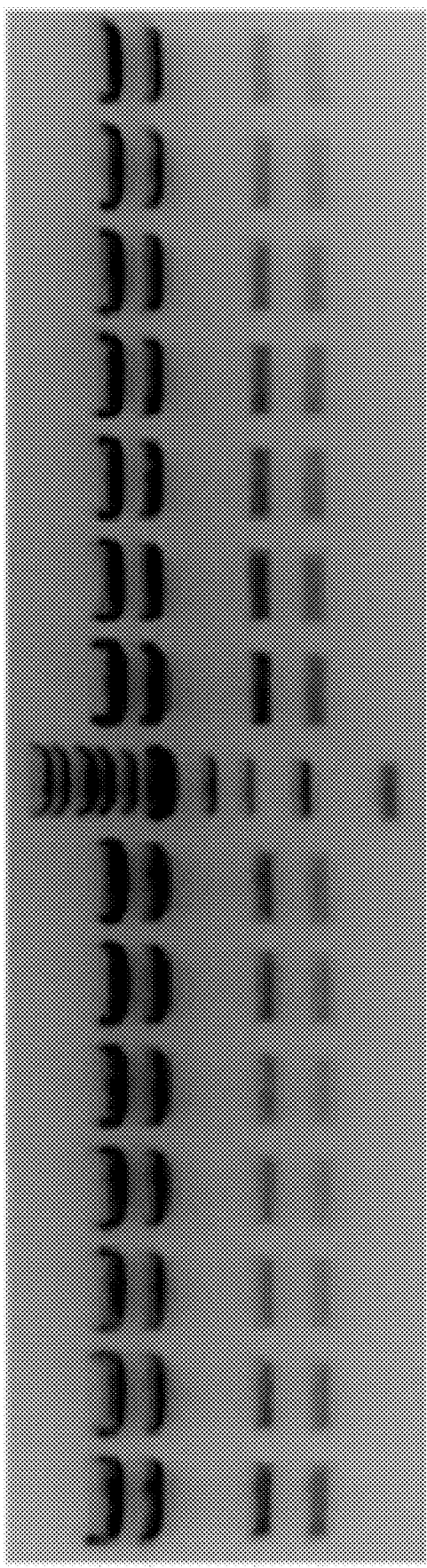

To fulfill the requirements of TALEN library creation, we optimized the reaction condition to maximize the assembly fidelity. For library creation applications, picking individual clones for verification would be an obvious throughput bottleneck, and we would therefore need to achieve high assembly fidelity to allow us to skip clonal isolation without drastically affecting the quality of the library. We picked 28 colonies from a single-transcript TALEN assembly "organic engineering targets", and assessed them by restriction digest followed by gel electrophoreses. As shown in FIG. 4C, all 28 clones gave the correct digestion pattern. We then sequenced 4 of the clones and they all appeared to be correct. This (28/28) corresponds to a fidelity of at least 87.7% based on binomial probability with 95% confidence.

Example IIi—Single-Transcript TALEN Functionality in HEK293T and hESC Cells

Figure 5A:
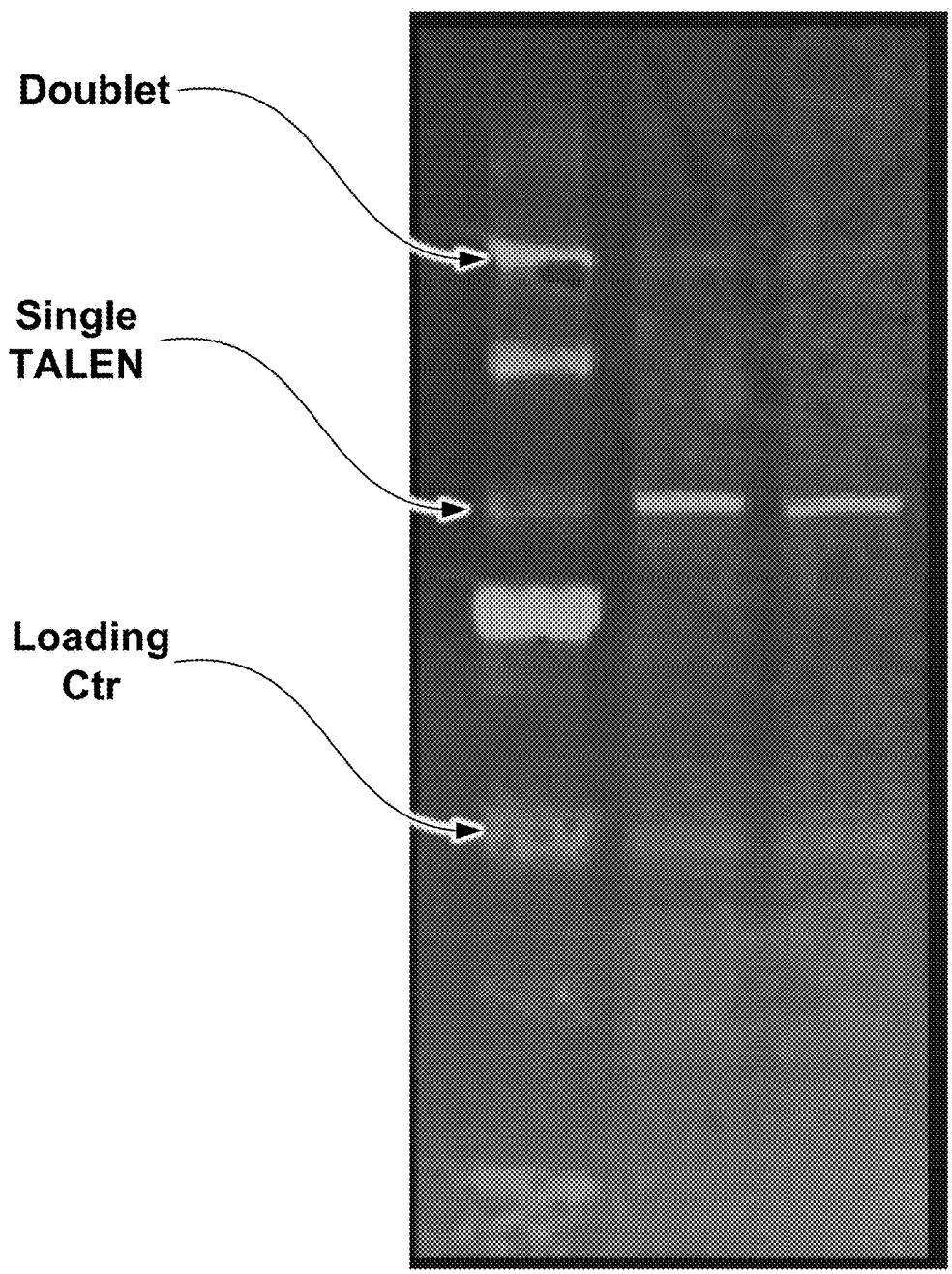
FIG. 5A illustrates a single-transcript expression of a TALEN pair according to an embodiment of the present disclosure.

To ensure that P2A cleaves the protein effectively, we performed a western blot analysis from the cell lysates of HEK293T that had been transfected with single-plasmid TALENs. As shown in FIG. 5A, only TALEN monomer was detected and no dimer could be observed, suggesting that the P2A sequence cleaved the protein effectively in HEK293T cells.

Figure 5B:
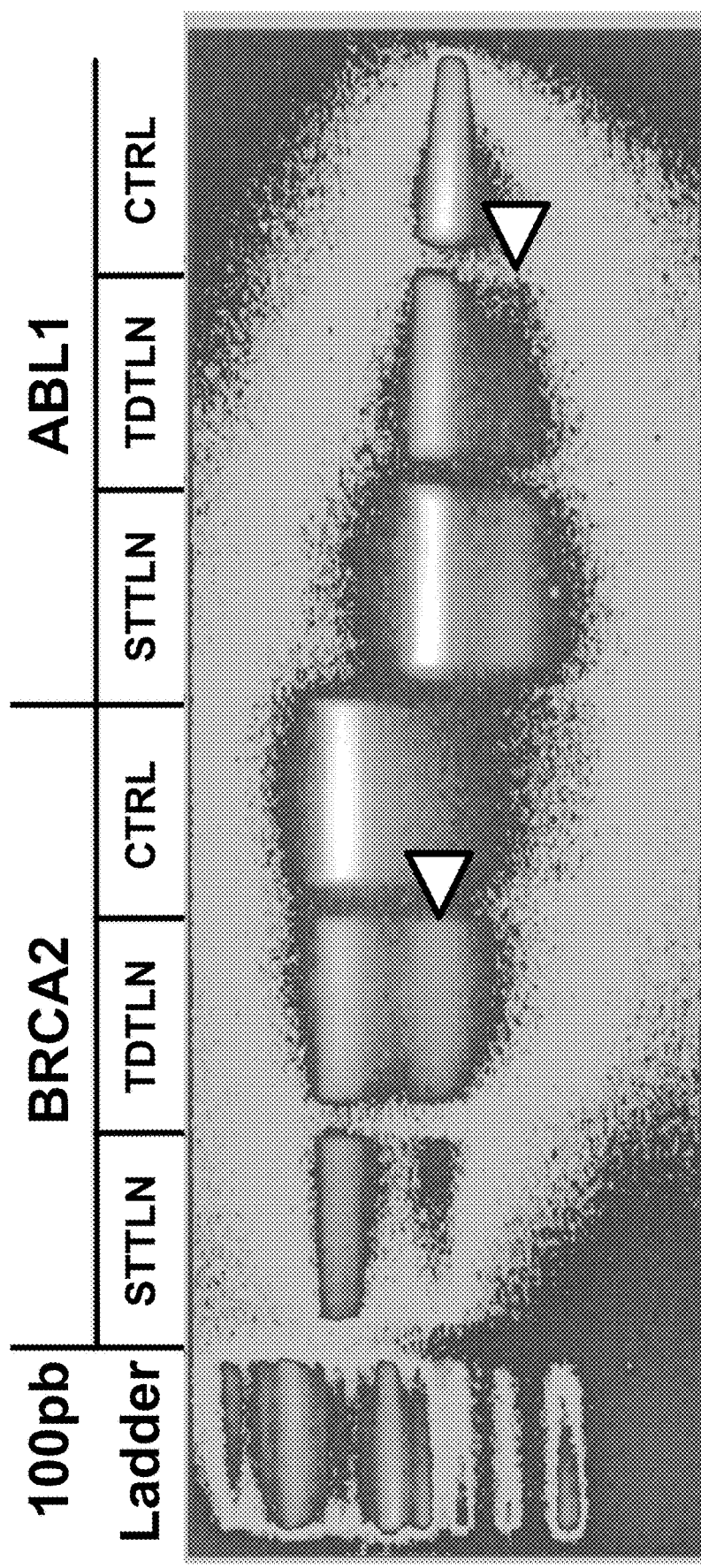
FIG. 5B illustrates genome editing in HEK293T cells according to an embodiment of the present disclosure.
Figure 8A:
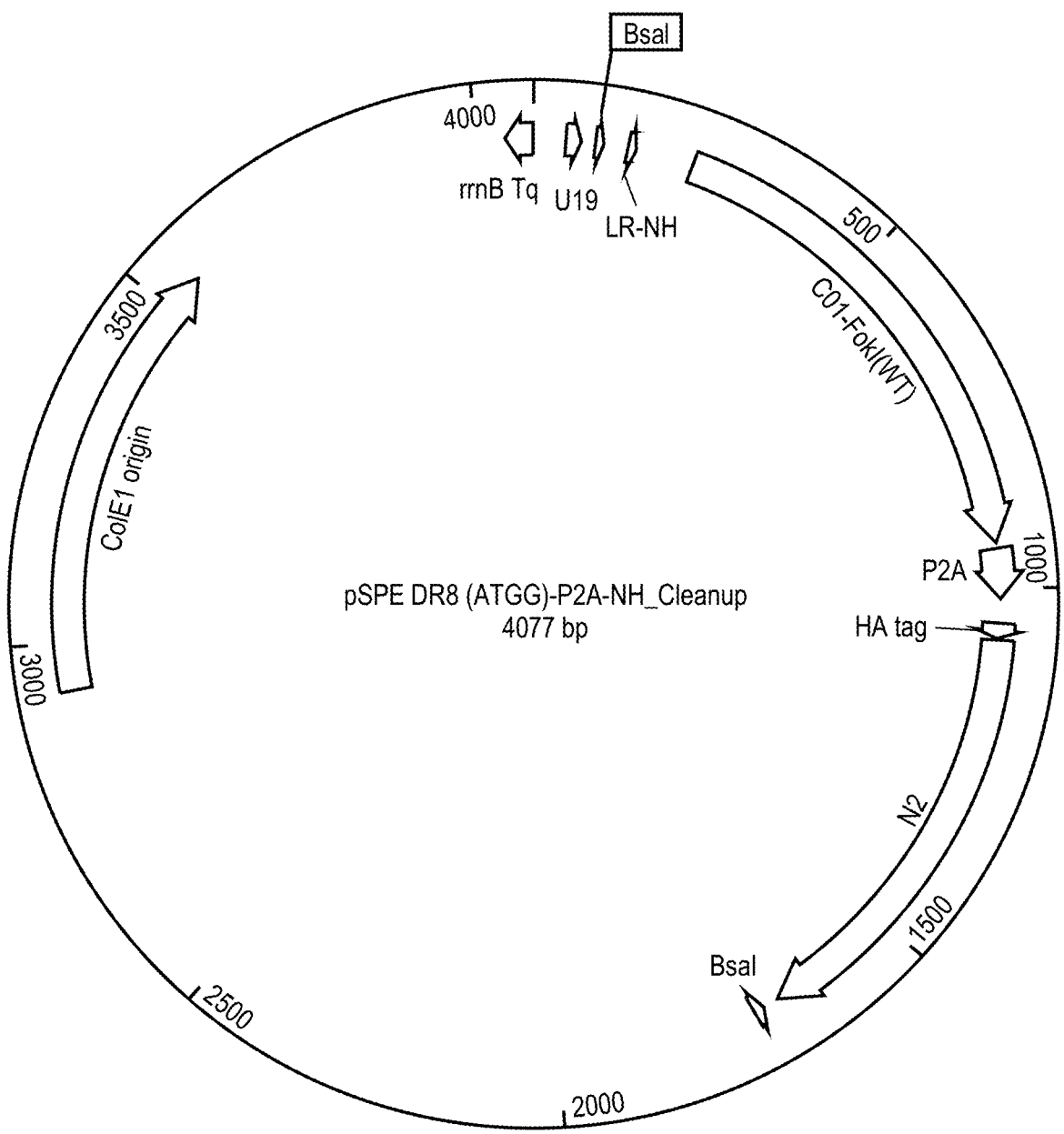
FIGS. 8A and 8B illustrate plasmid design for single plasmid TALEN assembly according to an embodiment of the present disclosure.

After confirming P2A functionality, we went on to compare the DNA cleavage efficiency of single-transcript TALENs against previously reported traditional two-plasmid TALENs. Two sites, ABL1 and BRCA2 "organic engineering targets", were chosen for this comparison, and the experiments "compiled workflows" were performed in HEK293T cells. Cleavage efficiency was measured using the T7E1 nuclease assay, which detects indels introduced via NHEJ after TALEN induced double stranded breaks. As shown in FIG. 5B, the cleavage efficiency of the two single-transcript TALENs was comparable to that of traditional TALENs. The 1P-TALEN used in this experiment used NH to recognize guanine, whereas the traditional TALENs used NN to recognize guanine. According to our observation and in agreement with that reported by others (Streubel et al., 2012, "TAL effector RVD specificities and efficiencies," Nat Biotechnol, 30 (7), p 593), when used in large number, NH RVD is detrimental to TALE binding. We therefore recommend using NN or a mix of NN and NH RVD when there are more than 4 guanine bases in the recognition site (FIG. 8A).

Figure 5C:
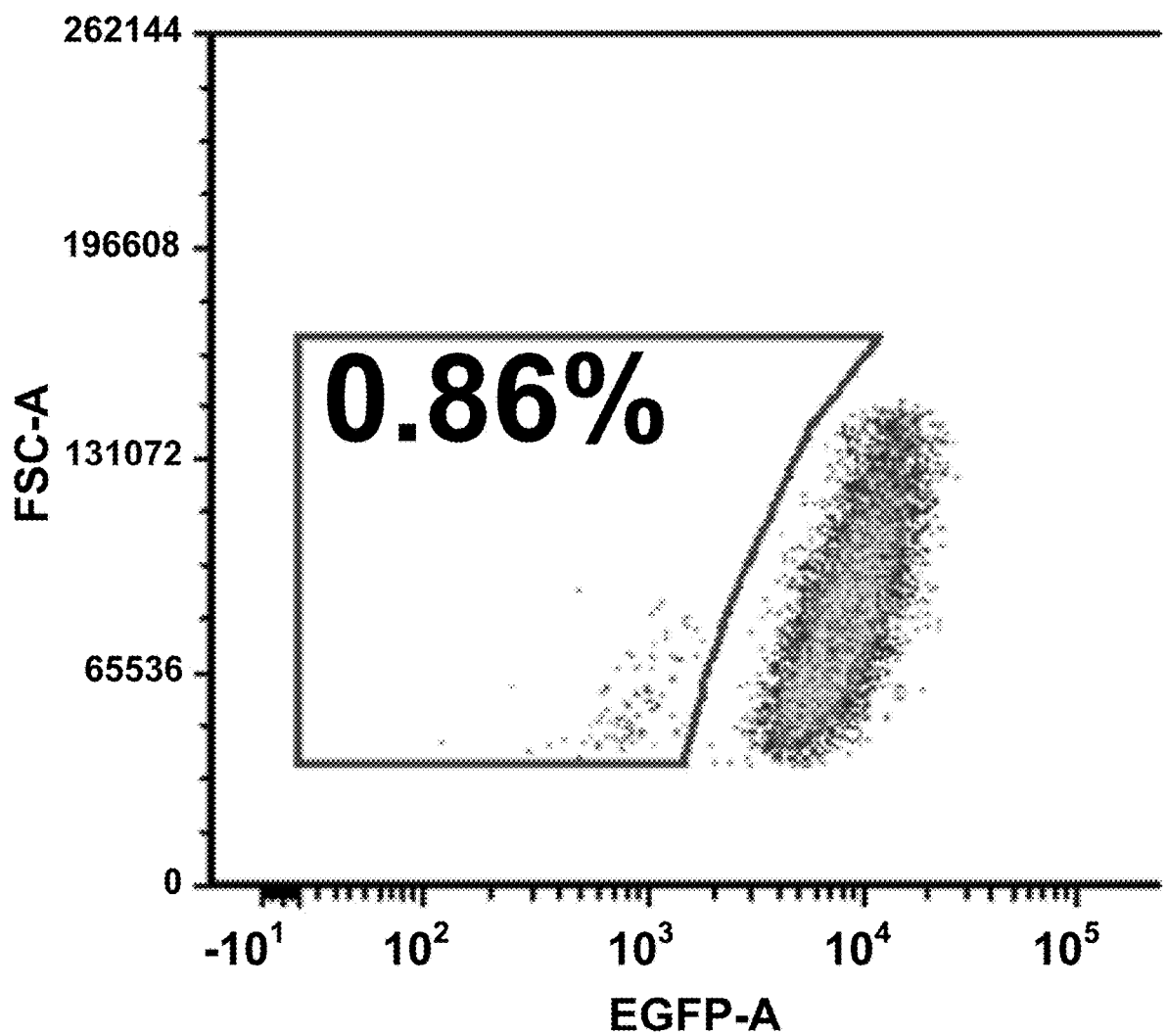
FIGS. 5C, 5D, and 5E illustrate disruption of an Oct4 enhancer in H1 hESC according to an embodiment of the present disclosure.
Figure 5D:
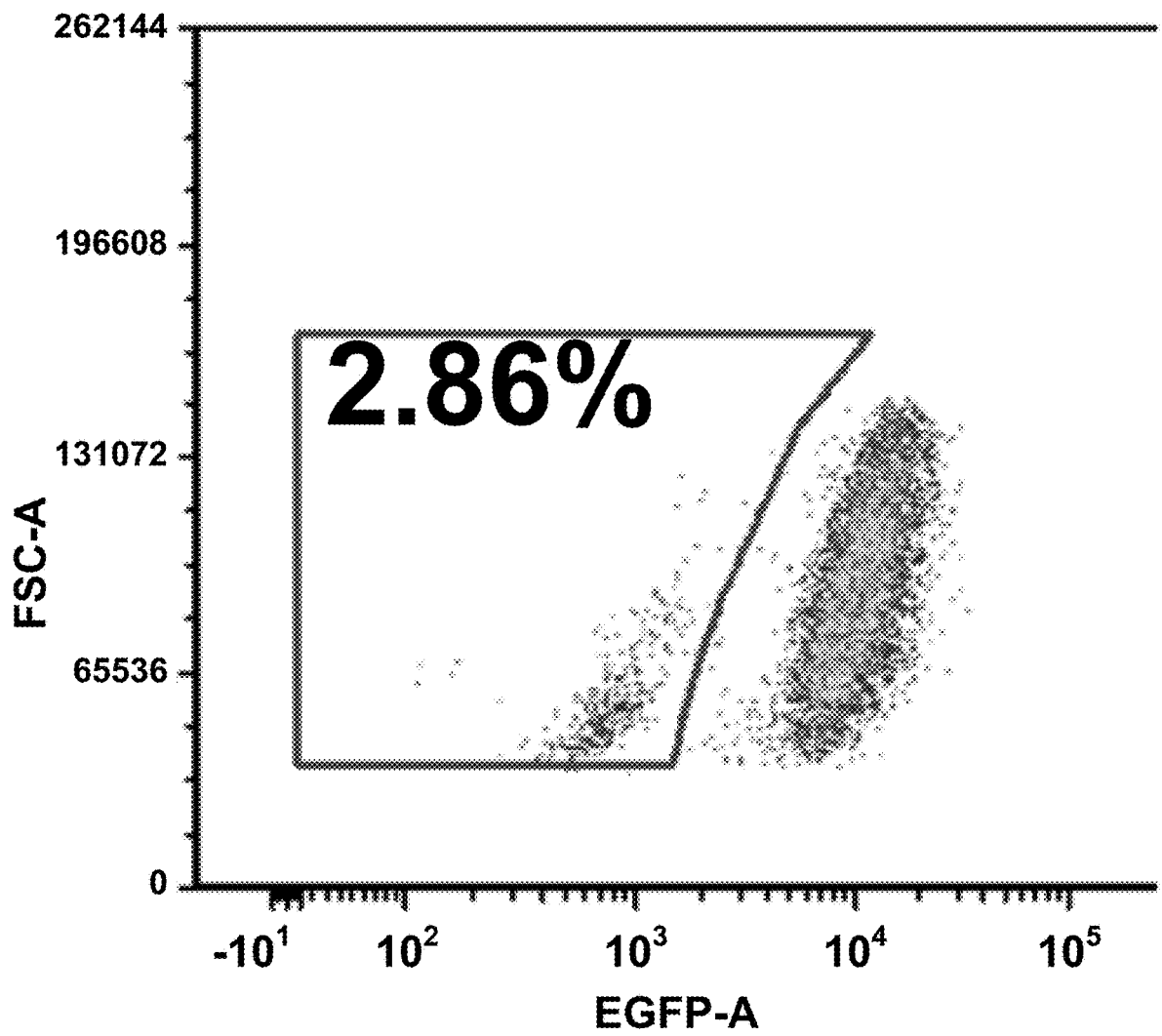
Figure 5E:
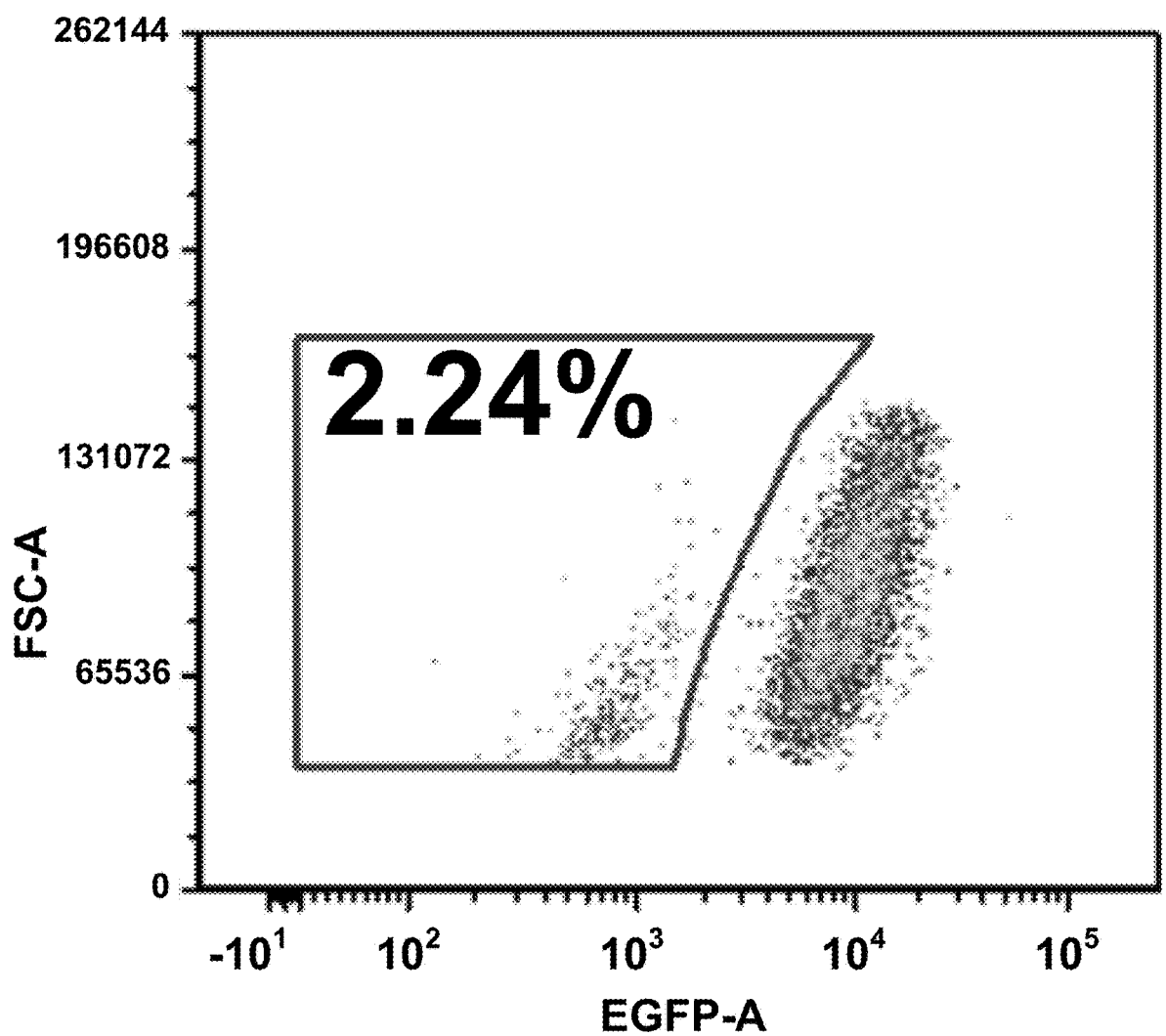

We further compared the cleavage efficiency of single-transcript TALENs in H1 hESC cells that had an IRES-EGFP marker behind the endogenous Oct4 (H1 Oct4-EGFP, WiCell). We targeted OREG1393087 "organic engineering target", a site that is known to be an important enhancer for Oct4 expression, with either traditional two-plasmid TALEN or single-transcript TALEN "organic engineering target", and monitored the Oct4 expression level in the stem cell population "workflow". As shown in FIGS. 5C-E, targeting the enhancer region using either TALEN produced an Oct4-reduced stem cell population. The activity produced by the single-transcript TALEN was comparable to that of the traditional TALEN.

Example IV—Full Automation of Single-Transcript TALEN Assembly on a Biological Foundry Many genomic studies may involve screening of a large number of targets which requires large-scale synthesis of TALENs to specifically disrupt these loci. Even though we have improved the efficiency and simplified the workflow of TALEN synthesis, it is still very tedious if not impossible to construct hundreds of these TALENs manually. Human errors and inconsistency will also jeopardize the quality of the library. Automation has been used to accelerate biological organic engineering by either reducing human interventions in individual steps, or completely eliminating human intervention using integrated systems (Esvelt et al., 2011, "A system for the continuous directed evolution of biomolecules," Nature, 472 (7344), p 499; Wang et al., 2009, "Programming cells by multiplex genome organic engineering and accelerated evolution," Nature, 460 (7257), p 894). The latter approach has demonstrated the great power of full automation by creating a large number of genetic variants in a short time period. To enable large-scale applications of TALENs such as genetic screening, we sought to fully automate the synthesis process "workflow" of TALENs. However, existing integrated platforms are extensively customized for specific tasks and difficult to reconfigure. It would not be efficient and economical to build a deeply customized system dedicated to TALEN synthesis. Instead, we applied a generalized Golden Gate assembly workflow implemented on iBioFAB.

Figure 7A:
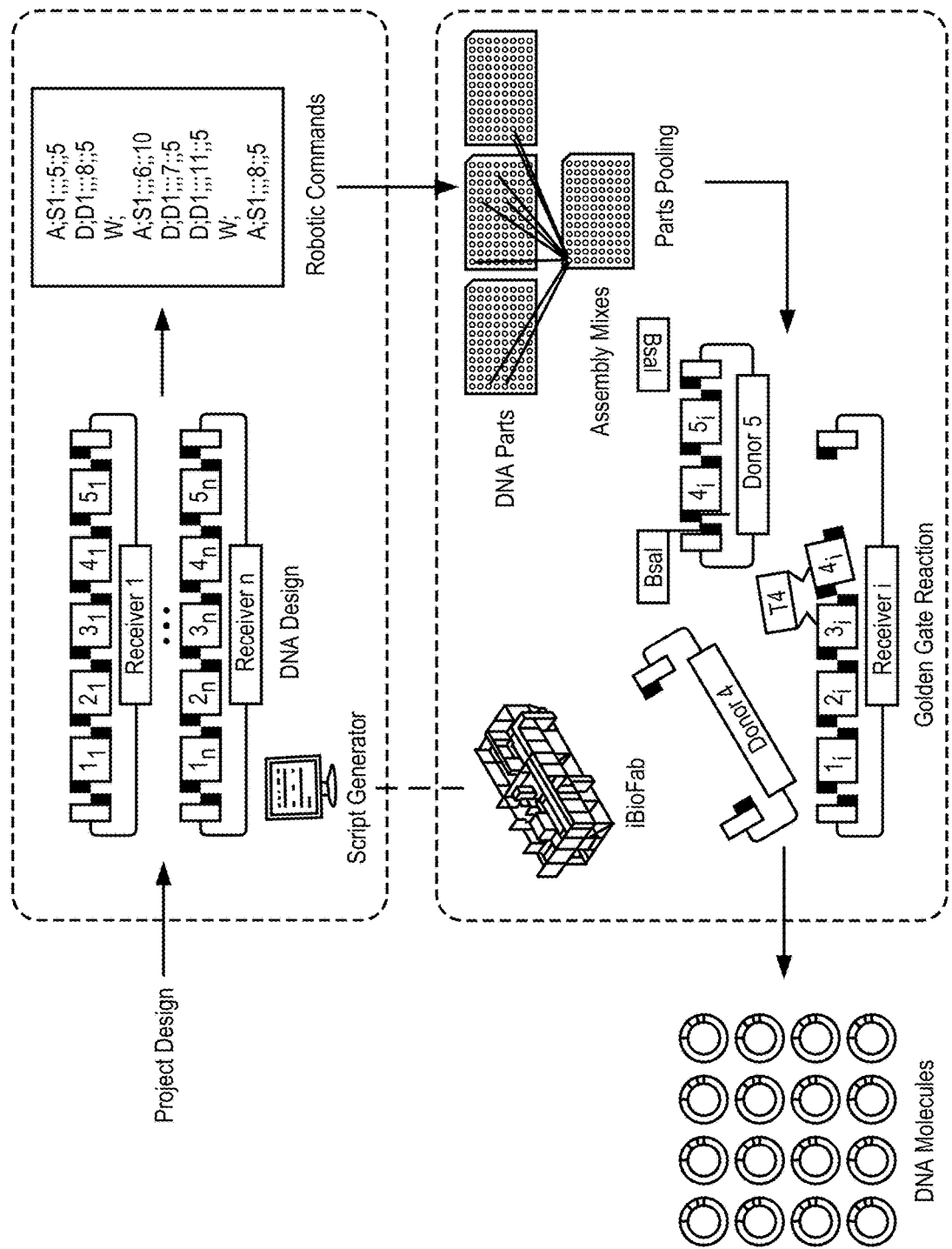
FIG. 7A illustrates general workflow for the DNA assembly pipeline based on Golden Gate method according to an embodiment of the present disclosure.
Figure 7B:
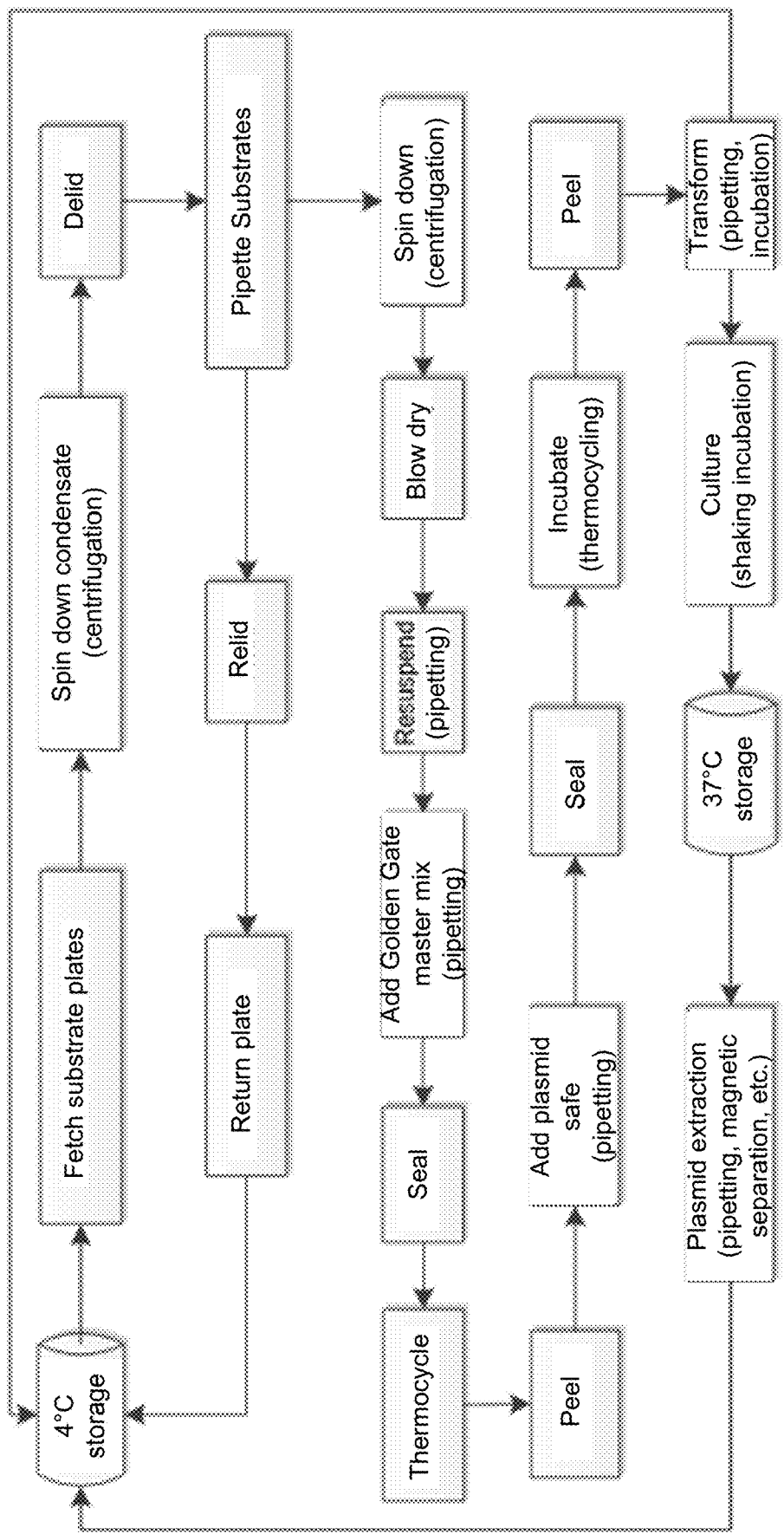
FIG. 7B illustrates a process flow diagram for the build step according to an embodiment of the present disclosure.

The iBioFAB "system" consisted of component instruments, a central robotic platform, and a modular computational framework (FIG. 6). Twenty devices "instruments", each in charge of a unit operation such as pipetting and incubation, were linked by two robotic arms "transporter" into various process modules such as DNA assembly and transformation, then further organized into workflows such as pathway construction and genome organic engineering (FIGS. 6A-C). An overall scheduler "scheduler" was developed to orchestrate the unit operations and allow hierarchical programming of the workflows (FIG. 6C). The iBioFAB was configured to perform a generalized automatic DNA assembly workflow where various kinds of DNA constructs "organic engineering targets" can be manufactured on-demand with Golden Gate method (Engler et al., 2008, "A one pot, one step, precision cloning method with high throughput capability," PLoS One, 3 (11), e3647). A sequence of unit-operations was designed to implement this workflow (FIG. 7A and FIG. 7B). To streamline the process, we developed Script Generator, a design tool that automatically converts DNA assembly "organic engineering targets" designs to experimental routines of mix-and-matching arbitrary DNA parts "unit operations". Script Generator then generates robotic commands for iBioFAB to conduct the complex pipetting work "unit operation". The pipetting routes "unit operations and/or transport paths" were also optimized to minimize tip and time consumption. The aspiration steps "unit operations" are combined as much as possible for the same substrate and dispensed into corresponding destination. Tips are loaded on demand from the storage carousel "physical storage medium" to the liquid handling station.

In this work, we adapted this DNA assembly workflow for synthesizing single-transcript TALENs "organic engineering targets". An extension that automated the DNA assembly design specifically for TALENs was added to Script Generator. Using such pipeline, the operator only needs to input the target DNA sequence "organic engineering target" to Script Generator, and iBioFAB "system" would perform the rest of TALEN synthesis "workflow" with minimal human intervention. It only requires the operator "user" to load reagents and consumables on a daily basis. Any arbitrary number between 1 to 192 TALEN pairs can be synthesized in each batch.

Example V—High-Throughput Synthesis of 192 Single-Transcript TALENs

To test the high-throughput synthesis pipeline "system", we fed 192 different human genomic target loci "organic engineering targets" to Script Generator "first device". iBio-FAB performed 3648 pipetting steps "from 444 different DNA parts and reagents within 17 hours at a reasonable material cost. By staggering batches, over 400 TALENs can be generated in a single day.

Figure 7C:
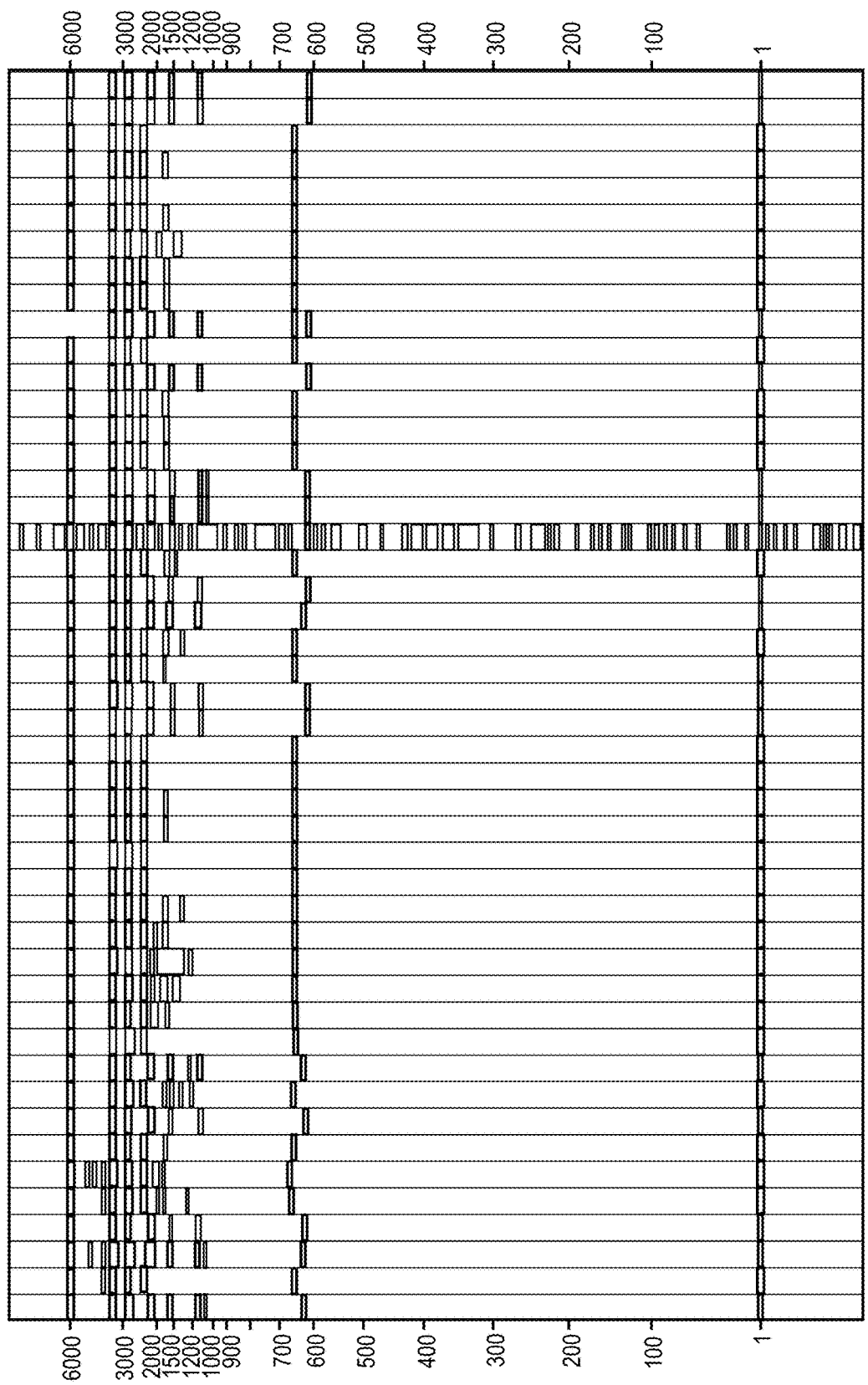
FIG. 7C and FIG. 7D illustrate verification of single-transcript TALENs synthesized in high throughput according to an embodiment of the present disclosure.
Figure 7D:
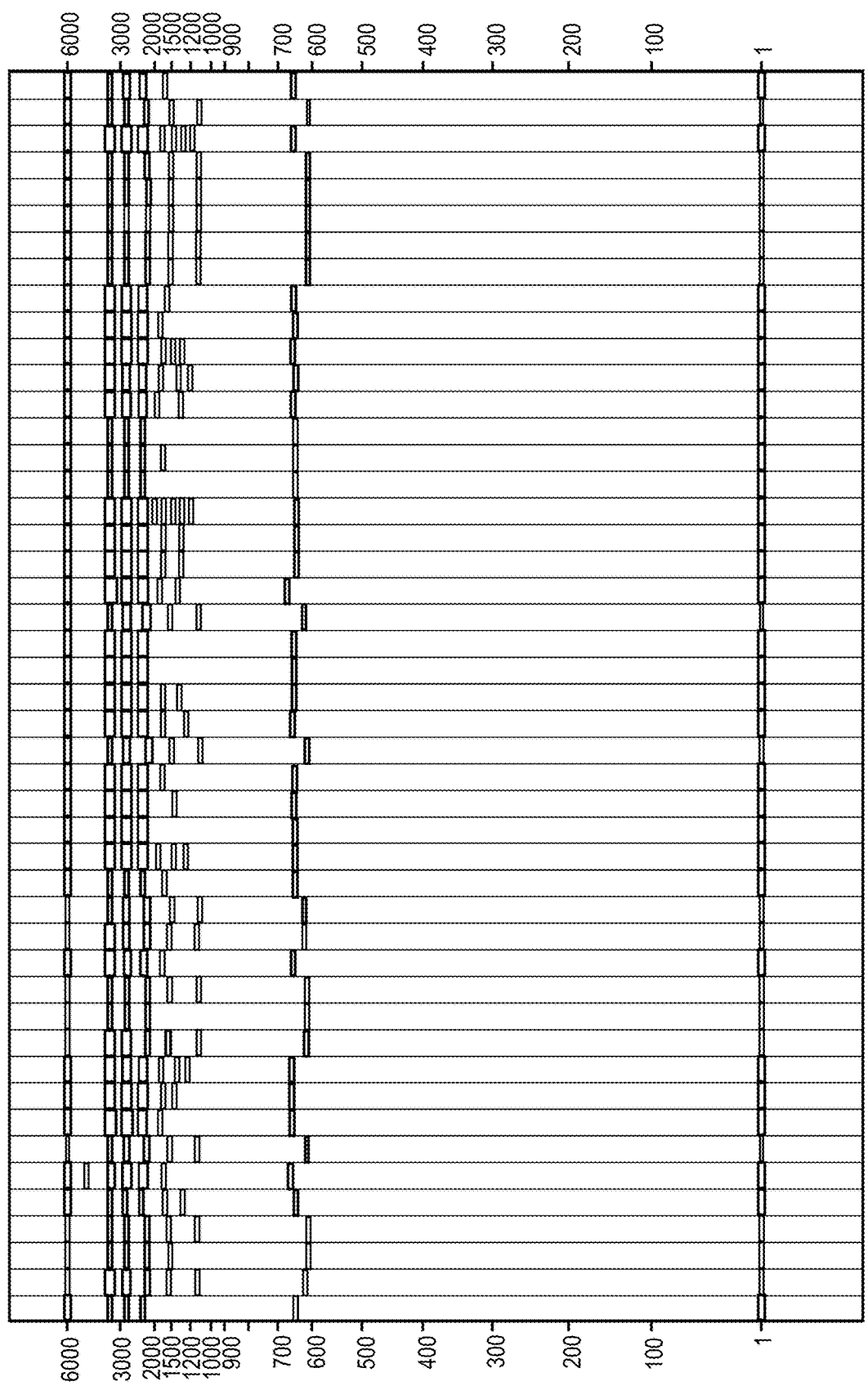

To evaluate the success rate of the synthesis, 94 randomly selected constructs "organic engineering targets" were verified by poly-clonal restriction digestion "workflow". All samples showed the correct digestion pattern (FIG. 7C and FIG. 7D) which corresponds to a success rate of at least 96.2% with 95% confidence based on binomial probability. For activity verification, we randomly selected 22 TALENs for T7E1 assay in HEK293T cells (Mashal et al., 1995, "Detection of mutations by cleavage of DNA heteroduplexes with bacteriophage resolvases," Nat Genet, 9 (2), p 177). Here, 15 of 22 samples showed cleavage activity. Since cleavage activity was known to be sequence dependent, the lack of activity for some sites was not unexpected (Cermak et al., 2011, "Efficient design and assembly of custom TALEN and other TAL effector-based constructs for DNA targeting," Nucleic Acids Res, 39 (12), e82). To eliminate the possibility of mis-assembly, we sequenced all the constructs that did not show cleavage activity. All sequencing reads aligned to the intended TALEN designs, indicating that the TALENs were correctly assembled (FIG. 12).

Besides TALEN, clustered regulatory short palindromic repeat (CRISPR)—Cas9 is another popular technology used in genome editing applications (Sander et al., 2014, "CRISPR-Cas systems for editing, regulating and targeting genomes," Nat Biotechnol, 32 (4), p 347). As opposed to using a specific protein to recognize DNA sequences, CRISPR utilizes RNA to perform the recognition through base pairing. Using a nucleic acid for targeting "organic engineering target" has many advantages, but most importantly, through the use of micro-array DNA synthesis, a large nucleic acid library is readily accessible. As such, even though TALEN had a two-year head start over CRISPR, multiple targeting and genetic screening were both first achieved using CRISPR (Shalem et al., 2014, "Genome-scale CRISPR-Cas9 knockout screening in human cells," Science, 343 (6166), p 84; Wang et al., 2014, "Genetic Screens in Human Cells Using the CRISPR-Cas9 System," Science, 343 (6166), p 80; Cong et al., 2013, "Multiplex Genome Engineering Using CRISPR/Cas Systems," Science, 339 (6121), p 819). However, due to its relatively short recognition sequence, 20 bp, off-target effect is a significant problem in CRISPR (Fu et al., 2013, "High-frequency off-target mutagenesis induced by CRISPR-Cas nucleases in human cells," Nat Biotechnol, 31 (9), p 822). In a genetic screening that targets structural genes, the off-target effect can be compensated by targeting multiple sites within the same gene, so that high confidence hit can be identified by looking for the enrichment of a set of sites instead of any single site. However, in the case where the functional DNA element is very small, e.g., a transcriptional enhancer, or a miRNA gene, there is simply not enough length to fit in multiple targeting sites. Furthermore, in the case of an enhancer, the target cut sites are transcription factor binding sites that are typically around 10 bp. Given the limited range for target selection, CRISPR may not be able to find a site that is sufficiently unique in the genome. Furthermore, given the small number of selectable sites for such screens, the level of confidence for any resultant hits will be low. A TALEN library, with a different off-target profile, can be used in conjunction with a CRISPR library to improve the confidence of any potential hits.

In conclusion, we have developed a scheme to synthesize TALEN pairs on a single vector in a one-pot reaction, which has substantially simplified the synthesis of TALENs while achieving outstanding success rate. An automated process was developed accordingly, and the resulted pipeline makes it possible to create large TALEN libraries at a reasonable cost and time frame.

Methods—iBioFAB iBioFAB "system" consists of a F5 robotic arm "transporter" (402) on a 5-meter track "transport path" (Fanuc, Oshino-mura, Japan), an Evo200 liquid handling robot "second transporter" (404) (Tecan, Mannedorf, Switzerland), two shaking temperature controlled blocks (Thermo Scientific, Waltham, MA), a M1000 microplate reader (406) (Tecan, Mannedorf, Switzerland), a Cytomat 6000 incubator (408) (Thermo Scientific, Waltham, MA), two Cytomat 2C shaking incubators (Thermo Scientific, Waltham, MA), three Multidrop Combi reagent dispensers (412) (Thermo Scientific, Waltham, MA), four Trobot thermocyclers (414) (Biometra, Gattingen, Germany), Vspin plate centrifuge (Agilent, Santa Clara, CA), a storage carousel (416) (Thermo Scientific, Waltham, MA), a de-lidding station (Thermo Scientific, Waltham, MA), an Alps plate sealer (410) (Thermo Scientific, Waltham, MA), a WASP plate sealer (Thermo Scientific, Waltham, MA), a Xpeel seal peeler (Brooks, Chelmsford, MA), and a label printer (418) (Agilent, USA). The liquid handling robot was equipped with an 8-channel independent pipetter, a robotic manipulation arm, a 96-channel pipetter, six Peltier temperature controlled blocks (Torrey Pine, Carlsbad, CA), two shakers (Q.Instruments, Jena, Germany), a light box, and a camera for colony picking "a plurality of instruments" (Scirobotics, Kfar Saba, Israel), as partially shown in FIG. 2.

Momentum (Thermo Scientific, Waltham, MA) was used to communicate with the peripheral devices, control the central robotic arm, and program process modules. Process modules defined the unit operations and sample transportation routes "transport path" between unit operations. Freedom Evoware (Tecan, Mannedorf, Switzerland) was used to control the liquid handling robot and program pipetting modules. Pipetting modules specifically defined the general procedure of pipetting on the liquid handling robot, such as labware fetching "executable instruction" from the central robotic arm "transporter", DNA part dispensing, reagent dispensing, and temperature controls "unit operations".

iScheduler and ScriptGenerator are programed in Visual Basic. iScheduler executes process modules by sending commands in Extensible Markup Language to Momentum. The ScriptGenerator converted user defined DNA assembly "organic engineering target" as permutations of parts to source and destination locations based on preloaded parts storage plate layouts. The corresponding pipetting routes "unit operations" were optimized by queueing the destination locations from the same source. Pipetting worklists were compiled accordingly and sent to Freedom Evoware to control aspiration, dispense, as well as tip change actions. Defined amount of each DNA part was aspirated and multi-dispensed without contacting the liquid in the destination "executable instruction". Tips were re-used as much as possible and changed when all destinations for the same source were dispensed. Constraints "interlocking condition" such as tip volume and maximum number of aspirations with each tip were also imposed in the algorithm.

Example VI—Plasmids

Based on the RVDs parts used in the previous work (Liang et al., 2014, "FairyTALE: A high-throughput TAL effector synthesis platform," ACS Synth Biol, 3 (2), p 67), a new library of TALEN stock plasmids were developed for the single plasmid design. The group for position 6 was replaced with LR_N-term_FokI_P2A+C-term constructs (FIG. 8A). Dual and single RVD parts with NN were supplemented into the stock library. The RVD and P2A fragments were inserted to a receiver plasmid (FIG. 8B) with human CMV promoter as well as last repeat, N terminus, and FokI domain for the second TALEN monomer.

Example VII—Golden Gate Assembly and Verification

Golden Gate DNA assembly was performed with the methods described in the previous work (Liang et al., 2014, "FairyTALE: A high-throughput TAL effector synthesis platform," ACS Synth Biol, 3 (2), p 67). Competent *E. coli* HST08 strain (Clontech, Mountain View, CA) was prepared with Mix & Go *E. coli* Transformation Buffer Set (Zymo Research, Irvine, CA). 2.5 µL of Golden Gate reaction products were first mixed with *E. coli* competent cells on a Peltier block held at 0° C. and incubated for 30 min. The cell plate was then transferred to a second Peltier block held at 42° C. by the plate manipulation arm. After 1-min heat shock, the cell plate was transferred back to the 0° C. block and chilled for 2 min. The transformants were recovered in LB broth (Becton, Dickinson and Company, Franklin Lakes, NJ) for 1 hr. The recovered cell suspensions were either plated on LB agar media with 100 µg/mL of ampicillin or used to inoculate poly-clonally LB liquid media supplemented with 200 µg/mL of carbenicillin. Plasmids were extracted from the poly-clonal cultures with MagJET Plasmid DNA Kit (Thermo Scientific, Waltham, MA) and restriction digested by EcoRI-HF (New England Biolabs, Ipswich, MA). The digestion products were analyzed by 1% agarose gel in low throughput or Fragment Analyzer (Advanced Analytical Technologies, Ankeny, IA) in high throughput. Selected plasmids were also verified by Sanger sequencing reactions (ACGT, Wheeling, IL) with 4 primers. The binomial probability confidence interval for assembly success rate was calculated with Clopper-Pearson method (Clopper et al., 1934, "The use of confidence or fiducial limits illustrated in the case of the binomial," Biometrika, 26, p 404).

Example VIII—Mammalian Gene Knockout and Verification

Human embryonic kidney (HEK) cell line HEK293T was transfected with randomly selected TALENs plasmids. HEK293T cells were used as they are easy to cultivate and transfect. Although no cell authentication or *mycoplasma* contamination tests were performed, we reason that the results of T7E1 assay is relatively insensitive to the cell line background. Cells were maintained in Dulbecco's modified Eagle's Medium (DMEM) (Corning Life Sciences, Tewksbury, MA) supplemented with 10% heat inactivated fetal bovine serum (Life Technologies, Carlsbad, CA) at 37° C. and 5% CO2 incubation. One day prior to transfection, 293T cells were seeded into 12-well BioCoat Collagen-I coated plates (Corning Life Sciences, Tewksbury, MA) at a confluency of ~50%. Transfections were performed with FuGENE HD Transfection Reagent (Promega, Madison, WI) according to the manufacturer's protocols. Briefly, for each well of the 12-well plate, 1 g of clonally purified TALEN plasmid was first diluted in Opti-MEM (Life Technologies, Carlsbad, CA) to a total volume of 100 L. After addition of 3 L Fugene HD reagent and incubation at room temperature for 5 min, the mix was added onto the cells. Cells were harvested at 60 hours post-transfection. The genomic DNA was extracted with QuickExtract DNA Extraction Solution (Epicentre, Madison, WI).

The cleavage efficiency was evaluated by T7E1 assay (Mashal et al., 1995, "Detection of mutations by cleavage of DNA heteroduplexes with bacteriophage resolvases," Nat Genet, 9 (2), p 177). DNA amplicons were designed to have a length of 400-1000 bp flanking the nominal cleavage site by a custom developed Visual Basic script. It searches the genome sequence within a given range for a pair of primer binding sites to avoid off-targets, long stretches of GC, AT, or any single type of nucleotide. End nucleotides, GC contents, and melting temperatures were optimized. The relevant genome sequences were downloaded by querying UCSC DAS server (www.genome.ucsc.edu/cgi-bin/das/) while off-target check was performed by querying GGGenome server (www.gggenome.dbcls.jp/). The PCR amplification was conducted with Q5 polymerase (New England Biolabs, Ipswich, MA) and annealing temperature touchdown (65-55° C. for 10 cycles, 55° C. for 20 cycles). In the cleavage assay, 200 ng of purified amplicon in 10 µL NEB Buffer 2 was first denatured and renatured (95° C., 5 min; 95-85° C. at -2° C./s; 85-25° C. at ~0.1° C./s; hold at 4° C.). 1OU of T7 Endonuclease I (New England Biolabs, Ipswich, MA) was added and incubated at 37° C. for 15 min. The reaction was stopped by adding 1 µL of 0.5M EDTA. The digestion products were analyzed by Fragment Analyzer (Advanced Analytical Technologies, Ankeny, IA).

Example IX—Oct4 Down-Regulation Assay

TALEN constructs under evaluation were transfected into H1-Oct4-EGFP stem cells (WiCell, Madison, WI) by nucleofection according to manufacturer's recommendations. After optimization, we settled on the P4 Primary Cell 4D-Nucleofector Kit, and program CA-137 on the 4D-Nucleofector (Lonza, Cologne, Germany). Cells were passaged one day after nucleofection, and were harvested on the fourth day after nucleofection. After harvest, the cells were counted and stained using Alexa Fluor 647 conjugated SSEA4 antibody (Life Technologies, Carlsbad, CA) at a concentration of 5×105 cells in 50 µL PBS with 2% BSA and 2.5 µL SSEA4 antibody. The cells were stained in the dark at room temperature for 30 min, and washed 3 times in PBS before flow cytometry analysis. During analysis, the stem cell population was first selected by gating for the SSEA4 positive cells. Within this population, we then look at the spread of EGFP expression, and gate for the EGFP-reduced population.

Figure 2A:
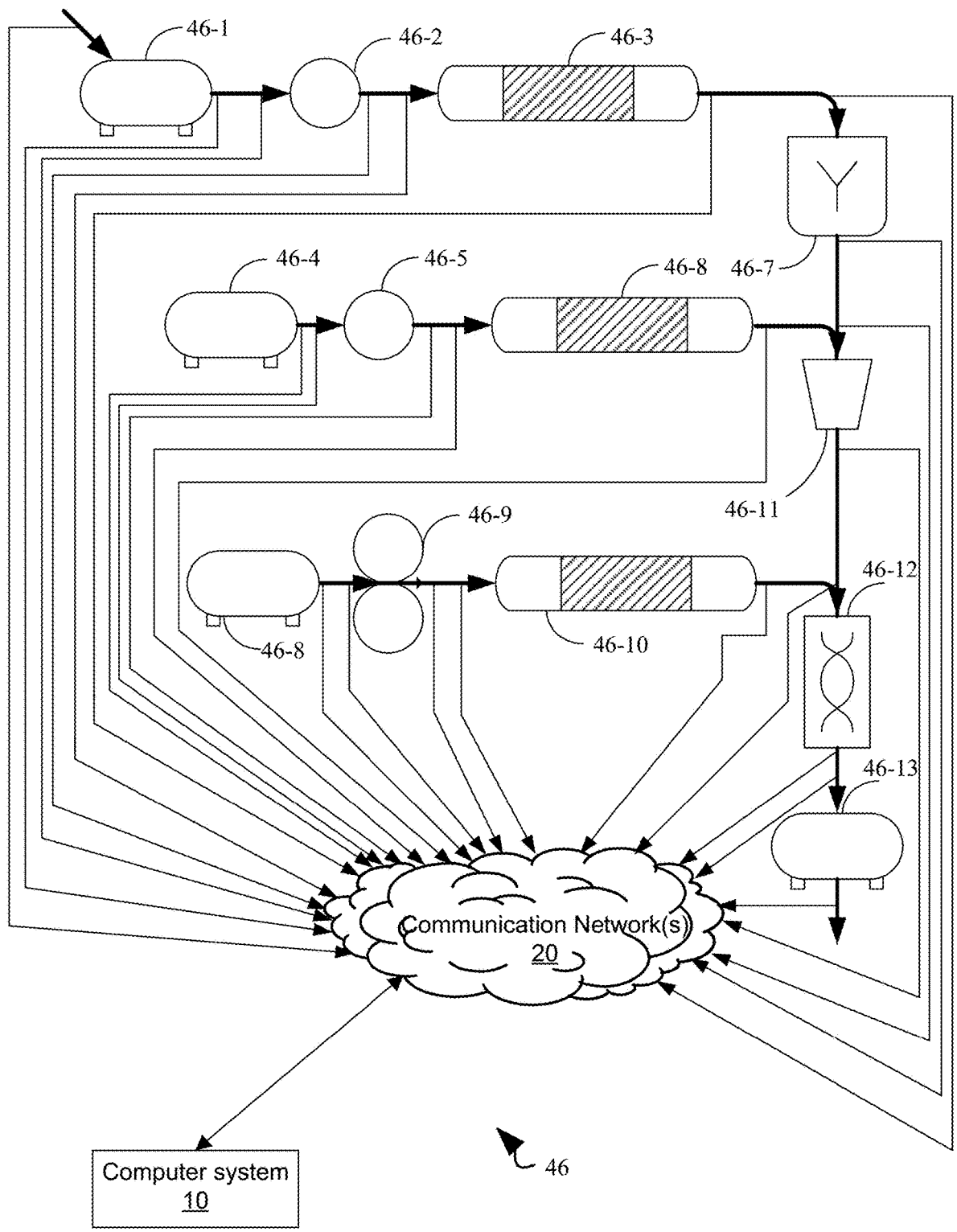
FIGS. 2A, and 2B illustrate a system topology and hardware layout in accordance with various embodiments of the present disclosure.
Figure 2B:
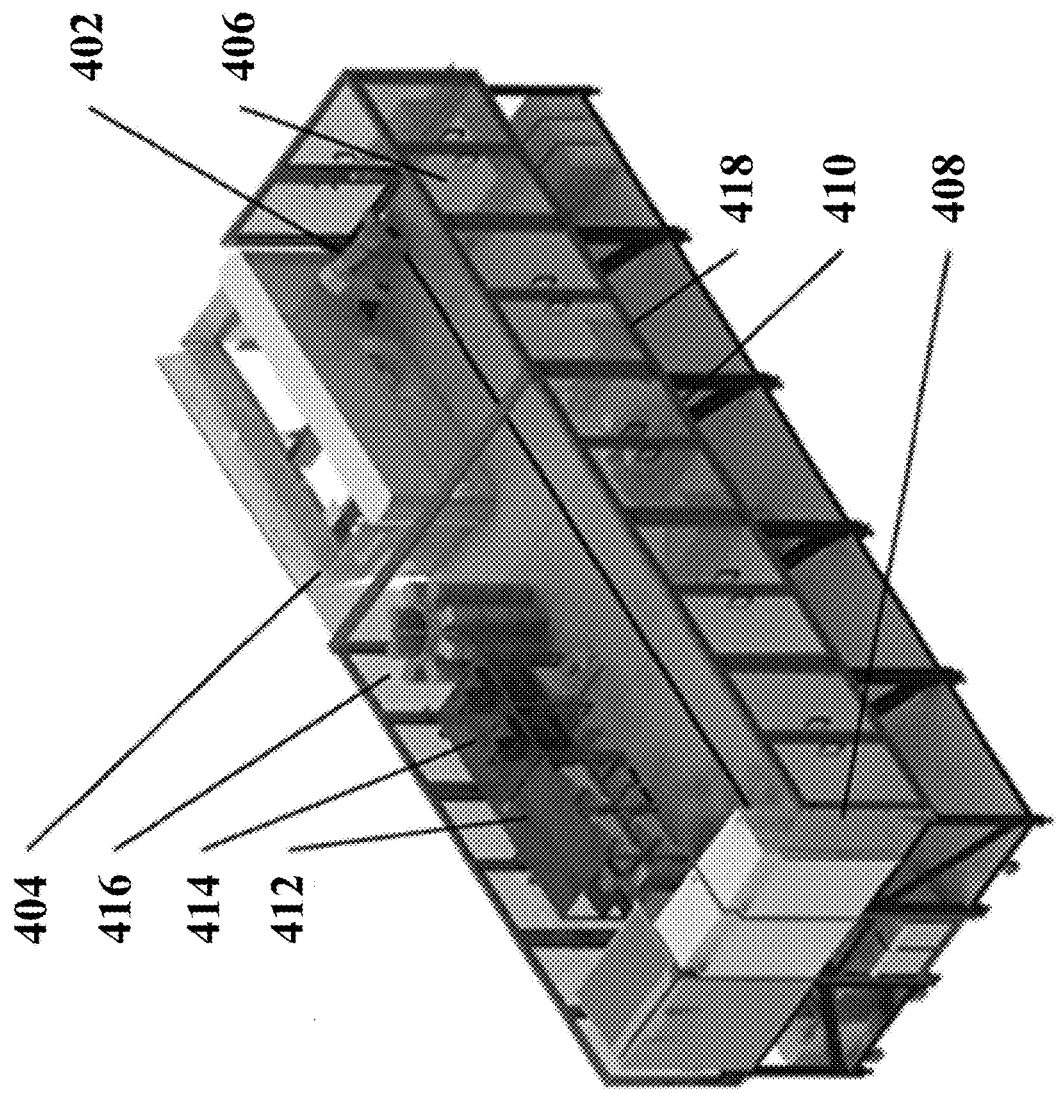

FIG. 2 illustrates an exemplary layout of iBioFAB's hardware. In an exemplary embodiment, iBioFAB has two robotic arms "transporters". A centralized 6-degree-of-freedom arm "transporter" on a 5-meter track is used to transport labware between instruments "transport path". A 3-degree-of-freedom arm "second transporter" moves labware inside the liquid handling station.

FIG. 4 illustrates a design and preliminary test of single-transcript TALEN synthesis "organic engineering target". FIG. 4A depicts the overall design, wherein both TALENs were transcribed as one mRNA, but sliced to separate proteins in translation as a P2A sequence was inserted between the open reading frames. FIG. 4B depicts the assembly scheme. A library of all possible combinations of single and dual TALE repeats "organic engineering targets" were pre-assembled with standardized Golden Gate linkers for each position. Thus, each TALEN monomer can target 8 to 15 nucleotides "organic engineering targets" with a mix of single and dual repeats. Repeats for both monomers as well as the LR-C-terminus-Fok-I-P2A-N-terminus fragment are assembled in a single Golden Gate assembly reaction. LR: last repeat. Term.: terminus. FIG. 4C illustrates a test assembly of a single-transcript TALEN pair. 28 independent clones were picked and digested by PvuI and StuI. All had correct digestion pattern. Arrows indicate the correct digestion pattern.

FIG. 5 illustrates a functional test of single-transcript TALENs. FIG. 5A depicts single-transcript expression of a TALEN pair. Two distinctive TALEN pairs were expressed in HEK293T cells with the single-transcript design. TALEN monomers showed visible bands on Western blot while no band for the size of uncleaved doublet was detected. FIG. 5B depicts genome editing in HEK293T cells. Single-transcript TALENs (STTLN) were compared against the traditional dual plasmid TALENs (TDTLN) by targeting BRCA2 as well as ABL1 sites in HEK293T cells. T7E1 assay was performed to detect the indel introduced by TALEN cleavage and NHEJ. The STTLN transfected samples showed comparable cleavage efficiency to TDTLN transfected samples. CTRL: sample with no TALEN transfection served as negative control. FIGS. 5C-E depict disruption of an Oct4 enhancer in H1 hESC. Flow cytometry was used to quantify the GFP expression level in H1-Oct4-GFP cells. The gated population had lower than normal GFP expression. Left: control population without enhancer disruption, middle: enhancer disrupted by traditional 2-plasmid TALEN, right: enhancer disrupted by single-transcript TALEN.

FIG. 6 depicts an overview of the iBioFAB system. FIG. 6A depicts a breakdown of unit operations according to an exemplary embodiment of the present disclosure. FIG. 6C illustrates an exemplary control hierarchy of iBioFAB. Process modules are developed in the system control GUI. iScheduler is in charge of workflow level control. Script Generator generates pipetting routes for the liquid handling GUI. Process modules can be quickly recombined to compose different workflows. Arrows indicate flows of processes or samples. A user can choose to intervene at any time, such as moving a sample, instead of the transporter or can process samples, such as performing a unit operation, instead of peripheral devices. Typically, samples or organic engineering targets are processed in batches. Multiple batches can be scheduled and staggered to be processed in parallel. In the programming interface, a user programs workflows with pre-developed and tested modules or sub-workflows. As previously described, the workflows define the dependency of unit operations for sample batches. The user designs bio-systems based on the organic engineering targets with help of a BioCAD. The designs are further converted to experimental plans by Workflow Generator, which can integrate the ScriptGenerator therein. In some embodiments, Workflow Generator only generates sample level experiment scripts that will be used as parameters and/or data by a transporter. In some embodiments, the Workflow Generator assists programing other unit operations or workflows. Nested sub-workflows, loops, and forks are allowed in workflows. These structures are then linearized for the scheduler. In case of large discrepancies between an actual runtime and schedule, or when triggered by a user, the workflow will be rescheduled except for the steps to be executed immediately. Both actions and micro-steps or executable instructions are abstracted for unit operations and defined in unit operation definitions. They are not specific to any models of instruments. The drivers map micro-steps to commands used in specific instruments.

FIG. 7 depicts a fully automated synthesis of TALEN libraries. FIG. 7A depicts a general workflow for the DNA assembly pipeline based on Golden Gate method. Script generator converted project design ideas such as permutations of DNA parts to assembly designs with appropriate extensions and further robotic commands for pipetting the stock plasmids to DNA mixes. In Golden Gate reactions, Type IIs restriction enzymes like BsaI generated a set of standard pre-characterized 4-bp single strained ends as linkers. The corresponding linkers annealed and were ligated by T4 ligase. FIG. 7B depicts a process flow diagram for the build step. Unit operations employed were marked in blue. FIG. 7C and FIG. 7D depict verification of single-transcript TALENs synthesized in high throughput. 94 samples were randomly selected from the 192 TALEN pairs synthesized in the full batch test. Each plasmid sample encoding a pair of TALENs was extracted from a polyclonal E. coli cell culture and restriction digested. The fragment sizes were analyzed by capillary electrophoresis. The digestion pattern was simulated.

An exemplary summary of efficiency, throughput, and cost of such a biofoundry have shown to produce approximately 400 TALEN pairs per day, with approximately one hour of human labor required per day.

Figure 8B:
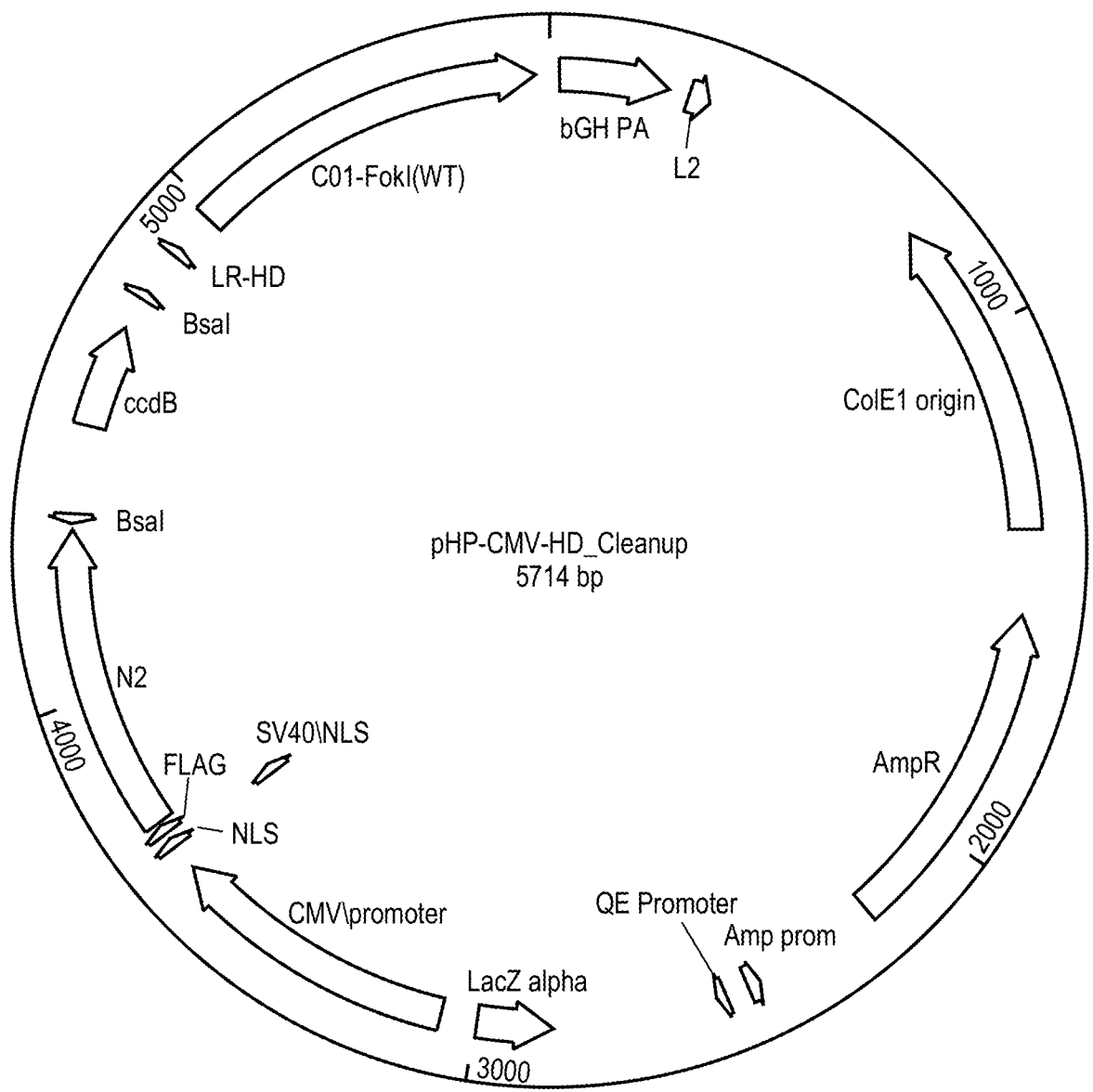

FIG. 8A and FIG. 8B depict a plasmid design for single plasmid TALEN assembly.

FIG. 8A depicts a P2A insert. It contained the last repeat, C-terminus, and FokI of the first TALEN monomer as well as the N-terminus of the second monomer. The two monomers were separated by a P2A sequence: GGCAGCG-GAGCTACTAACTTCAGCCTGCTGAAGCAGGCTG-GAGATGTGGAGGAGAA CCCTGGACCTGGCATG (SEQ ID. No.: 1). FIG. 8B depicts a CMV receiver. The RVD inserts replaces ccdB fragment during Golden Gate reaction. The ccdB site was flanked by N-terminus of the first TALEN monomer and last repeat along with C-terminus and FokI domain of the second monomer. A human CMV promoter is used to express both monomers. Four versions of the P2A insert as well as the CMV receiver with different last repeats were constructed.

Figure 9A:
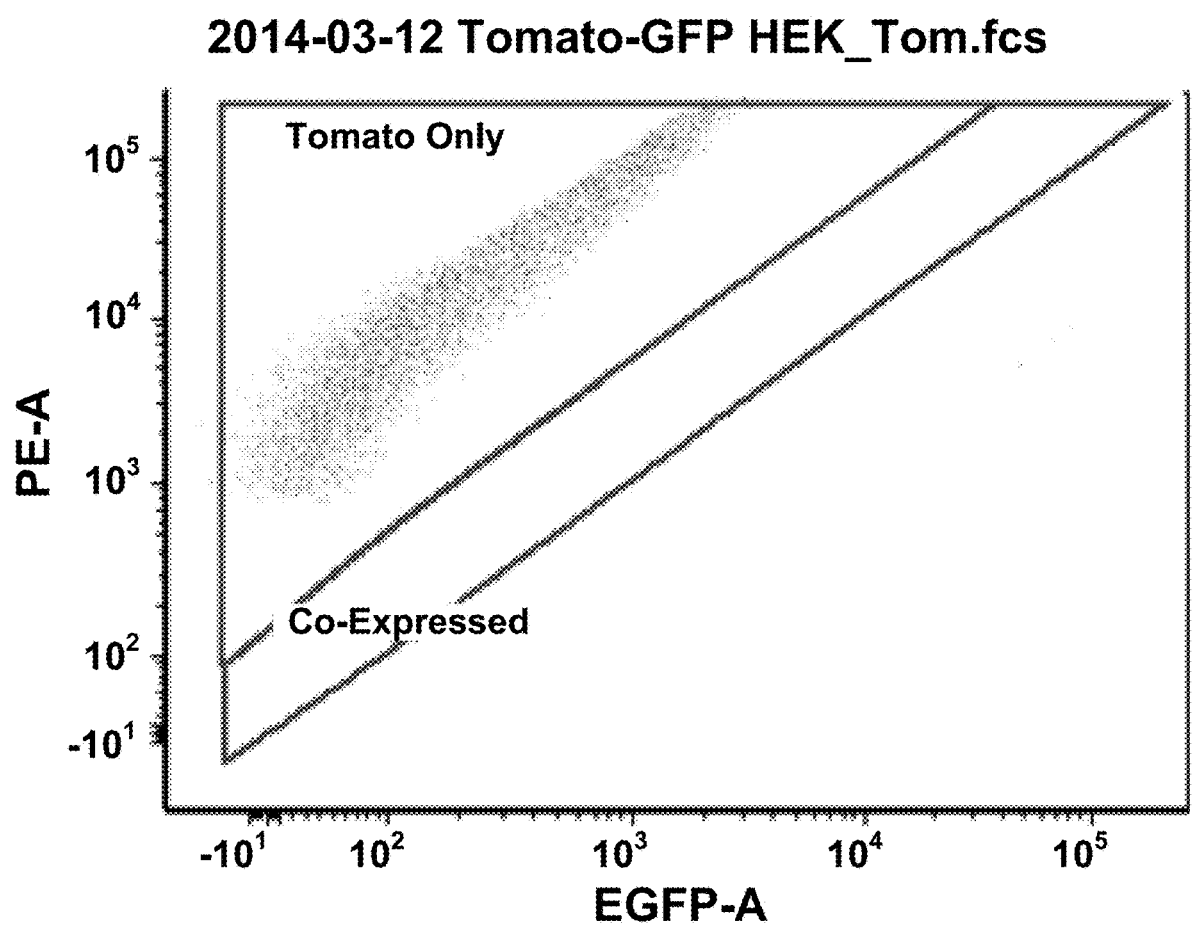
FIGS. 9A, 9B, 9C, 9D, 9E, 9F, 9G, and 9H illustrate disrupting EGFP in HEK293 cells according to an embodiments of the present disclosure.
Figure 9B:
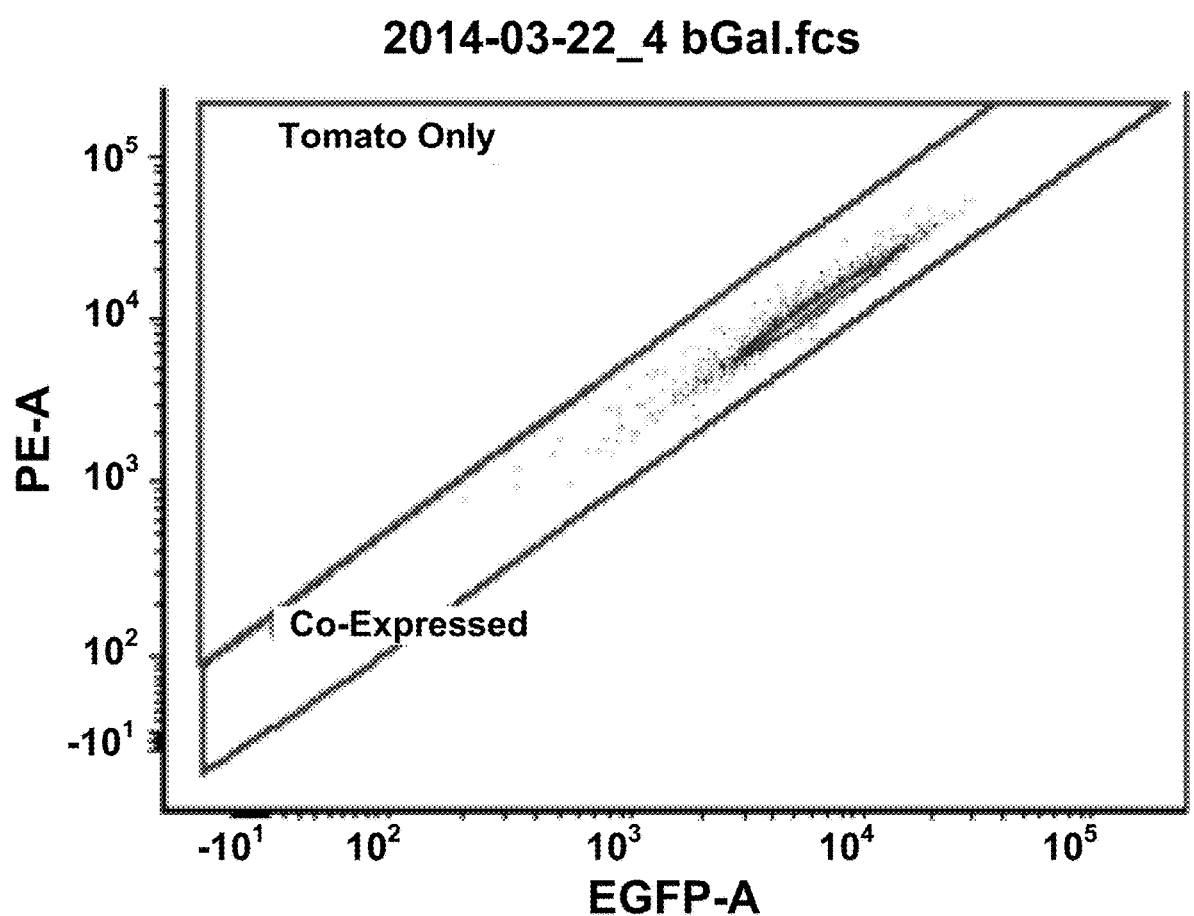
Figure 9C:
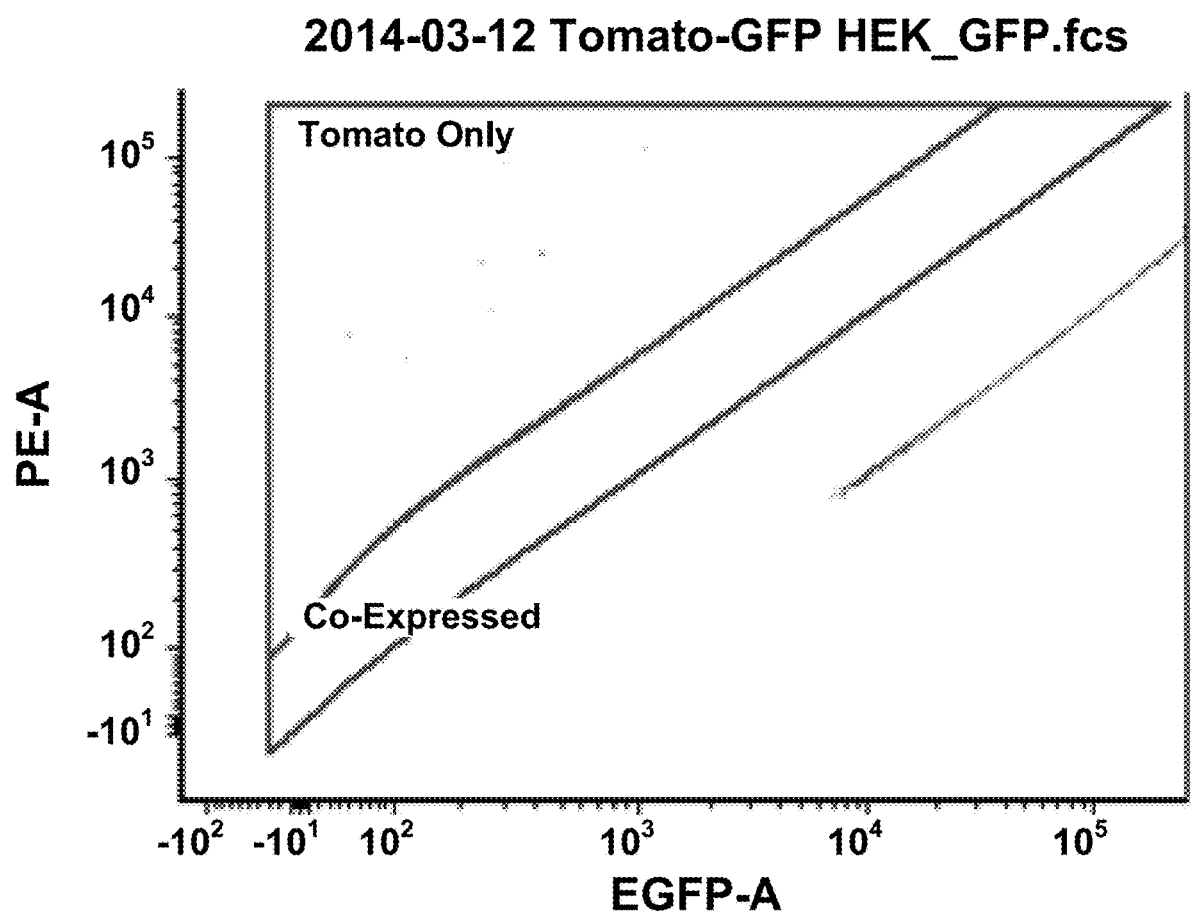
Figure 9D:
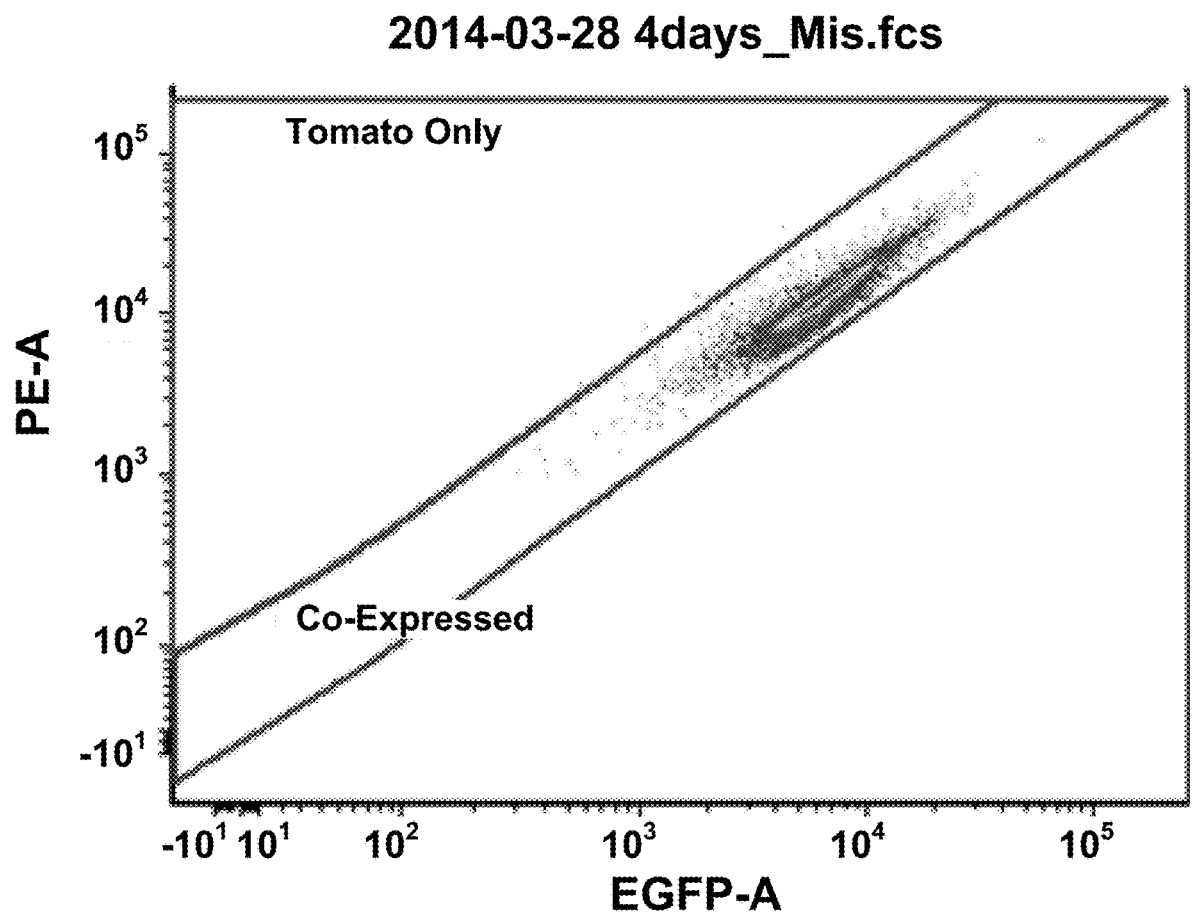
Figure 9E:
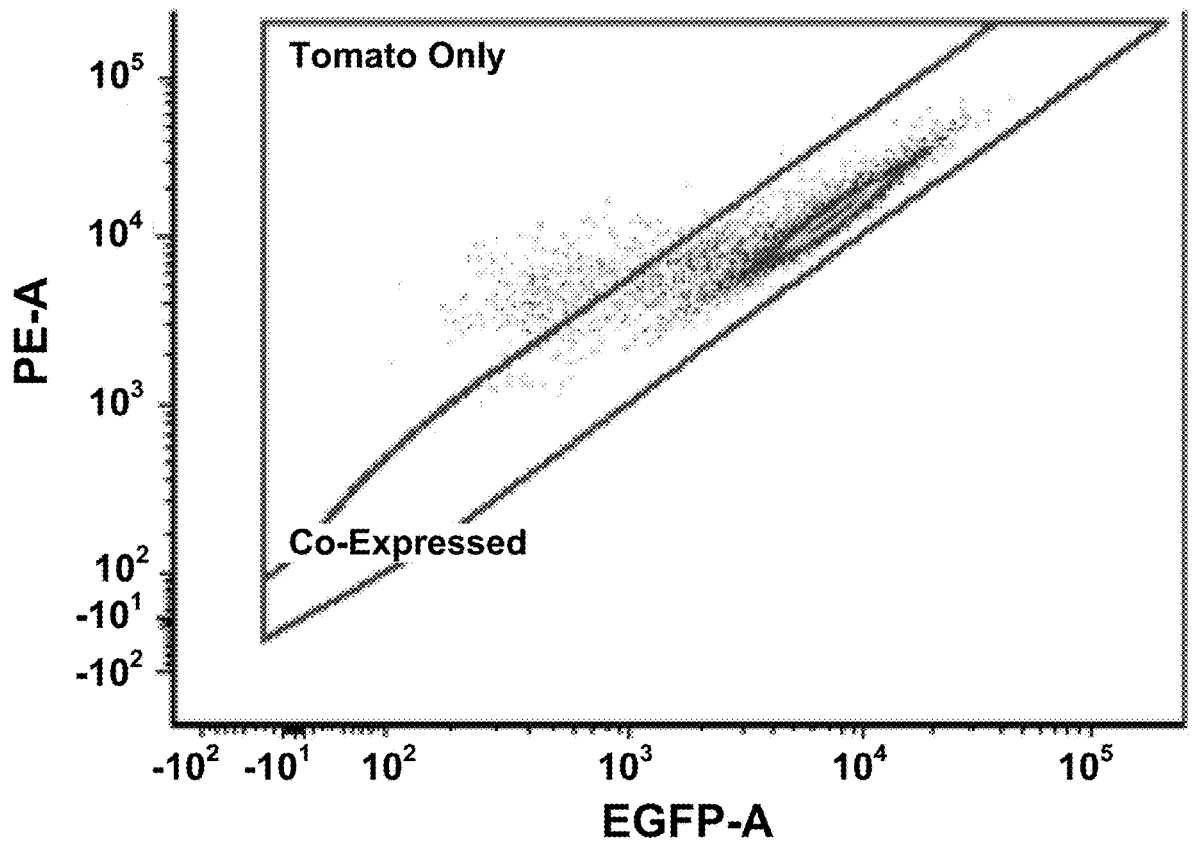
Figure 9F:
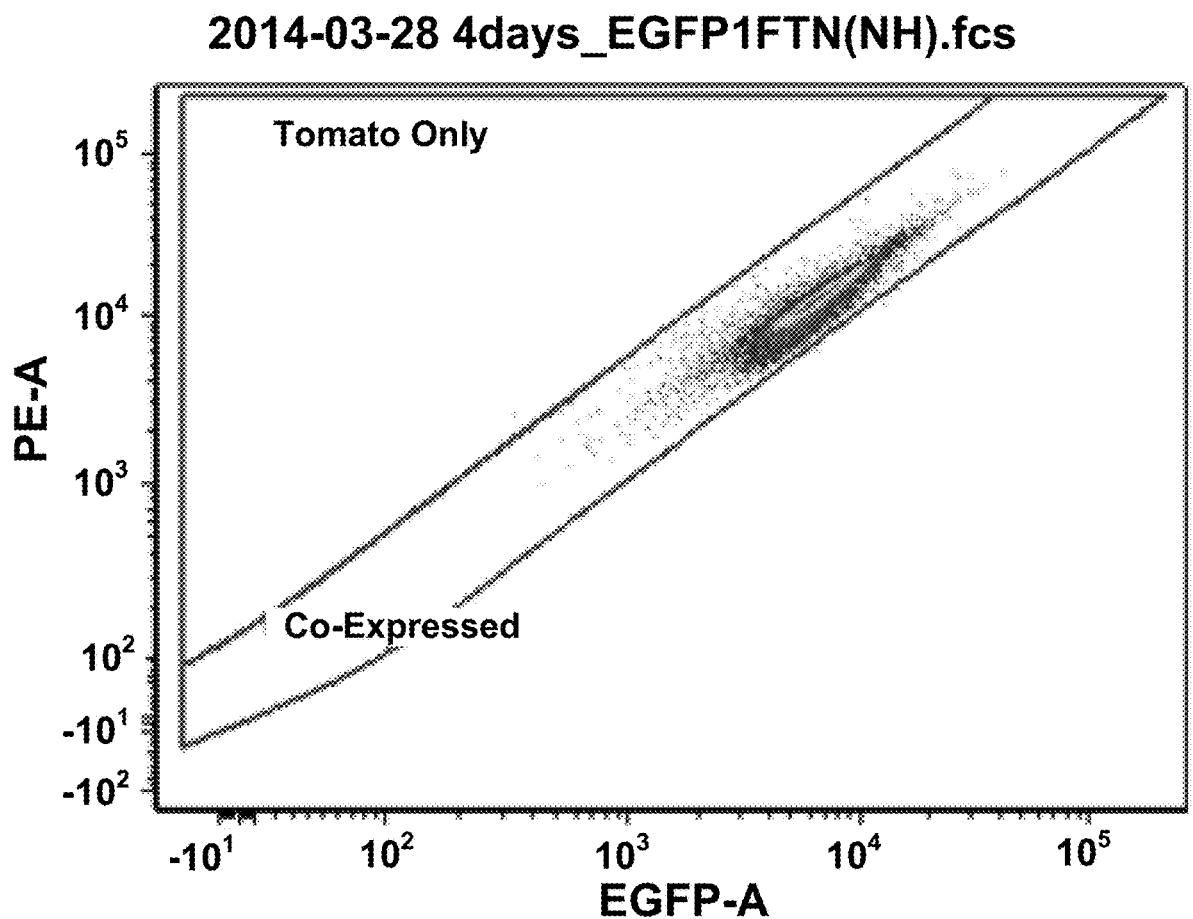
Figure 9G:
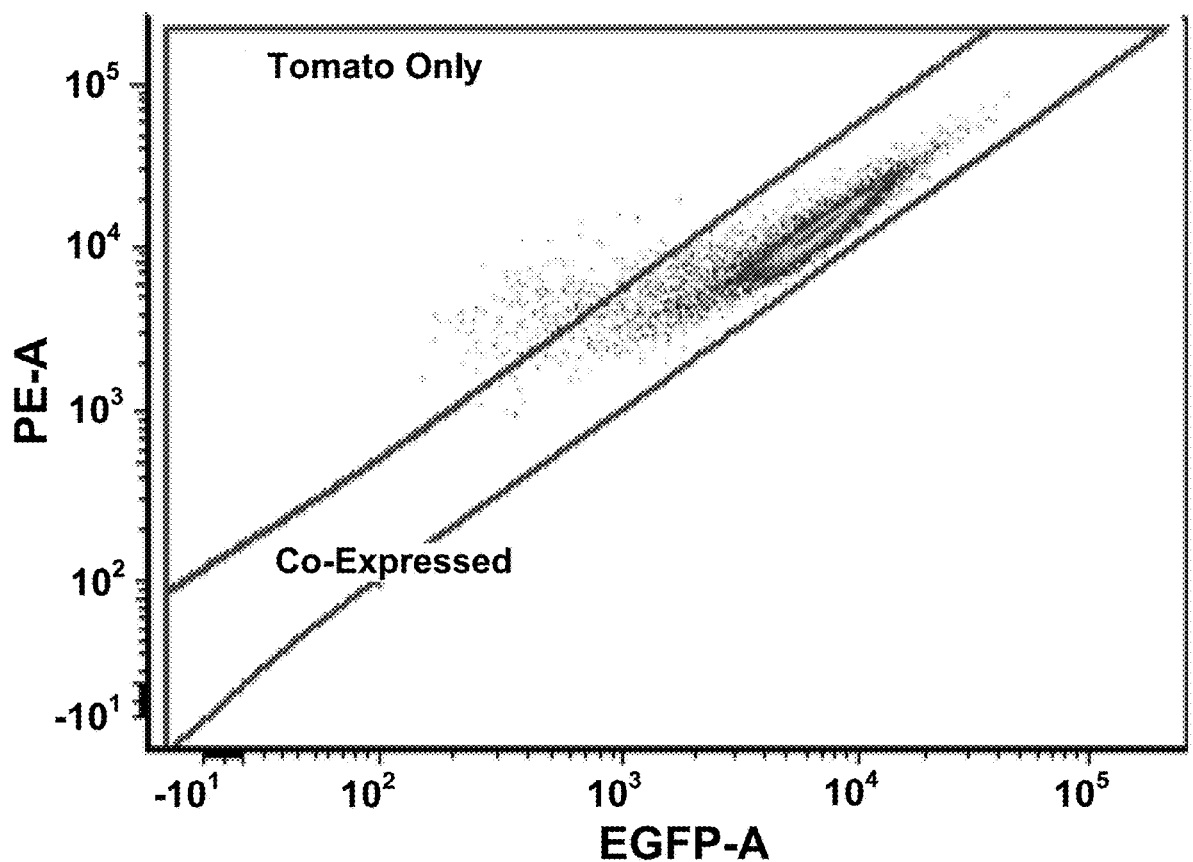
Figure 9H:
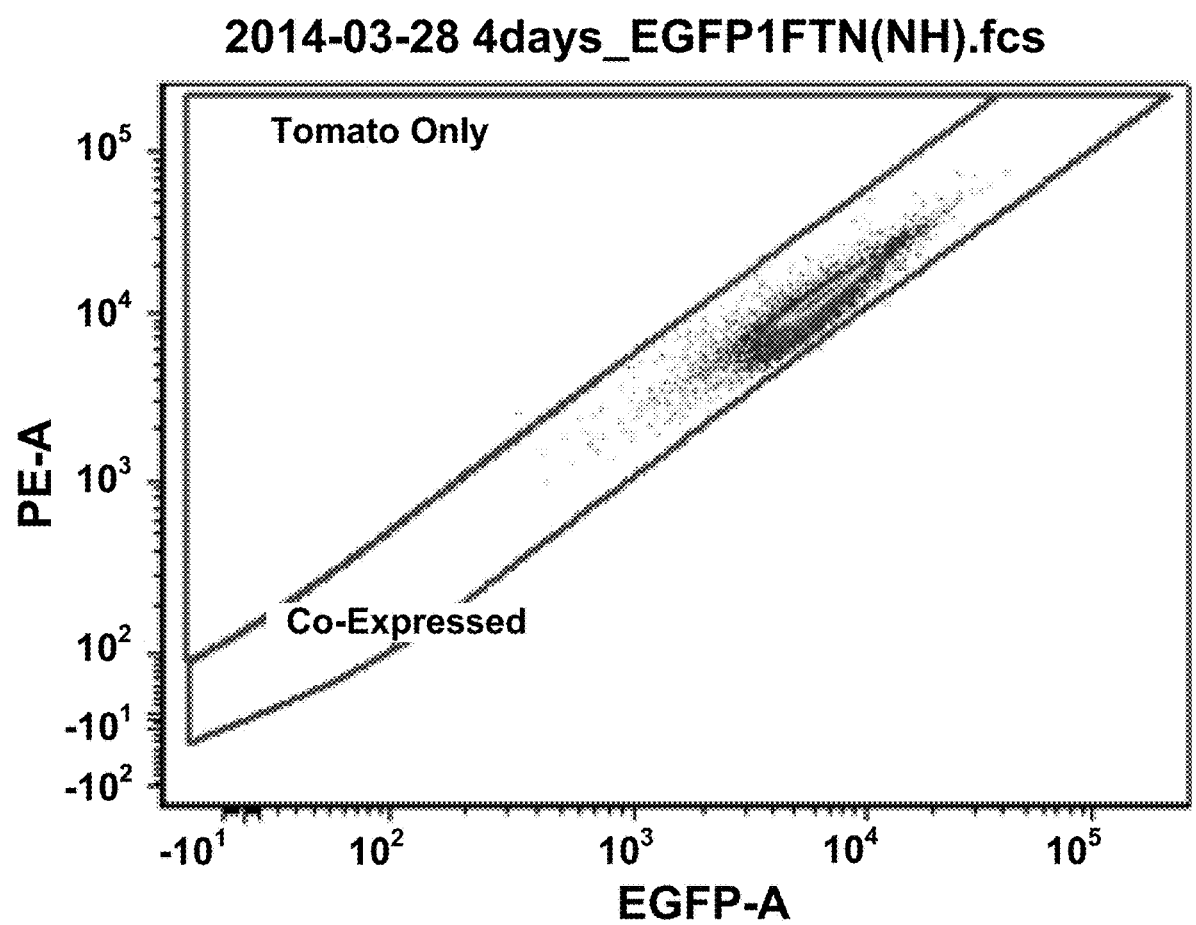

FIGS. 9A-H depict disrupting EGFP in HEK293 cells. A EF1a-tdTomato-P2A-EGFP cassette is stably expressed in HEK293T cells as a reporter system. TALENs are designed to cleave the EGFP fragment. tdTomato is used to exclude the non-expressive cells. FIG. 9A depicts cells expressing tdTomato only. FIG. 9A depicts cells expressing both tdTomato and EGFP, split by a P2A sequence. FIG. 9A depicts cells expressing EGFP only. FIG. 9A depicts negative control with TALEN targeting sequences other than EGFP. FIG. 9A depicts 2-plasmid TALEN targeting EGFP with NN for guanine. FIG. 9A depicts 2-plasmid TALEN targeting EGFP with NH for guanine. FIG. 9A depicts single-transcript TALEN targeting EGFP with NN for guanine. FIG. 9A depicts single-transcript TALEN targeting EGFP with NH for guanine. The results indicate that 1) single-transcript TALEN has comparable efficiency as the 2-plasmid TALEN and 2) TALENs with NN has better efficiency than NH.

FIG. 11 depicts a list of substrates. The nucleotide target of each DBD is indicated with A, T, G, C, or D, denotes a RVD of NI, NG, NH, HD, or NN respectively. In the substrate plasmids, the DBD(s) are flanked by appropriate 4-bp junctions so that they can be assembled in appropriate positions in the receiver plasmids by Golden Gate reaction. 5* substrates can be used to bridge Position 4 and 8 directly resulting in a shorter assembly if necessary. A, T, G, and C in P2A and Receiver substrates denotes the targeted nucleotide by the last repeats of TALENs. CMV indicates the CMV promoter used in this specific study while other promoters can be used by supplementing new substrates to the library. A yellow cell shows the substrates adapted from the previous work (Liang et al., 2014, "FairyTALE: A high-throughput TAL effector synthesis platform," ACS Synth Biol, 3 (2), p 67) while the rest of substrates were supplemented in this study.

FIG. 12 depicts a list of results from T7E1 assay. HEK293T cells were transfected with TALENs targeting 22 randomly selected genomic loci. Genomic DNA samples extracted from polyclonal post-transfection cultures were used for T7E1 assay. Asterisks "*" denote TALENs showing no cleavage activity were DNA sequencing-verified and aligned with the design.

REFERENCES CITED AND ALTERNATIVE EMBODIMENTS

For convenience in explanation and accurate definition in the appended claims, the terms "upper", "lower", "up", "down", "upwards", "downwards", "inner", "outer", "inside", "outside", "inwardly", "outwardly", "interior", "exterior", "front", "rear", "back", "forwards", and "backwards" are used to describe features of the exemplary embodiments with reference to the positions of such features as displayed in the figures.

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1 or 2 and/or described in FIG. 3. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of implementing one or more workflows: at a device comprising one or more processors, memory storing one or more programs for execution by the one or more processors, a controller, a transport path, a communications interface in electrical communication with at least the transport path, a power supply, a plurality of peripheral devices that includes a transporter and an articulated handling robot attached to the transporter, wherein the transporter is configured to autonomously move about the transport path and the articulated handling robot is configured to move a first tray between at least a first instrument and a second instrument in a plurality of instruments;

the one or more programs singularly or collectively using the one or more processors to execute a method comprising:

(A) obtaining, in electronic form, a first plurality of organic engineering targets, wherein the first plurality of organic engineering targets is defined by a user at the device, and each organic engineering target in the first plurality of organic engineering targets is an assembly of nucleic acid components, a plurality of reagents of nucleic acid components, a different predetermined polymer, a different predetermined peptide, or a different predetermined protein;

(B) assigning, via the controller, the first plurality of organic engineering targets to a first uncompiled workflow, wherein
the first uncompiled workflow is configured to produce the first plurality of organic engineering targets,
the first uncompiled workflow is associated with a first subset of process modules in a plurality of process modules,
each respective process module in the plurality of process modules is associated with a different subset of unit operation definitions in a plurality of unit operation definitions,
each respective unit operation definition in the plurality of unit operation definitions is independently associated with a corresponding time interval, and
each respective unit operation definition in the plurality of unit operation definitions is independently associated with a first subset of instruments in the plurality of instruments;
(C) translating, via the controller, for each respective organic engineering target in the first plurality of organic engineering targets, the first uncompiled workflow into a corresponding instance of a compiled first workflow for the respective organic engineering target using the transport path without human input, wherein the corresponding instance of the compiled first workflow comprises:
(i) for each respective instrument in the first subset of instruments:
(a) an address of the respective instrument comprising:
a coarse grain address of the respective instrument that is associated with a marker of the respective instrument configured to provide positional information to localize the transporter, and
(b) one or more execution instructions comprising:
a logical dependency of one or more unit operations of the compiled workflow defining procedures for processing samples,
a coarse traverse instruction that commands the transporter to traverse to the respective marker of the respective instrument, and
a fine traverse instruction that commands the articulated handling robot to move to at least one spatial coordinate associated with the respective instrument,
(ii) a first plurality of unit operations, wherein the first plurality of unit operations is temporally organized into a linear temporal order, and wherein each respective unit operation in the first plurality of unit operations is characterized by the time interval of the corresponding unit operation definition,
thereby forming a plurality of instances of the compiled first workflow.

2. The method of claim 1, wherein the transporter further comprises a positioning system that is configured to locate and guide the transporter within the transport path.

3. The method of claim 2, wherein:
the positioning system comprises a global positioning system, and
the respective marker of the respective instrument is a global positioning system coordinate.

4. The method of claim 2, wherein the positioning system comprises a representation of a marker positioning of the transport path.

5. The method of claim 4, wherein the representation of the marker positioning of the transport path is either an image feed or a video feed.

6. The method of claim 5, wherein either a low-pass filter or a Gaussian blurring function is applied to the representation of the marker positioning of the transport path.

7. The method of claim 2, wherein the transporter further comprises an inertial measurement unit that is configured to verify and correct each execution of the coarse traverse instruction of the respective instruments.

8. The method of claim 2, wherein the articulated handling robot further comprises a plurality of sensors, wherein each sensor in the plurality of sensors is configured to provide information related to a spatial location of the articulated handling robot and a marker positioning of each visible marker.

9. The method of claim 8, wherein the transporter further comprises a proportional-integral-derivative controller that is in electrical communication with the plurality of sensors in order to maintain a spatial location of the transporter.

10. The method of claim 8, wherein:
the articulated handling robot is configured to transfer the first tray to a first instrument in the plurality of instruments using a safety transfer procedure when a readout from the plurality of sensors fails to satisfy a threshold proximity value with respect to an actual physical location of the first instrument; and
the articulated handling robot is configured to transfer the first tray to the first instrument using a default transfer procedure when the readout from the plurality of sensors satisfies the threshold proximity value with respect to the actual physical location of the first instrument.

11. The method of claim 1, wherein the plurality of instruments comprises a centrifuge, a Peltier temperature controller, an incubator, a shaking incubator, a magnetic separator, a peeler, a liquid handling robot, a dispenser, a sealer, a plate reader, a liquid chromatography system, a gas chromatography system, a mass spectrometry system, a microscope, an electrophoresis device, an electroporation device, a clone separation device, a clone selection device, and a thermal cycler.

12. The method of claim 1, wherein each organic engineering target in the first plurality of organic engineering targets is a different predetermined polymer.

13. The method of claim 1, wherein each organic engineering target in the first plurality of organic engineering targets comprises a chemical compound that satisfies a the Lipinski rule of five criteria.

14. The method of claim 1, wherein the plurality of unit operations includes centrifugation, chilled incubation, heated incubation, magnetic separation, peeling, pipetting, dispensing, sealing, shaking incubation, spectrophotometry, chromatography, mass spectrometry, microscopic imaging, electrophoresis, electroporation, clone separation, colony selection, and thermal cycling.

15. A system for implementing workflows comprising a first device, wherein the first device comprises:
a display;
a power supply;
a communications interface;
one or more peripheral devices including a reagent handling device, the reagent handling device comprising:
a wash manifold,
a primary valve that regulates an internal flow path in the reagent handling device,
a plurality of reagent containers, wherein each reagent container in the plurality of reagent containers comprises a valve that controls a flow from the respective reagent container to the primary valve, a sterilization container configured to hold a sterilization fluid, the sterilization container comprising a valve that regulates a flow of the sterilization fluid either to the primary valve or to the wash manifold, the wash manifold is coupled to the respective valve of each reagent container in the plurality of reagent containers, wherein the wash manifold regulates the flow of the sterilization fluid from the sterilization container to the plurality of reagent containers, and a dispense manifold that is coupled to the primary valve and comprises a plurality of dispensers, the dispense manifold configured to control a flow from the primary valve to the plurality of dispensers;

one or more processors;

memory; and one or more programs, wherein the one or more programs are stored in the memory and are configured to be executed by the one or more processors, the one or more programs including instructions for:

(A) obtaining, in electronic form, a first plurality of organic engineering targets;

(B) assigning the first plurality of organic engineering targets to a first uncompiled workflow, wherein
the first uncompiled workflow is configured to produce the first plurality of organic engineering targets,
the first uncompiled workflow comprises a branch condition, a loop condition, or a nested condition,
the first uncompiled workflow is associated with a first subset of process modules in a plurality of process modules,
each respective process module in the plurality of process modules is associated with a different subset of unit operation definitions in a plurality of unit operation definitions,
each respective unit operation definition in the plurality of unit operation definitions is independently associated with a corresponding time interval, and
each respective unit operation definition in the plurality of unit operation definitions is independently associated with a first subset of instruments in a plurality of instruments;

(C) translating, for each respective organic engineering target in the first plurality of organic engineering targets, the first uncompiled workflow into a corresponding instance of a compiled first workflow for the respective organic engineering target using a transport path without human input, wherein the corresponding instance of the compiled first workflow comprises:
(i) for each respective instrument in the first subset of instruments:
(a) an address of the respective instrument comprising:
a coarse grain address of the respective instrument that is associated with a marker of the respective instrument configured to provide positional information to localize a transporter, wherein an articulated handling robot is attached to the transporter, and
(b) one or more execution instructions comprising:
a logical dependency of one or more unit operations of the compiled workflow defining procedures for processing samples,
a coarse traverse instruction that commands the transporter to traverse to the respective marker of the respective instrument, and
a fine traverse instruction that commands the articulated handling robot to move to at least one spatial coordinate associated with the respective instrument, and
(ii) a first plurality of unit operations, wherein the first plurality of unit operations is temporally organized into a linear temporal order by resolving the branch condition, the loop condition, or the nested condition based on a value associated with the branch condition, the loop condition, or the nested condition, and wherein, each respective unit operation in the first plurality of unit operations is characterized by the time interval of the corresponding unit operation definition, thereby forming a plurality of instances of the compiled first workflow.

16. The system of claim 15, wherein a pressure regulator is coupled to each of the sterilization container, the primary valve, and each reagent container in the plurality of reagent containers.

17. The system of claim 16, wherein each pressure regulator further comprises a filter that is configured to prevent contamination of the respective reagent container.

18. The system of claim 16, wherein each pressure regulator further comprises a check valve.

19. The system of claim 15, wherein the reagent handling device further comprises a pump coupled to the primary valve that drives the internal flow path in the reagent handling device.

20. The system of claim 15, wherein the reagent handling device further comprises a dispensing cycle that is configured to dispense a selection from a predetermined set of reagent containers in the plurality of reagent containers.

21. The system of claim 15, wherein the reagent handling device further comprises a first sterilization cycle that is configured to sterilize a portion of the system.

22. The system of claim 15, wherein the reagent handling device further comprises a second sterilization cycle that is configured to purge a portion of the system.

23. The system of claim 15, wherein each component of the reagent handling device is coupled through removable tubing.

24. The system of claim 15, wherein human intervention is only required to replenish a respective reagent of each reagent container in the plurality of reagent containers and to replenish the sterilization fluid of the sterilization container.

25. A method of implementing one or more workflows:
at a device comprising one or more processors, memory storing one or more programs for execution by the one or more processors, a controller, a plurality of instruments including a multi-well plate centrifuge instrument, a communications interface in electrical communication with at least the plurality of instruments, and a power supply;
the one or more programs singularly or collectively using the one or more processors to execute a method comprising:
(A) obtaining in electronic form, a first plurality of organic engineering targets;
(B) assigning, via the controller, the first plurality of organic engineering targets to a first uncompiled workflow, wherein
the first uncompiled workflow is configured to produce each organic engineering target in the first plurality of organic engineering targets in a corresponding well in a plate in a first set of multi-well plates, the first uncompiled workflow comprises a branch condition, a loop condition, or a nested condition, the first uncompiled workflow is associated with a first subset of process modules in a plurality of process modules, each respective process module in the plurality of process modules is associated with a different subset of unit operation definitions in a plurality of unit operation definitions, each respective unit operation definition in the plurality of unit operation definitions is independently associated with a corresponding time interval, and each respective unit operation definition in the plurality of unit operation definitions is independently associated with a first subset of instruments in the plurality of instruments, wherein the first subset of instruments includes the multi-well plate centrifuge instrument; and (C) translating, via the controller, for each respective organic engineering target in the first plurality of organic engineering targets, the first uncompiled workflow into a corresponding instance of a compiled first workflow for the respective organic engineering target using a transport path without human input, wherein the corresponding instance of the compiled first workflow comprises:

(i) for each respective instrument in the first subset of instruments (a) an address of the respective instrument, and (b) one or more execution instructions, wherein the one or more execution instructions for a multi-well plate centrifuge instrument comprise:

b.i) determining a mass of each multi-well plate in a first set of multi-well plates, b.ii) disposing each multi-well plate in the first set of multi-well plates into the multi-well plate centrifuge instrument, b.iii.1) obtaining a set of counter balances corresponding to the first set of multi-well plates, b.iii.2) disposing each respective counter balance in the multi-well plate centrifuge instrument at a position opposite the corresponding multi-well plate in the first set of multi-well plates, b.iii) adjusting, without human intervention, a mass of each respective counter balance in the set of counter balances to be equal to the corresponding multi-well plate in the first set of multi-well plates, and b.iv) operating the multi-well centrifuge instrument, and (ii) a first plurality of unit operations, wherein the first plurality of unit operations is temporally organized into a linear temporal order by resolving the branch condition, the loop condition, or the nested condition based on a value associated with the branch condition, the loop condition, or the nested condition, and wherein each respective unit operation in the first plurality of unit operations is characterized by the time interval of the corresponding unit operation definition, thereby forming a plurality of instances of the compiled first workflow.

26. The method of claim 25, wherein the first set of multi-well plates is a set of one multi-well plate.

27. The method of claim 25, wherein the first set of multi-well plates is a set of from two multi-well plates to five multi-well plates.

28. The method of claim 25, wherein the adjusting b.iii) further comprises pumping fluid to the respective counter balance in order to adjust the mass therein.

29. The method of claim 25, wherein the adjusting b.iii) further comprises drawing fluid from the respective counter balance in order to adjust the mass therein.

30. The method of claim 25, wherein each counter balance in the set of counter balances comprises a bottom end portion that is configured to pool fluid therein.

31. The method of claim 25, wherein the determining b.i) and the adjusting b.iii) are performed simultaneously.

32. The method of claim 25, wherein the adjusting b.iii) further comprises storing the adjusted mass of each respective counter balance in the set of counter balances.

33. The method of claim 25, wherein the one or more instructions for the multi-well plate centrifuge instrument further comprises:

b.v) determining a mass of each multi-well plate in a second set of multi-well plates, b.vi) disposing each multi-well plate in the second set of multi-well plates into the centrifuge, wherein each respective multi-well plate in the second set of multi-well plates has a corresponding counter balance in a second set of counter balances disposed in the multi-well plate centrifuge instrument at a position opposite the respective multi-well plate, b.vii) adjusting, without human intervention, the mass of each counter balance in the second set of counter balances to be equal to the mass of the corresponding multi-well plate in the second set of multi-well plates, and b.viii) operating the multi-well plate centrifuge instrument.

34. The method of claim 33, wherein the second set of multi-well plates is the first set of multi-well plates.

* * * * *